US010006052B2

(12) United States Patent
Jarjour et al.

(10) Patent No.: US 10,006,052 B2
(45) Date of Patent: Jun. 26, 2018

(54) LAGLIDADG HOMING ENDONUCLEASE CLEAVING THE C-C CHEMOKINE RECEPTOR TYPE-5 (CCR5) GENE AND USES THEREOF

(71) Applicants: Cellectis, Paris (FR); Precision Genome Engineering, Inc., Tumwater, WA (US)

(72) Inventors: Jordan Jarjour, Seattle, WA (US); Alexander Astrakhan, Seattle, WA (US)

(73) Assignees: CELLECTIS, Paris (FR); PRECISION GENOME ENGINEERING, INC., Tumwater, WA (US)

( * ) Notice: Subject to any disclaimer, the term of this patent is extended or adjusted under 35 U.S.C. 154(b) by 0 days. days.

(21) Appl. No.: 14/891,202

(22) PCT Filed: May 28, 2014

(86) PCT No.: PCT/EP2014/061186
§ 371 (c)(1),
(2) Date: Nov. 13, 2015

(87) PCT Pub. No.: WO2014/191525
PCT Pub. Date: Dec. 4, 2014

(65) Prior Publication Data
US 2016/0102323 A1   Apr. 14, 2016

(30) Foreign Application Priority Data

May 31, 2013   (DK) .................................. 2013 70302

(51) Int. Cl.
*C12N 15/90* (2006.01)
*C12N 9/22* (2006.01)
*A61K 35/17* (2015.01)
*A61K 38/46* (2006.01)

(52) U.S. Cl.
CPC ............ *C12N 15/907* (2013.01); *A61K 35/17* (2013.01); *A61K 38/465* (2013.01); *C12N 9/22* (2013.01); *C12Y 301/00* (2013.01)

(58) Field of Classification Search
None
See application file for complete search history.

(56) References Cited

U.S. PATENT DOCUMENTS

2012/0276074 A1* 11/2012 Scharenberg .......... A61K 38/45
424/94.2

FOREIGN PATENT DOCUMENTS

WO   2011/156430 A2   12/2011

OTHER PUBLICATIONS

Ngo et al. in the Protein Folding Problem and Tertiary Structure Prediction, 1994, Merz et al. (ed.), Birkhauser, Boston, MA, pp. 433 and 492-495.*
Gaj Thomas et al: "Targeted gene knockout by direct delivery of zinc-finger nuclease proteins", Nature Methods, vol. 9, No. 8, Aug. 2012 (Aug. 2012), pp. 805-807.
C. Mussolino et al: "A novel TALE nuclease scaffold enables high genome editing activity in combination with low toxicity", Nucleic Acids Research, vol. 39, No. 21, Aug. 3, 2011 (Aug. 3, 2011), pp. 9283-9293.
Kiem Hans-Peter et al: "Hematopoietic-Stem-Cell-Based Gene Therapy for HIV Disease", Cell Stem Cell, vol. 10, No. 2, Feb. 2012 (Feb. 2012), pp. 137-147.
Baxter S et al: "Engineering domain fusion chimeras from I-Onul family LAGLIDADG homing endonucleases", Nucleic Acids Research, Oxford University Press, GB, vol. 40, No. 16, Sep. 1, 2012 (Sep. 1, 2012), pp. 7985-8000.
Lai Yu: "CCR5-Targeted Hematopoietic Stem Cell Gene Approaches for HIV Disease: Current Progress and Future Prospects", Current Stem Cell Research & Therapy, vol. 7, No. 4, Jul. 2012 (Jul. 2012), pp. 310-317.
Hafez Mohamed et al: "Homing endonucleases: DNA scissors on a mission", Genome, vol. 55, No. 8, Aug. 1, 2012 (Aug. 1, 2012), pp. 553-569.
S. Boissel et al: "megaTALs: a rare-cleaving nuclease architecture for therapeutic genome engineering", Nucleic Acids Research, vol. 42, No. 4, Nov. 26, 2013 (Nov. 26, 2013), pp. 2591-2601.

* cited by examiner

*Primary Examiner* — Richard G Hutson
(74) *Attorney, Agent, or Firm* — Arrigo, Lee, Guttmann & Mouta-Bellum LLP

(57) ABSTRACT

Disclosed herein are compositions for inactivating the human CCR5 gene comprising engineered LAGLIDADG homing endonucleases (LHEs) and their derivatives, particularly derived from members of the \-Onul subfamily of LHE. Polynucleotides encoding such endonucleases, vectors comprising said polynucleotides, cells comprising or having been treated with such endonucleases, and therapeutic compositions deriving therefrom are also provided.

14 Claims, 17 Drawing Sheets

FIG. 15

SEQUENCE LISTING

```
<160> NUMBER OF SEQ ID NOS: 33

<210> SEQ ID NO 1
<211> LENGTH: 909
<212> TYPE: DNA
<213> ORGANISM: Ophiostoma novo-ulmi specie
<220> FEATURE:
<223> OTHER INFORMATION: natural I-OnuI

<400> SEQUENCE: 1
atggcataca tgtcgcgcag agagtccatc aacccatgga ttctgactgg tttcgctgat      60
gccgaaggat ccttcttgct gagaatccga aacaataaca agagctccgt gggttactct     120
accgagttgg gctttcaaat cactctgcac aacaaggaca aatcgattct ggagaatatc     180
cagtcgactt ggaaggtcgg cgtgattgct aactcaggcg acaatgccgt cagtctgaaa     240
gttacgcgtt tcgaagattt gaaagtgatt atcgaccact tcgagaaata tccgctgatt     300
acccagaaat tgggcgatta caagttgttt aaacaggcat tcagcgtcat ggagaacaaa     360
gaacatctta aggagaatgg gattaaggag ctcgtacgaa tcaaagctaa gatgaattgg     420
```

```
ggtctcactg acgaattgaa aaaagcattt ccagagaaca ttagcaaaga gcgccccctt    480
atcaataaga acattccgaa tttcaaatgg ctggctggat tcacatctgg tgaaggctgc    540
ttctttgtga acttgatcaa gtccaaatct aagctgggtg tacaggttca attggtcttc    600
agcattactc agcacatcag agacaagaac ctgatgaatt cattgataac atacctaggc    660
tgtggttaca tcaaagagaa gaacaagtcc gagttcagtt ggctcgactt tgtggttacc    720
aaattcagcg atatcaacga caagatcatt ccggtattcc aggaaaatac tctgattggc    780
gtcaaactcg aggactttga agattggtgc aaggttgcca aattgatcga agagaagaaa    840
cacctgaccg aatccggttt ggatgagatt aagaaaatca agctgaacat gaacaaaggt    900
cgtgtcttc                                                            909
```

<210> SEQ ID NO 2
<211> LENGTH: 303
<212> TYPE: PRT
<213> ORGANISM: Ophiostoma novo-ulmi specie
<220> FEATURE:
<223> OTHER INFORMATION: natural I-OnuI

<400> SEQUENCE: 2

```
Met Ala Tyr Met Ser Arg Arg Glu Ser Ile Asn Pro Trp Ile Leu Thr
1               5                   10                  15

Gly Phe Ala Asp Ala Glu Gly Ser Phe Leu Leu Arg Ile Arg Asn Asn
            20                  25                  30

Asn Lys Ser Ser Val Gly Tyr Ser Thr Glu Leu Gly Phe Gln Ile Thr
        35                  40                  45

Leu His Asn Lys Asp Lys Ser Ile Leu Glu Asn Ile Gln Ser Thr Trp
    50                  55                  60

Lys Val Gly Val Ile Ala Asn Ser Gly Asp Asn Ala Val Ser Leu Lys
65                  70                  75                  80

Val Thr Arg Phe Glu Asp Leu Lys Val Ile Ile Asp His Phe Glu Lys
                85                  90                  95

Tyr Pro Leu Ile Thr Gln Lys Leu Gly Asp Tyr Lys Leu Phe Lys Gln
            100                 105                 110

Ala Phe Ser Val Met Glu Asn Lys Glu His Leu Lys Glu Asn Gly Ile
        115                 120                 125

Lys Glu Leu Val Arg Ile Lys Ala Lys Met Asn Trp Gly Leu Thr Asp
    130                 135                 140

Glu Leu Lys Lys Ala Phe Pro Glu Asn Ile Ser Lys Glu Arg Pro Leu
145                 150                 155                 160

Ile Asn Lys Asn Ile Pro Asn Phe Lys Trp Leu Ala Gly Phe Thr Ser
                165                 170                 175

Gly Glu Gly Cys Phe Phe Val Asn Leu Ile Lys Ser Lys Ser Lys Leu
            180                 185                 190

Gly Val Gln Val Gln Leu Val Phe Ser Ile Thr Gln His Ile Arg Asp
        195                 200                 205

Lys Asn Leu Met Asn Ser Leu Ile Thr Tyr Leu Gly Cys Gly Tyr Ile
    210                 215                 220

Lys Glu Lys Asn Lys Ser Glu Phe Ser Trp Leu Asp Phe Val Val Thr
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Glu Asp Trp Cys Lys Val
            260                 265                 270
```

```
Ala Lys Leu Ile Glu Glu Lys Lys His Leu Thr Glu Ser Gly Leu Asp
        275                 280                 285

Glu Ile Lys Lys Ile Lys Leu Asn Met Asn Lys Gly Arg Val Phe
        290                 295                 300

<210> SEQ ID NO 3
<211> LENGTH: 22
<212> TYPE: DNA
<213> ORGANISM: artificial sequence
<220> FEATURE:
<223> OTHER INFORMATION: Target CCR5_S02

<400> SEQUENCE: 3
atgaagaaga ttccagagaa ga                                          22

<210> SEQ ID NO 4
<211> LENGTH: 22
<212> TYPE: DNA
<213> ORGANISM: artificial sequence
<220> FEATURE:
<223> OTHER INFORMATION: Target CCR5_S03

<400> SEQUENCE: 4
gtaaagatga ttcctgggag ag                                          22

<210> SEQ ID NO 5
<211> LENGTH: 22
<212> TYPE: DNA
<213> ORGANISM: artificial sequence
<220> FEATURE:
<223> OTHER INFORMATION: Target CCR5_S08

<400> SEQUENCE: 5
cttccaggaa ttctttggcc tg                                          22

<210> SEQ ID NO 6
<211> LENGTH: 22
<212> TYPE: DNA
<213> ORGANISM: artificial sequence
<220> FEATURE:
<223> OTHER INFORMATION: Target CCR5_S12

<400> SEQUENCE: 6
agctctcatt ttccatacag tc                                          22

<210> SEQ ID NO 7
<211> LENGTH: 22
<212> TYPE: DNA
<213> ORGANISM: artificial sequence
<220> FEATURE:
<223> OTHER INFORMATION: Target CCR5_S63

<400> SEQUENCE: 7
gcagctctca ttttccatac ag                                          22

<210> SEQ ID NO 8
<211> LENGTH: 22
<212> TYPE: DNA
<213> ORGANISM: artificial sequence
<220> FEATURE:
<223> OTHER INFORMATION: Target CCR5_S66

<400> SEQUENCE: 8
tctggaagaa tttccagaca tt                                          22
```

<210> SEQ ID NO 9
<211> LENGTH: 909
<212> TYPE: DNA
<213> ORGANISM: artificial sequence
<220> FEATURE:
<223> OTHER INFORMATION: LHE CCR5_S02_1F5

<400> SEQUENCE: 9

```
atggcataca tgtcgcgcag agagtccatc aacccatgga ttctgactgg tttcgctgat        60
gccgaaggat ctttcggtct atacatctac aactcaaaca cggtgaaggt agggtaccga       120
actcaactga cattcactat cgagctgcac aacaaggaca atcgattct ggagaatatc        180
cagtcgactt ggaaggtcgg caaaatcaac aacaacggcg acaactacgt caggctgaag       240
gtcacccgtt tcgaagattt gaaagtgatt atcgaccact tcgagaaata ccgctgatt        300
acccagaaat tgggcgatta caagttgttt aaacaggcat tcagcgtcat ggagaacaaa       360
gaacatctta aggagaatgg gattaaggag ctcgtacgaa tcaaagctaa gatgaattgg       420
ggtctcactg acgaattgaa aaagcatttt ccagagaaca ttagcaaaga gcgccccctt       480
atcaataaga acattccgaa tttcaaatgg ctggctggat tcacatctgg tgaaggcaac       540
ttctacgtga agctaatcaa gagcaagcaa cagagcaagg tatacgtgag tctgatattc       600
agaatctctc agcacatcag agacaagaac ctgatgaatt cattgataac atacctaggc       660
tgtggtcaca tctacgagac taaccgatct gagcacagtt ggctcgagtt cgtcgtatca       720
aaattcagcg atatcaacga caagatcatt ccggtattcc aggaaaatac tctgattggc       780
gtcaaactcg aggactttga agattggtgc aaggttgcca aattgatcga agagaagaaa       840
cacctgaccg aatccggttt ggatgagatt aagaaaatca agctgaacat gaacaaaggt       900
cgtgtcttc                                                               909
```

<210> SEQ ID NO 10
<211> LENGTH: 303
<212> TYPE: PRT
<213> ORGANISM: artificial sequence
<220> FEATURE:
<223> OTHER INFORMATION: LHE CCR5_S02_1F5

<400> SEQUENCE: 10

```
Met Ala Tyr Met Ser Arg Arg Glu Ser Ile Asn Pro Trp Ile Leu Thr
1               5                   10                  15

Gly Phe Ala Asp Ala Glu Gly Ser Phe Gly Leu Tyr Ile Tyr Asn Ser
            20                  25                  30

Asn Thr Val Lys Val Gly Tyr Arg Thr Gln Leu Thr Phe Thr Ile Glu
        35                  40                  45

Leu His Asn Lys Asp Lys Ser Ile Leu Glu Asn Ile Gln Ser Thr Trp
    50                  55                  60

Lys Val Gly Lys Ile Asn Asn Asn Gly Asp Asn Tyr Val Arg Leu Lys
65                  70                  75                  80

Val Thr Arg Phe Glu Asp Leu Lys Val Ile Ile Asp His Phe Glu Lys
                85                  90                  95

Tyr Pro Leu Ile Thr Gln Lys Leu Gly Asp Tyr Lys Leu Phe Lys Gln
            100                 105                 110

Ala Phe Ser Val Met Glu Asn Lys Glu His Leu Lys Glu Asn Gly Ile
        115                 120                 125

Lys Glu Leu Val Arg Ile Lys Ala Lys Met Asn Trp Gly Leu Thr Asp
    130                 135                 140

Glu Leu Lys Lys Ala Phe Pro Glu Asn Ile Ser Lys Glu Arg Pro Leu
```

```
                  145                 150                 155                 160
Ile Asn Lys Asn Ile Pro Asn Phe Lys Trp Leu Ala Gly Phe Thr Ser
                165                 170                 175

Gly Glu Gly Asn Phe Tyr Val Lys Leu Ile Lys Ser Lys Gln Gln Ser
            180                 185                 190

Lys Val Tyr Val Ser Leu Ile Phe Arg Ile Ser Gln His Ile Arg Asp
        195                 200                 205

Lys Asn Leu Met Asn Ser Leu Ile Thr Tyr Leu Gly Cys Gly His Ile
    210                 215                 220

Tyr Glu Thr Asn Arg Ser Glu His Ser Trp Leu Glu Phe Val Val Ser
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Glu Asp Trp Cys Lys Val
            260                 265                 270

Ala Lys Leu Ile Glu Glu Lys His Leu Thr Glu Ser Gly Leu Asp
        275                 280                 285

Glu Ile Lys Lys Ile Lys Leu Asn Met Asn Lys Gly Arg Val Phe
    290                 295                 300

<210> SEQ ID NO 11
<211> LENGTH: 909
<212> TYPE: DNA
<213> ORGANISM: artificial sequence
<220> FEATURE:
<223> OTHER INFORMATION: LHE CCR5_S08 _1B6

<400> SEQUENCE: 11
atggcataca tgtcgcgcag agagtccatc aacccatgga ttctgactgg tttcgctgat      60
gccgaaggat cattcctgct aagaatccgt aacacgaaca accggacagt agggtactac     120
acttcactgg tattcgaaat cactctgcac aacaaggaca atcgattct ggagaatatc      180 cagtcgactt ggaaggtcgg cacaatcaac aaccgaggcg acggcaccgt cagactgagc     240
gtcactcgtt tcgaagattt gaaagtgatt atcgaccact tcgagaaata tccgctgatt     300
acccagaaat tgggcgatta caagttgttt aaacaggcat tcagcgtcat ggagaacaaa     360
gaacatctta aggagaatgg gattaaggag ctcgtacgaa tcaaagctaa gatgaattgg     420
ggtctcactg acgaattgaa aaaagcattt ccagagaaca ttagcaaaga gcgcccctt     480 atcaataaga acattccgaa tttcaaatgg ctggctggat tcacatctgg tgaaggcaca     540
ttctacgtgc acctagcaaa gtctaaagct agcggcaagg tatacgtgcg actgaggttc     600
ataatcggcc agcacatcag agacaagaac ctgatgaatt cattgataac atacctaggc     660
tgtggtaaga tccaggagaa gaacaggtct gagggcagta tgctccactt catagtaact     720
aaattcagcg atatcaacga caagatcatt ccggtattcc aggaaaatac tctgattggc     780
gtcaaactcg aggactttga agattggtgc aaggttgcca aattgatcga agagaagaaa     840 caccctgaccg aatccggttt ggatgagatt aagaaaatca agctgaacat gaacaaaggt     900
cgtgtcttc                                                              909

<210> SEQ ID NO 12
<211> LENGTH: 303
<212> TYPE: PRT
<213> ORGANISM: artificial sequence
<220> FEATURE:
<223> OTHER INFORMATION: LHE CCR5_S08 _1B6
```

<400> SEQUENCE: 12

Met Ala Tyr Met Ser Arg Arg Glu Ser Ile Asn Pro Trp Ile Leu Thr
1               5                   10                  15

Gly Phe Ala Asp Ala Glu Gly Ser Phe Leu Leu Arg Ile Arg Asn Thr
            20                  25                  30

Asn Asn Arg Thr Val Gly Tyr Tyr Thr Ser Leu Val Phe Glu Ile Thr
        35                  40                  45

Leu His Asn Lys Asp Lys Ser Ile Leu Glu Asn Ile Gln Ser Thr Trp
    50                  55                  60

Lys Val Gly Thr Ile Asn Asn Arg Gly Asp Gly Thr Val Arg Leu Ser
65                  70                  75                  80

Val Thr Arg Phe Glu Asp Leu Lys Val Ile Ile Asp His Phe Glu Lys
                85                  90                  95

Tyr Pro Leu Ile Thr Gln Lys Leu Gly Asp Tyr Lys Leu Phe Lys Gln
            100                 105                 110

Ala Phe Ser Val Met Glu Asn Lys Glu His Leu Lys Glu Asn Gly Ile
        115                 120                 125

Lys Glu Leu Val Arg Ile Lys Ala Lys Met Asn Trp Gly Leu Thr Asp
    130                 135                 140

Glu Leu Lys Lys Ala Phe Pro Glu Asn Ile Ser Lys Glu Arg Pro Leu
145                 150                 155                 160

Ile Asn Lys Asn Ile Pro Asn Phe Lys Trp Leu Ala Gly Phe Thr Ser
                165                 170                 175

Gly Glu Gly Thr Phe Tyr Val His Leu Ala Lys Ser Lys Ala Ser Gly
            180                 185                 190

Lys Val Tyr Val Arg Leu Arg Phe Ile Ile Gly Gln His Ile Arg Asp
        195                 200                 205

Lys Asn Leu Met Asn Ser Leu Ile Thr Tyr Leu Gly Cys Gly Lys Ile
    210                 215                 220

Gln Glu Lys Asn Arg Ser Glu Gly Ser Met Leu His Phe Ile Val Thr
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Glu Asp Trp Cys Lys Val
            260                 265                 270

Ala Lys Leu Ile Glu Glu Lys Lys His Leu Thr Glu Ser Gly Leu Asp
        275                 280                 285

Glu Ile Lys Lys Ile Lys Leu Asn Met Asn Lys Gly Arg Val Phe
    290                 295                 300

<210> SEQ ID NO 13
<211> LENGTH: 22
<212> TYPE: DNA
<213> ORGANISM: artificial sequence
<220> FEATURE:
<223> OTHER INFORMATION: Target Onu-I wild type

<400> SEQUENCE: 13
tttccactta ttcaaccttt ta                                           22

<210> SEQ ID NO 14
<211> LENGTH: 909
<212> TYPE: DNA
<213> ORGANISM: artificial sequence
<220> FEATURE:
<223> OTHER INFORMATION: LHE CCR5_S08_1B6 RD1-18

<400> SEQUENCE: 14

```
atggcataca tgtcgcgcag agagtccatc aacccatgga ttctgactgg tttcgctgat      60
gccgaaggat cattcatgct aagaatccgt aacacgaaca accggacagt agggtactac     120
acttcactgg tattcgaaat cactctgcac aacaaggaca aatcgattct ggagaatatc     180
cagtcgactt ggaaggtcgg cacaatcaac aaccgaggcg acggcaccgt cagactgagc     240
gtcactcgtt tcgaagattt gaaagtgatt atcgaccact tcgagaaata tccgctgatt     300
acccagaaat tgggcgatta caagttgttt aaacaggcat tcagcgtcat ggagaacaaa     360
gaacatctta aggagaatgg gattaaggag ctcgtacgaa tcaaagctaa gatgaattgg     420
ggtctcactg acgaattgaa aaagcatttt ccagagaaca ttagcaaaga gcgccccctt     480
atcaataaga acattccgaa tttcaaatgg ctggctggat tcacatctgg tgaaggcaca     540
ttctacgtgc acctagcaca gtctaaagct agcggcaagg tatacgtgcg actgaggttc     600
ataatcggcc agcacatcag agacaagaac ctgatgaatt cattgataac ataccctaggc    660
tgtggtacga tccaggagaa gaacaggtct gagggcagta tgctccactt catagtaact     720
aaattcagcg atatcaacga caagatcatt ccggtattcc aggaaaatac tctgattggc     780
gtcaaactcg aggactttga agattggtgc aaggttgcca aattgatcga agagaagaaa     840
caccttgaccg aatccggttt ggatgagatt aagaaaatca agctgaacat gaacaaaggt     900
cgtgtcttc                                                             909
```

<210> SEQ ID NO 15
<211> LENGTH: 303
<212> TYPE: PRT
<213> ORGANISM: artificial sequence
<220> FEATURE:
<223> OTHER INFORMATION: LHE CCR5_S08_1B6 RD1-18

<400> SEQUENCE: 15

```
Met Ala Tyr Met Ser Arg Arg Glu Ser Ile Asn Pro Trp Ile Leu Thr
  1               5                  10                  15

Gly Phe Ala Asp Ala Glu Gly Ser Phe Met Leu Arg Ile Arg Asn Thr
             20                  25                  30

Asn Asn Arg Thr Val Gly Tyr Tyr Thr Ser Leu Val Phe Glu Ile Thr
         35                  40                  45

Leu His Asn Lys Asp Lys Ser Ile Leu Glu Asn Ile Gln Ser Thr Trp
     50                  55                  60

Lys Val Gly Thr Ile Asn Asn Arg Gly Asp Gly Thr Val Arg Leu Ser
 65                  70                  75                  80

Val Thr Arg Phe Glu Asp Leu Lys Val Ile Ile Asp His Phe Glu Lys
                 85                  90                  95

Tyr Pro Leu Ile Thr Gln Lys Leu Gly Asp Tyr Lys Leu Phe Lys Gln
            100                 105                 110

Ala Phe Ser Val Met Glu Asn Lys Glu His Leu Lys Glu Asn Gly Ile
        115                 120                 125

Lys Glu Leu Val Arg Ile Lys Ala Lys Met Asn Trp Gly Leu Thr Asp
    130                 135                 140

Glu Leu Lys Lys Ala Phe Pro Glu Asn Ile Ser Lys Glu Arg Pro Leu
145                 150                 155                 160

Ile Asn Lys Asn Ile Pro Asn Phe Lys Trp Leu Ala Gly Phe Thr Ser
                165                 170                 175

Gly Glu Gly Thr Phe Tyr Val His Leu Ala Gln Ser Lys Ala Ser Gly
            180                 185                 190
```

```
Lys Val Tyr Val Arg Leu Arg Phe Ile Ile Gly Gln His Ile Arg Asp
        195                 200                 205

Lys Asn Leu Met Asn Ser Leu Ile Thr Tyr Leu Gly Cys Gly Thr Ile
        210                 215                 220

Gln Glu Lys Asn Arg Ser Glu Gly Ser Met Leu His Phe Ile Val Thr
225                 230                 235                 240

Lys Phe Ser Asp Ile Asn Asp Lys Ile Ile Pro Val Phe Gln Glu Asn
        245                 250                 255

Thr Leu Ile Gly Val Lys Leu Glu Asp Phe Glu Asp Trp Cys Lys Val
        260                 265                 270

Ala Lys Leu Ile Glu Glu Lys Lys His Leu Thr Glu Ser Gly Leu Asp
        275                 280                 285

Glu Ile Lys Lys Ile Lys Leu Asn Met Asn Lys Gly Arg Val Phe
        290                 295                 300
```

<210> SEQ ID NO 16
<211> LENGTH: 909
<212> TYPE: DNA
<213> ORGANISM: artificial sequence
<220> FEATURE:
<223> OTHER INFORMATION: LHE CCR5_S08_1B6 RD2-16

<400> SEQUENCE: 16

```
atggcataca tgtcgcgcag agagtccatc aacccatgga ttctgactgg tttcgctgat      60
gccgaaggat cattcatgct aagaatccgt aacacgaaca gcggtcagt agggtactac     120
acttcactgg tattcgaaat cactctgcac aacaaggaca aatcgattct ggagaatatc    180
cagtcgactt ggaaggtcgg cacaatcaac aaccgaggcg acggcaccgt cagactgagc    240
gtcactcgtt tcgaagattt gaaagtgatt atcgaccact tcgagaaata tccgctgatt    300
acccagaaat tgggcgatta caagttgttt aaacaggcat tcagcgtcat ggagaacaaa    360
gaacatctta ggagaatgg gattaaggag ctcgtacgaa tcaaagctaa gatgaattgg    420
ggtctcactg acgaattgaa aaaagcattt ccagagaaca ttagcaaaga gcgcccctt    480
atcaataaga acattccgaa tttcaaatgg ctggctggat tcacatctgg tgaaggcaca    540
ttctacgtgc acctagcaaa gtctgaagct agcggcaagg tatacgtgcg actgaggttc    600
ataatcggcc agcacataga agacaagaac ctgatgaatt cattgataac ataacctaggc   660
tgtggtaaga tccaggagaa gaacaggtct aagggcagta tgctccactt catagtaact    720
aaattcagcg atatcaacga caagatcatt ccggtattcc aggaaaatac tctgattggc    780
gtcaaactcg aggactttga agattggtgc aaggttgcca aattgatcga agagaagaaa    840
cacctgaccg aatccggttt ggatgagatt aagaaaatca gctgaacat gaacaaaggt    900
cgtgtcttc                                                             909
```

<210> SEQ ID NO 17
<211> LENGTH: 303
<212> TYPE: PRT
<213> ORGANISM: artificial sequence
<220> FEATURE:
<223> OTHER INFORMATION: LHE CCR5_S08_1B6 RD2-16

<400> SEQUENCE: 17

```
Met Ala Tyr Met Ser Arg Arg Glu Ser Ile Asn Pro Trp Ile Leu Thr
1               5                   10                  15

Gly Phe Ala Asp Ala Glu Gly Ser Phe Met Leu Arg Ile Arg Asn Thr
            20                  25                  30
```

Asn Lys Arg Ser Val Gly Tyr Tyr Thr Ser Leu Val Phe Glu Ile Thr
            35                  40                  45

Leu His Asn Lys Asp Lys Ser Ile Leu Glu Asn Ile Gln Ser Thr Trp
 50                  55                  60

Lys Val Gly Thr Ile Asn Asn Arg Gly Asp Gly Thr Val Arg Leu Ser
 65                  70                  75                  80

Val Thr Arg Phe Glu Asp Leu Lys Val Ile Ile Asp His Phe Glu Lys
                85                  90                  95

Tyr Pro Leu Ile Thr Gln Lys Leu Gly Asp Tyr Lys Leu Phe Lys Gln
                100                 105                 110

Ala Phe Ser Val Met Glu Asn Lys Glu His Leu Lys Glu Asn Gly Ile
            115                 120                 125

Lys Glu Leu Val Arg Ile Lys Ala Lys Met Asn Trp Gly Leu Thr Asp
130                 135                 140

Glu Leu Lys Lys Ala Phe Pro Glu Asn Ile Ser Lys Glu Arg Pro Leu
145                 150                 155                 160

Ile Asn Lys Asn Ile Pro Asn Phe Lys Trp Leu Ala Gly Phe Thr Ser
                165                 170                 175

Gly Glu Gly Thr Phe Tyr Val His Leu Ala Lys Ser Glu Ala Ser Gly
                180                 185                 190

Lys Val Tyr Val Arg Leu Arg Phe Ile Ile Gly Gln His Ile Arg Asp
            195                 200                 205

Lys Asn Leu Met Asn Ser Leu Ile Thr Tyr Leu Gly Cys Gly Lys Ile
210                 215                 220

Gln Glu Lys Asn Arg Ser Lys Gly Ser Met Leu His Phe Ile Val Thr
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Glu Asp Trp Cys Lys Val
                260                 265                 270

Ala Lys Leu Ile Glu Glu Lys Lys His Leu Thr Glu Ser Gly Leu Asp
            275                 280                 285

Glu Ile Lys Lys Ile Lys Leu Asn Met Asn Lys Gly Arg Val Phe
            290                 295                 300

<210> SEQ ID NO 18
<211> LENGTH: 909
<212> TYPE: DNA
<213> ORGANISM: artificial sequence
<220> FEATURE:
<223> OTHER INFORMATION: LHE CCR5_S08_1B6 RD3-21

<400> SEQUENCE: 18
atggcataca tgtcgcgcag agagtccatc aacccatgga ttctgactgg tttcactgat      60
gccgaaggat cattcatgct aagaatccgt aacacgaaca accggtcagt agggtactac     120
acttcactgg tattcgaaat cactctgcac aacaaggaca aatcgattct tgagaatatc     180
cagtcgactt ggaaggtcgg cacaatcaac aaccgaggcg acggcaccgc cagactgagc     240
gtcactcgtt tcgaagattt gaaagtgatt atcgaccact cgagaaaata tccgctgatt     300
acccagaaat tgggcgatta caagttgttt aaacaggcat tcagcgtcat ggagaacaaa     360
gaacatctta aggagaatgg gattaaggag ctcgtacgaa tcaaagctaa gatgaattgg     420
ggtctcaatg acgaattgaa aaaagcattt ccagagaaca tcagcaaaga gcgccccctt     480
atcaataaga acattccgaa tctcaaatgg ctggctggat tcacatctgg tgaaggcaca     540

-continued

```
ttctacgtgc acctagcaaa gtctgaagct agcggcaagg tatacgtgcg actgaggttc    600
ataatcggcc agcacatcag agacaagaac ctgatgaatt cattgataac atacctaggc    660
tgtggtacga tccaggagaa gaacaggtct aagggcagta tgctccactt catagtaact    720
aaattcagcg atatcaacga caagatcatt ccggtattcc aggaaaatac tctgattggc    780
gtcaaactcg aggactttga agattggtgc aaggttgcca aattgatcga agagaagaaa    840
cacctgaccg aatccggttt ggatgagatt aagaaaatca agctgaacat gaacaaaggt    900
cgtgtcttc                                                             909
```

<210> SEQ ID NO 19
<211> LENGTH: 308
<212> TYPE: PRT
<213> ORGANISM: artificial sequence
<220> FEATURE:
<223> OTHER INFORMATION: LHE CCR5_S08_1B6 RD3-21

<400> SEQUENCE: 19

```
Met Ala Tyr Met Ser Arg Arg Glu Ser Ile Asn Pro Trp Ile Leu Thr
1               5                   10                  15

Gly Phe Ala Asp Ala Glu Gly Ser Phe Met Leu Arg Ile Arg Ser Thr
            20                  25                  30

Asn Lys Arg Ser Val Gly Tyr Tyr Thr Ser Leu Val Phe Glu Ile Thr
        35                  40                  45

Leu His Asn Lys Asp Lys Ser Ile Leu Glu Asn Ile Gln Ser Thr Trp
    50                  55                  60

Lys Val Gly Thr Ile Asn Asn Arg Gly Asp Gly Thr Val Arg Leu Ser
65                  70                  75                  80

Val Thr Arg Phe Glu Asp Leu Lys Val Ile Ile Asp His Phe Glu Lys
                85                  90                  95

Tyr Pro Leu Ile Thr Gln Lys Leu Gly Asp Tyr Lys Leu Phe Lys Gln
            100                 105                 110

Ala Phe Ser Val Met Glu Asn Lys Glu His Leu Lys Glu Asn Gly Ile
        115                 120                 125

Lys Glu Leu Val Arg Ile Arg Ala Lys Met Asn Trp Gly Leu Asn Asp
    130                 135                 140

Glu Leu Lys Lys Ala Phe Pro Glu Asn Ile Ser Lys Glu Arg Pro Leu
145                 150                 155                 160

Ile Asn Lys Asn Ile Pro Asn Leu Lys Trp Leu Ala Gly Phe Thr Ser
                165                 170                 175

Gly Glu Gly Thr Phe Tyr Val His Leu Ala Lys Ser Glu Ala Ser Gly
            180                 185                 190

Lys Val Tyr Val Arg Leu Arg Phe Ile Ile Gly Gln His Ile Arg Asp
        195                 200                 205

Lys Asn Leu Met Asn Ser Leu Ile Thr Tyr Leu Gly Cys Gly Thr Val
    210                 215                 220

Gln Glu Lys Asn Arg Ser Lys Gly Ser Met Leu His Phe Ile Val Thr
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Glu Asp Trp Cys Lys Val
            260                 265                 270

Ala Lys Leu Ile Glu Glu Lys Lys His Leu Thr Glu Ser Gly Leu Asp
        275                 280                 285
```

Glu Ile Lys Lys Ile Lys Leu Asn Met Asn Lys Gly Arg Val Phe Ser
    290                 295                 300

Gly Arg Val Phe
305

<210> SEQ ID NO 20
<211> LENGTH: 7265
<212> TYPE: DNA
<213> ORGANISM: homo sapiens
<220> FEATURE:
<223> OTHER INFORMATION: chemokine (C-C motif) receptor 5

<400> SEQUENCE: 20

| | | | | | |
|---|---|---|---|---|---|
| ccttttcagc | ttctagtttg | ctgaaactaa | tctgctatag | acagagactc | cggtgaacca | 60 |
| attttattag | gatttgatca | aataaactct | ctctgacaaa | ggactgctga | aagagtaact | 120 |
| aagagtttga | tgtttactga | gtgcatagta | tgtgctagat | gctggccgtg | gatgcctcat | 180 |
| agaatcctcc | caacaactca | tgaaatgact | actgtcattc | agcccaatac | ccagacgaga | 240 |
| aagctgaggg | taagacaggt | ttcaagcttg | gcagtctgac | tacagaggcc | actggcttag | 300 |
| cccctgggtt | agtctgcctc | tgtaggattg | ggggcacgta | attttgctgt | ttggggtctc | 360 |
| atttgccttc | ttagagatca | caagccaaag | cttttattc | tagagccaag | gtcacggaag | 420 |
| cccagagggc | atcttgtggc | tcgggagtag | ctctctgctg | tcttctcagc | tctgctgaca | 480 |
| atacttgaga | ttttcagatg | tcaccaaccg | ccaagagagc | ttgatatgac | tgtatatagt | 540 |
| atagtcataa | agaacctgaa | cttgaccata | tacttatgtc | atgtggaaaa | tttctcatag | 600 |
| cttcagatag | attatatctg | gagtgaagaa | tcctgccacc | tatgtatctg | gcatagtgtg | 660 |
| agtcctcata | aatgcttact | ggtttgaagg | gcaacaaaat | agtgaacaga | gtgaaaatcc | 720 |
| ccactaagat | cctgggtcca | gaaaagatg | ggaaacctgt | ttagctcacc | cgtgagccca | 780 |
| tagttaaaac | tctttagaca | acaggttgtt | tccgtttaca | gagaacaata | atattgggtg | 840 |
| gtgagcatct | gtgtggggt | tggggtggga | taggggatac | ggggagagtg | gagaaaaagg | 900 |
| ggacacaggg | ttaatgtgaa | gtccaggatc | ccctctaca | tttaaagttg | gtttaagttg | 960 |
| gctttaatta | atagcaactc | ttaagataat | cagaattttc | ttaaccttt | agccttactg | 1020 |
| ttgaaaagcc | ctgtgatctt | gtacaaatca | tttgcttctt | ggatagtaat | ttctttact | 1080 |
| aaaatgtggg | cttttgacta | gatgaatgta | aatgttcttc | tagctctgat | atcctttatt | 1140 |
| ctttatattt | tctaacagat | tctgtgtagt | gggatgagca | gagaacaaaa | acaaaataat | 1200 |
| ccagtgagaa | aagcccgtaa | ataaaccttc | agaccagaga | tctattctct | agcttatttt | 1260 |
| aagctcaact | taaaaagaag | aactgttctc | tgattctttt | cgccttcaat | acacttaatg | 1320 |
| atttaactcc | accctccttc | aaaagaaaca | gcatttccta | cttttatact | gtctatatga | 1380 |
| ttgatttgca | cagctcatct | ggccagaaga | gctgagacat | ccgttcccct | acaagaaact | 1440 |
| ctccccggta | agtaacctct | cagctgcttg | gcctgttagt | tagcttctga | gatgagtaaa | 1500 |
| agactttaca | ggaaacccat | agaagacatt | tggcaaacac | caagtgctca | tacaattatc | 1560 |
| ttaaaatata | atctttaaga | taaggaaagg | gtcacagttt | ggaatgagtt | tcagacggtt | 1620 |
| ataacatcaa | agatacaaaa | catgattgtg | agtgaaagac | tttaaaggga | gcaatagtat | 1680 |
| tttaataact | aacaatcctt | acctctcaaa | agaaagattt | gcagagagat | gagtcttagc | 1740 |
| tgaaatcttg | aaatcttatc | ttctgctaag | gagaactaaa | ccctctccag | tgagatgcct | 1800 |
| tctgaatatg | tgcccacaag | aagttgtgtc | taagtctggt | tctctttttt | cttttcctc | 1860 |
| cagacaagag | ggaagcctaa | aaatggtcaa | aattaatatt | aaattacaaa | cgccaaataa | 1920 |

```
aattttcctc taatatatca gtttcatggc acagttagta tataattctt tatggttcaa   1980
aattaaaaat gagcttttct aggggcttct ctcagctgcc tagtctaagg tgcagggagt   2040
ttgagactca cagggtttaa taagagaaaa ttctcagcta gagcagctga acttaaatag   2100
actaggcaag acagctggtt ataagactaa actacccaga atgcatgaca ttcatctgtg   2160
gtggcagacg aaacattttt tattatatta tttcttgggt atgtatgaca actcttaatt   2220
gtggcaactc agaaactaca aacacaaact tcacagaaaa tgtgaggatt ttacaattgg   2280
ctgttgtcat ctatgacctt ccctgggact tgggcacccg gccatttcac tctgactaca   2340
tcatgtcacc aaacatctga tggtcttgcc ttttaattct cttttcgagg actgagaggg   2400
agggtagcat ggtagttaag agtgcaggct tcccgcattc aaaatcggtt gcttactagc   2460
tgtgtggctt tgagcaagtt actcaccctc tctgtgcttc aaggtccttg tctgcaaaat   2520
gtgaaaaata tttcctgcct cataaggttg ccctaaggat taaatgaatg aatgggtatg   2580
atgcttagaa cagtgattgg catccagtat gtgccctcga ggcctcttaa ttattactgg   2640
cttgctcata gtgcatgttc tttgtgggct aactctagcg tcaataaaaa tgttaagact   2700
gagttgcagc cgggcatggt ggctcatgcc tgtaatccca gcattctagg aggctgaggc   2760
aggaggatcg cttgagccca ggagttcgag accagcctgg gcaacatagt gtgatcttgt   2820
atctataaaa ataaacaaaa ttagcttggt gtggtggcgc ctgtagtccc agccacttg   2880 gaggggtgag gtgagaggat tgcttgagcc cgggatggtc caggctgcag tgagccatga   2940
tcgtgccact gcactccagc ctgggcgaca gagtgagacc ctgtctcaca acaacaacaa   3000
caacaacaaa aaggctgagc tgcaccatgc ttgacccagt ttcttaaaat tgttgtcaaa   3060
gcttcattca ctccatggtg ctatagagca caagatttta tttggtgaga tggtgctttc   3120
atgaattccc ccaacagagc caagctctcc atctagtgga cagggaagct agcagcaaac   3180
cttcccttca ctacaaaact tcattgcttg gccaaaaaga gagttaattc aatgtagaca   3240
tctatgtagg caattaaaaa cctattgatg tataaaacag tttgcattca tggagggcaa   3300
ctaaatacat tctaggactt tataaaagat cacttttttat ttatgcacag ggtggaacaa   3360
gatggattat caagtgtcaa gtccaatcta tgacatcaat tattatacat cggagccctg   3420
ccaaaaaatc aatgtgaagc aaatcgcagc ccgcctcctg cctccgctct actcactggt   3480
gttcatcttt ggttttgtgg gcaacatgct ggtcatcctc atcctgataa actgcaaaag   3540
gctgaagagc atgactgaca tctacctgct caacctggcc atctctgacc tgttttttcct   3600 tcttactgtc cccttctggg ctcactatgc tgccgcccag tgggactttg gaaatacaat   3660
gtgtcaactc ttgacagggc tctatttat aggcttcttc tctggaatct tcttcatcat   3720
cctcctgaca atcgataggt acctggctgt cgtccatgct gtgtttgctt taaaagccag   3780
gacggtcacc tttggggtgg tgacaagtgt gatcacttgg gtggtggctg tgtttgcgtc   3840
tctcccagga atcatctta ccagatctca aaaagaaggt cttcattaca cctgcagctc   3900 tcatttcca tacagtcagt atcaattctg gaagaatttc cagacattaa agatagtcat   3960
cttggggctg gtcctgccgc tgcttgtcat ggtcatctgc tactcgggaa tcctaaaaac   4020
tctgcttcgg tgtcgaaatg agaagaagag gcacagggct gtgaggctta tcttcaccat   4080
catgattgtt tattttctct tctgggctcc ctacaacatt gtccttctcc tgaacacctt   4140
ccaggaattc tttggcctga ataattgcag tagctctaac aggttggacc aagctatgca   4200
ggtgacagag actcttggga tgacgcactg ctgcatcaac cccatcatct atgcctttgt   4260
```

```
cggggagaag ttcagaaact acctcttagt cttcttccaa aagcacattg ccaaacgctt    4320
ctgcaaatgc tgttctattt tccagcaaga ggctcccgag cgagcaagct cagtttacac    4380
ccgatccact ggggagcagg aaatatctgt gggcttgtga cacggactca agtgggctgg    4440
tgacccagtc agagttgtgc acatggctta gttttcatac acagcctggg ctggggtgg     4500 ggtgggagag gtcttttta aaaggaagtt actgttatag agggtctaag attcatccat     4560
ttatttggca tctgtttaaa gtagattaga tcttttaagc ccatcaatta tagaaagcca    4620
aatcaaaata tgttgatgaa aaatagcaac cttttatct ccccttcaca tgcatcaagt     4680
tattgacaaa ctctccctc actccgaaag ttccttatgt atatttaaaa gaaagcctca     4740
gagaattgct gattcttgag tttagtgatc tgaacagaaa taccaaaatt atttcagaaa    4800
tgtacaactt tttacctagt acaaggcaac atataggttg taaatgtgtt taaaacaggt    4860
ctttgtcttg ctatggggag aaaagacatg aatatgatta gtaaagaaat gacactttc     4920 atgtgtgatt tcccctccaa ggtatggtta ataagtttca ctgacttaga accaggcgag    4980
agacttgtgg cctgggagag ctggggaagc ttcttaaatg agaaggaatt tgagttggat    5040
catctattgc tggcaaagac agaagcctca ctgcaagcac tgcatgggca agcttggctg    5100
tagaaggaga cagagctggt tgggaagaca tggggaggaa ggacaaggct agatcatgaa    5160
gaaccttgac ggcattgctc cgtctaagtc atgagctgag cagggagatc ctggttggtg    5220
ttgcagaagg tttactctgt ggccaaagga gggtcaggaa ggatgagcat ttagggcaag    5280
gagaccacca acagccctca ggtcagggtg aggatggcct ctgctaagct caaggcgtga    5340
ggatgggaag gagggaggta ttcgtaagga tgggaaggag ggaggtattc gtgcagcata    5400
tgaggatgca gagtcagcag aactggggtg gatttgggtt ggaagtgagg gtcagagagg    5460
agtcagagag aatccctagt cttcaagcag attggagaaa cccttgaaaa gacatcaagc    5520
acagaaggag gaggaggagg tttaggtcaa gaagaagatg gattggtgta aaggatggg     5580 tctggtttgc agagcttgaa cacagtctca cccagactcc aggctgtctt tcactgaatg    5640
cttctgactt catagatttc cttcccatcc cagctgaaat actgagggt ctccaggagg      5700 agactagatt tatgaataca cgaggtatga ggtctaggaa catacttcag ctcacacatg    5760
agatctaggt gaggattgat tacctagtag tcatttcatg ggttgttggg aggattctat    5820
gaggcaacca caggcagcat ttagcacata ctacacattc aataagcatc aaactcttag    5880
ttactcattc agggatagca ctgagcaaag cattgagcaa aggggtccca tagaggtgag    5940
ggaagcctga aaactaaga tgctgcctgc ccagtgcaca caagtgtagg tatcattttc      6000
tgcatttaac cgtcaatagg caaaggggg aagggacata ttcatttgga aataagctgc      6060
cttgagcctt aaaacccaca aaagtacaat ttaccagcct ccgtatttca gactgaatgg    6120
gggtgggggg ggcgccttag gtacttattc cagatgcctt ctccagacaa accagaagca    6180
acagaaaaaa tcgtctctcc ctcccttga aatgaatata ccccttagtg tttgggtata     6240
ttcatttcaa agggagagag agaggttttt ttctgttctg tctcatatga ttgtgcacat    6300
acttgagact gttttgaatt tgggggatgg ctaaaccat catagtacag gtaaggtgag     6360
ggaatagtaa gtggtgagaa ctactcaggg aatgaaggtg tcagaataat aagaggtgct    6420
actgactttc tcagcctctg aatatgaacg gtgagcattg tggctgtcag caggaagcaa    6480
cgaagggaaa tgtcttttcct tttgctctta agttgtggag agtgcaacag tagcatagga   6540
ccctaccctc tgggccaagt caaagacatt ctgcatctt agtatttgca tattcttatg     6600
tatgtgaaag ttacaaattg cttgaaagaa aatatgcatc taataaaaaa cacctttctaa  6660
```

-continued

```
aataattcat tatattcttg ctctttcagt caagtgtaca tttagagaat agcacataaa    6720
actgccagag cattttataa gcagctgttt tcttccttag tgtgtgtgca tgtgtgtgtg    6780
atgtatacaa agagagagat aattgtattt ttgtattttc ttttaaataa ttttttaaaat   6840 tgaccctttt cctgagacaa attgccagaa tagtttgtat ttagagatgg tacctctaag    6900
agtaaggttg ctggttgctg agcaattgac ttgaaaactt ttaaaattca aattttaatt    6960
ccactactca aaagaattgc catgttttaa aaaagagaat tggtgccata agttagttgt    7020
ctatgtttga aaatgaagaa gatatgcaac gtcatggcct ggtcacttac ccgcagccct    7080
gagttgtagg cacatcatat gtgagaatga ggatgctttt ctttcattta aaatccctcc    7140
ccaaaacttg gctctaattg cagtcatgac aatcatgtac atttggattt atgtgcacga    7200
gtctcttacc ctgagagagg acaggtgcta caggtggagg ggacccgtct gggtcacgtt    7260
cacat                                                                7265
```

<210> SEQ ID NO 21
<211> LENGTH: 352
<212> TYPE: PRT
<213> ORGANISM: homo sapiens
<220> FEATURE:
<223> OTHER INFORMATION: chemokine (C-C motif) receptor 5

<400> SEQUENCE: 21

```
Met Asp Tyr Gln Val Ser Ser Pro Ile Tyr Asp Ile Asn Tyr Tyr Thr
  1               5                  10                  15

Ser Glu Pro Cys Gln Lys Ile Asn Val Lys Gln Ile Ala Ala Arg Leu
             20                  25                  30

Leu Pro Pro Leu Tyr Ser Leu Val Phe Ile Phe Gly Phe Val Gly Asn
         35                  40                  45

Met Leu Val Ile Leu Ile Leu Ile Asn Cys Lys Arg Leu Lys Ser Met
     50                  55                  60

Thr Asp Ile Tyr Leu Leu Asn Leu Ala Ile Ser Asp Leu Phe Phe Leu
 65                  70                  75                  80

Leu Thr Val Pro Phe Trp Ala His Tyr Ala Ala Ala Gln Trp Asp Phe
                 85                  90                  95

Gly Asn Thr Met Cys Gln Leu Leu Thr Gly Leu Tyr Phe Ile Gly Phe
            100                 105                 110

Phe Ser Gly Ile Phe Phe Ile Ile Leu Leu Thr Ile Asp Arg Tyr Leu
        115                 120                 125

Ala Val Val His Ala Val Phe Ala Leu Lys Ala Arg Thr Val Thr Phe
    130                 135                 140

Gly Val Val Thr Ser Val Ile Thr Trp Val Val Ala Val Phe Ala Ser
145                 150                 155                 160

Leu Pro Gly Ile Ile Phe Thr Arg Ser Gln Lys Glu Gly Leu His Tyr
                165                 170                 175

Thr Cys Ser Ser His Phe Pro Tyr Ser Gln Tyr Gln Phe Trp Lys Asn
            180                 185                 190

Phe Gln Thr Leu Lys Ile Val Ile Leu Gly Leu Val Leu Pro Leu Leu
        195                 200                 205

Val Met Val Ile Cys Tyr Ser Gly Ile Leu Lys Thr Leu Leu Arg Cys
    210                 215                 220

Arg Asn Glu Lys Lys Arg His Arg Ala Val Arg Leu Ile Phe Thr Ile
225                 230                 235                 240

Met Ile Val Tyr Phe Leu Phe Trp Ala Pro Tyr Asn Ile Val Leu Leu
```

```
                       245                 250                 255
Leu Asn Thr Phe Gln Glu Phe Phe Gly Leu Asn Asn Cys Ser Ser Ser
                260                 265                 270

Asn Arg Leu Asp Gln Ala Met Gln Val Thr Glu Thr Leu Gly Met Thr
            275                 280                 285

His Cys Cys Ile Asn Pro Ile Ile Tyr Ala Phe Val Gly Glu Lys Phe
290                 295                 300

Arg Asn Tyr Leu Leu Val Phe Phe Gln Lys His Ile Ala Lys Arg Phe
305                 310                 315                 320

Cys Lys Cys Cys Ser Ile Phe Gln Gln Glu Ala Pro Glu Arg Ala Ser
                325                 330                 335

Ser Val Tyr Thr Arg Ser Thr Gly Glu Gln Glu Ile Ser Val Gly Leu
            340                 345                 350

<210> SEQ ID NO 22
<211> LENGTH: 90
<212> TYPE: DNA
<213> ORGANISM: artificial sequence
<220> FEATURE:
<223> OTHER INFORMATION: Region comprising CCR5_S08 target

<400> SEQUENCE: 22
ttctgggctc cctacaacat tgtccttctc ctgaacacct tccaggaatt ctttggcctg    60
aataattgca gtagctctaa caggttggac                                     90

<210> SEQ ID NO 23
<211> LENGTH: 30
<212> TYPE: PRT
<213> ORGANISM: artificial sequence
<220> FEATURE:
<223> OTHER INFORMATION: Region comprising CCR5_S08 target

<400> SEQUENCE: 23

Phe Trp Ala Pro Tyr Asn Ile Val Leu Leu Leu Asn Thr Phe Gln Glu
1               5                   10                  15

Phe Phe Gly Leu Asn Asn Cys Ser Ser Ser Asn Arg Leu Asp
            20                  25                  30

<210> SEQ ID NO 24
<211> LENGTH: 8601
<212> TYPE: DNA
<213> ORGANISM: artificial sequence
<220> FEATURE:
<223> OTHER INFORMATION: CCR5_S08 LHE Trex2 lentiviral vector

<400> SEQUENCE: 24
gacgtcaatg tagtcttatg caatactctt gtagtcttgc aacatggtaa cgatgagtta    60
gcaacatgcc ttacaaggag agaaaaagca ccgtgcatgc cgattggtgg aagtaaggtg   120
gtacgatcgt gccttattag gaaggcaaca cgggtctg acatggattg gacgaaccac     180
tgaattgccg cattgcagag atattgtatt taagtgccta gctcgataca taaacgggtc   240
tctctggtta gaccagatct gagcctggga gctctctggc taactaggga acccactgct   300
taagcctcaa taaagcttgc cttgagtgct tcaagtagtg tgtgcccgtc tgttgtgtga   360
ctctggtaac tagagatccc tcagaccctt ttagtcagtg tggaaaatct ctagcagtgg   420
cgcccgaaca gggacttgaa agcgaaaggg aaaccagagg agctctctcg acgcaggact   480
cggcttgctg aagcgcgcac ggcaagaggc gaggggcggc gactggtgag tacgccaaaa   540
attttgacta gcggaggcta aggagagaga gatgggtgcg agagcgtcag tattaagcgg   600
```

| | |
|---|---|
| gggagaatta gatcgcgatg ggaaaaaatt cggttaaggc caggggggaaa gaaaaaatat | 660 |
| aaattaaaac atatagtatg ggcaagcagg gagctagaaa gattcgcagt taatcctggc | 720 |
| ctgttagaaa catcagaagg ctgtagacaa atactgggac agctacaacc atcccttcag | 780 |
| acaggatcag aagaacttag atcattatat aatacagtag caaccctcta ttgtgtgcat | 840 |
| caaaggatag agataaaaga caccaaggaa gctttagaca agatagagga gagcaaaac | 900 |
| aaaagtaaga ccaccgcaca gcaagcggcc ctgatcttca gacctggagg aggagatatg | 960 |
| agggacaatt ggagaagtga attatataaa tataaagtag taaaaattga accattagga | 1020 |
| gtagcaccca ccaaggcaaa gagaagagtg gtgcagagag aaaaaagagc agtgggaata | 1080 |
| ggagctttgt tccttgggtt cttgggagca gcaggaagca ctatgggcgc agcgtcaatg | 1140 |
| acgctgacgg tacaggccag acaattattg tctggtatag tgcagcagca gaacaatttg | 1200 |
| ctgagggcta ttgaggcgca acagcatctg ttgcaactca cagtctgggg catcaagcag | 1260 |
| ctccaggcaa gaatcctggc tgtggaaaga tacctaaagg atcaacagct cctggggatt | 1320 |
| tggggttgct ctggaaaact catttgcacc actgctgtgc cttggaatgc tagttggagt | 1380 |
| aatgaatctc tggaacagat ttggaatcac acgacctgga tggagtggga cagagaaatt | 1440 |
| aacaattaca caagcttaat acactcctta attgaagaat cgcaaaacca gcaagaaaag | 1500 |
| aatgaacaag aattattgga attagataaa tgggcaagtt tgtggaattg gtttaacata | 1560 |
| acaaattggc tgtggtatat aaaattattc ataatgatag taggaggctt ggtaggttta | 1620 |
| agaatagttt ttgctgtact ttctatagtg aatagagtta ggcagggata ttcaccatta | 1680 |
| tcgtttcaga cccacctccc aaccccgagg ggacccgaca ggcccgaagg aatagaagaa | 1740 |
| gaaggtggag agagacag agacagatcc attcgattag tgaacggatc tcgacggtat | 1800 |
| cggttaactt ttaaaagaaa aggggggatt ggggggtaca gtgcagggga agaatagta | 1860 |
| gacataatag caacagacat acaaactaaa gaattacaaa aacaaattac aaaaattcaa | 1920 |
| aattttatcg attacgcgtc acgtgctagc tgcagtaacg ccattttgca aggcatggaa | 1980 |
| aaataccaaa ccaagaatag agaagttcag atcaagggcg ggtacatgaa aatagctaac | 2040 |
| gttgggccaa acaggatatc tgcggtgagc agtttcggcc ccggcccggg gccaagaaca | 2100 |
| gatggtcacc gcagtttcgg ccccggcccg aggccaagaa cagatggtcc ccagatatgg | 2160 |
| cccaaccctc agcagtttct taagacccat cagatgtttc caggctcccc caaggacctg | 2220 |
| aaatgaccct gcgccttatt tgaattaacc aatcagcctg cttctcgctt ctgttcgcgc | 2280 |
| gcttctgctt cccgagctct ataaagagc tcacaacccc tcactcggcg cgccagtcct | 2340 |
| ccgacagact gagtcgcccg ctcgagccgc caccatggga tatccatacg atgtcccaga | 2400 |
| ttatgcgcca cctaagaaga aacgcaaagt cacgcgatcg cgcagagagt ccatcaaccc | 2460 |
| atggattctg actggtttca ctgatgccga aggatcattc atgctaagaa tccgtaacac | 2520 |
| gaacaaccgg tcagtagggt actacacttc actggtattc gaaatcactc tgcacaacaa | 2580 |
| ggacaaatcg attctggaga atatccagtc gacttggaag gtcggcacaa tcaacaaccg | 2640 |
| aggcgacggc accgccagac tgagcgtcac tcgtttcgaa gatttgaaag tgattatcga | 2700 |
| ccacttcgag aaatatccgc tgattaccca gaaattgggc gattacaagt tgtttaaaca | 2760 |
| ggcgttcagc gtcatggaga acaaagaaca tcttaaggag aatgggatta aggagctcgt | 2820 |
| acgaatcaaa gctaagatga attggggtct cactgacgaa ttgaaaaaag catttccaga | 2880 |
| gaacattagc aaagagcgcc cccttatcaa taagaacatt ccgaatctca aatggctggc | 2940 |

```
tggattcaca tctggtgaag gcacattcta cgtgcaccta gcaaagtctg aagctagcgg    3000
caaggtatac gtgcgactga ggttcataat cggccagcac atcagagaca agaacctgat    3060
gaattcattg ataacatacc taggctgtgg taagatccag gagaagaaca ggtctgaggg    3120
cagtatgctc cacttcatag taactaaatt cagcgatatc aacgacaaga tcattccggt    3180
attccaggaa aatactctga ttggcgtcaa actcgaggac tttgaagatt ggtgcaaggt    3240
tgccaaattg atcgaagaga agaaacacct gaccgaatcc ggtttggatg agattaagaa    3300
aatcaagctg aacatgaaca aaggtcgtgt cttcagcggc cgctccggtg agggcagagg    3360
aagtcttcta acatgcggtg acgtggagga gaatccgggc ccctccggat ctgagccacc    3420
tcgggctgag acctttgtat tcctggacct agaagccact gggctcccaa acatggaccc    3480
tgagattgca gagatatccc tttttgctgt tcaccgctct tccctggaga cccagaacg    3540 ggatgattct ggttccttgg tgctgccccg tgttctggac aagctcacac tgtgcatgtg    3600
cccggagcgc ccctttactg ccaaggccag tgagattact ggtttgagca gcgaaagcct    3660
gatgcactgc gggaaggctg gtttcaatgg cgctgtggta aggacactgc agggcttcct    3720
aagccgccag gagggcccca tctgccttgt ggcccacaat ggcttcgatt atgacttccc    3780
actgctgtgc acggagctac aacgtctggg tgcccatctg ccccaagaca ctgtctgcct    3840
ggacacactg cctgcattgc ggggcctgga ccgtgctcac agccacggca ccagggctca    3900
aggccgcaaa agctacagcc tggcagtctc cttccaccgc tacttccagg ctgaacccag    3960
tgctgcccat tcagcagaag gtgatgtgca caccctgctt ctgatcttcc tgcatcgtgc    4020
tcctgagctg ctcgcctggg cagatgagca ggcccgcagc tgggctcata ttgagcccat    4080
gtacgtgcca cctgatggtc caagcctcga agcctgacct gcaggtcgag catgcatcta    4140
gggcggccaa ttccgcccct ctccccccc ccctctccc tcccccccc ctaacgttac    4200 tggccgaagc cgcttggaat aaggccggtg tgcgtttgtc tatatgttat tttccaccat    4260
attgccgtct tttggcaatg tgagggcccg gaaacctggc cctgtcttct tgacgagcat    4320
tcctaggggt cttttcccctc tcgccaaagg aatgcaaggt ctgttgaatg tcgtgaagga    4380
agcagttcct ctggaagctt cttgaagaca acaacgtct gtagcgaccc tttgcaggca    4440 gcggaaccccc ccacctggcg acaggtgcct ctgcggccaa aagccacgtg tataagatac    4500
acctgcaaag gcggcacaac cccagtgcca cgttgtgagt tggatagttg tggaaagagt    4560
caaatggctc tcctcaagcg tattcaacaa ggggctgaag gatgcccaga aggtacccca    4620
ttgtatggga tctgatctgg ggcctcggtg cacatgcttt acatgtgttt agtcgaggtt    4680
aaaaaaacgt ctaggccccc cgaaccacgg ggacgtggtt ttccttttgaa aaacacgatg    4740 ataagcttgc cacaacccctt accggtcgcc accatgagcg agctgattaa ggagaacatg    4800
cacatgaagc tgtacatgga gggcaccgtg gacaaccatc acttcaagtg cacatccgag    4860
ggcgaaggca gcccctacga gggcacccag accatgagaa tcaaggtggt cgagggcggc    4920 cctctccccct tcgccttcga catcctggct actagcttcc tctacggcag caagaccttc    4980
atcaaccaca cccagggcat ccccgacttc ttcaagcagt ccttccctga gggcttcaca    5040
tgggagagag tcaccacata cgaagacggg ggcgtgctga ccgctaccca ggacaccagc    5100
ctccaggacg gctgcctcat ctacaacgtc aagatcagag gggtgaactt cacatccaac    5160
ggccctgtga tgcagaagaa aacactcggc tgggaggcct tcaccgagac gctgtacccc    5220
gctgacggcg gcctggaagg cagaaacgac atggcccctga agctcgtggg cgggagccat    5280
ctgatcgcaa acatcaagac cacatataga tccaagaaac ccgctaagaa cctcaagatg    5340
```

```
cctggcgtct actatgtgga ctacagactg gaaagaatca aggaggccaa caacgagacc    5400
tacgtcgagc agcacgaggt ggcagtggcc agatactgcg acctccctag caaactgggg    5460
cacaagctta attgattcta gagtcgaccg agcatcttac cgccatttat acccatattt    5520
gttctgtttt tcttgatttg ggtatacatt taaatgttaa tagaacaaaa tggtggggca    5580
atcatttaca ttttagggga tatgtaatta ctagttcagg tgtattgcca caagacaaac    5640
atgttaagaa actttcccgt tatttacgct ctgttcctgt taatcaacct ctggattaca    5700
aaatttgtga agattgact  gatattctta actatgttgc tccttttacg ctgtgtggat    5760
atgctgcttt atagcctctg tatctagcta ttgcttcccg tacggctttc gttttctcct    5820
ccttgtataa atcctggttg ctgtctcttt tagaggagtt gtggcccgtt gtccgtcaac    5880
gtggcgtggt gtgctctgtg tttgctgacg caacccccac tggctgggc  attgccacca    5940 cctgtcaact cctttctggg actttcgctt tccccctccc gatcgccacg gcagaactca    6000
tcgccgcctg ccttgcccgc tgctggacag gggctaggtt gctgggcact gataattccg    6060
tggtgttgtc atcggtacct ttttaaaaga aagggggga  ctggaagggc taattcactc    6120
ccaacgaaga caagatatca taacttcgta tagcatacat tatacgaagt tataatttat    6180
ttgtgaaatt tgtgatgcta ttgctttatt tgtaaccata tgtttatttg tgaaatttgt    6240
gatgctattg ctttatttgt aaccattgct ttttgcttgt actgggtctc tctggttaga    6300
ccagatctga gcctgggagc tctctggcta actagggaac ccactgctta agcctcaata    6360
aagcttgcct cgaccagcct cgactgtgcc ttctagttgc cagccatctg ttgtttgccc    6420
ctcccccgtg ccttccttga ccctggaagg tgccactccc actgtccttt cctaataaaa    6480
tgaggaaatt gcatcgcatt gtctgagtag gtgtcattct attctggggg gtggggtggg    6540
gcaggacagc aagggggagg attgggaaga caatagcagg catgctgggg atgcggtggg    6600
ctctatggcc tgcagctgca ttaatgaatc ggccaacgcg cggggagagg cggtttgcgt    6660
attgggcgct cttccgcttc ctcgctcact gactcgctgc gctcggtcgt tcggctgcgg    6720
cgagcggtat cagctcactc aaaggcggta atacggttat ccacagaatc agggggataac    6780 gcaggaaaga acatgtgagc aaaaggccag caaaaggcca ggaaccgtaa aaaggccgcg    6840
ttgctggcgt ttttccatag gctccgcccc cctgacgagc atcacaaaaa tcgacgctca    6900
agtcagaggt ggcgaaaccc gacaggacta taaagatacc aggcgtttcc ccctggaagc    6960
tccctcgtgc gctctcctgt tccgaccctg ccgcttaccg gatacctgtc cgcctttctc    7020
ccttcgggaa gcgtggcgct ttctcatagc tcacgctgta ggtatctcag ttcggtgtag    7080
gtcgttcgct ccaagctggg ctgtgtgcac gaaccccccg ttcagcccga ccgctgcgcc    7140
ttatccggta actatcgtct tgagtccaac ccggtaagac acgacttatc gccactggca    7200
gcagccactg gtaacaggat tagcagagcg aggtatgtag gcggtgctac agagttcttg    7260
aagtggtggc ctaactacgg ctacactaga aggacagtat ttggtatctg cgctctgctg    7320
aagccagtta ccttcggaaa aagagttggt agctcttgat ccggcaaaca aaccaccgct    7380
ggtagcggtg ttttttttgt ttgcaagcag cagattacgc gcagaaaaaa aggatctcaa    7440
gaagatcctt tgatctttc  tacggggtct gacgctcagt ggaacgaaaa ctcacgttaa    7500
gggattttgg tcatgagatt atcaaaaagg atcttcacct agatcctttt aaattaaaaa    7560
tgaagtttta aatcaatcta agtatatat  gagtaaactt ggtctgacag ttaccaatgc    7620
ttaatcagtg aggcacctat ctcagcgatc tgtctatttc gttcatccat agttgcctga    7680
```

```
ctccccgtcg tgtagataac tacgatacgg gagggcttac catctggccc cagtgctgca    7740
atgataccgc gagacccacg ctcaccggct ccagatttat cagcaataaa ccagccagcc    7800
ggaagggccg agcgcagaag tggtcctgca actttatccg cctccatcca gtctattaat    7860
tgttgccggg aagctagagt aagtagttcg ccagttaata gtttgcgcaa cgttgttgcc    7920
attgctacag gcatcgtggt gtcacgctcg tcgtttggta tggcttcatt cagctccggt    7980
tcccaacgat caaggcgagt tacatgatcc cccatgttgt gcaaaaaagc ggttagctcc    8040
ttcggtcctc cgatcgttgt cagaagtaag ttggccgcag tgttatcact catggttatg    8100
gcagcactgc ataattctct tactgtcatg ccatccgtaa gatgcttttc tgtgactggt    8160
gagtactcaa ccaagtcatt ctgagaatag tgtatgcggc gaccgagttg ctcttgcccg    8220
gcgtcaatac gggataatac cgcgccacat agcagaactt taaaagtgct catcattgga    8280
aaacgttctt cggggcgaaa actctcaagg atcttaccgc tgttgagatc cagttcgatg    8340
taacccactc gtgcacccaa ctgatcttca gcatctttta ctttcaccag cgtttctggg    8400
tgagcaaaaa caggaaggca aaatgccgca aaaaagggaa taagggcgac acggaaatgt    8460
tgaatactca tactcttcct ttttcaatat tattgaagca tttatcaggg ttattgtctc    8520
atgagcggat acatatttga atgtatttag aaaaataaac aataggggt tccgcgcaca    8580 tttccccgaa aagtgccacc t                                             8601
```

<210> SEQ ID NO 25
<211> LENGTH: 887
<212> TYPE: PRT
<213> ORGANISM: artificial sequence
<220> FEATURE:
<223> OTHER INFORMATION: MegaTal CCR5_S08

<400> SEQUENCE: 25

```
Met Gly Ser Cys Arg Tyr Pro Tyr Asp Val Pro Asp Tyr Ala Pro Pro
1               5                   10                  15

Lys Lys Lys Arg Lys Val Val Asp Leu Arg Thr Leu Gly Tyr Ser Gln
            20                  25                  30

Gln Gln Gln Glu Lys Ile Lys Pro Lys Val Arg Ser Thr Val Ala Gln
        35                  40                  45

His His Glu Ala Leu Val Gly His Gly Phe Thr His Ala His Ile Val
    50                  55                  60

Ala Leu Ser Gln His Pro Ala Ala Leu Gly Thr Val Ala Val Thr Tyr
65                  70                  75                  80

Gln His Ile Ile Thr Ala Leu Pro Glu Ala Thr His Glu Asp Ile Val
                85                  90                  95

Gly Val Gly Lys Gln Trp Ser Gly Ala Arg Ala Leu Glu Ala Leu Leu
            100                 105                 110

Thr Asp Ala Gly Glu Leu Arg Gly Pro Pro Leu Gln Leu Asp Thr Gly
        115                 120                 125

Gln Leu Val Lys Ile Ala Lys Arg Gly Gly Val Thr Ala Met Glu Ala
    130                 135                 140

Val His Ala Ser Arg Asn Ala Leu Thr Gly Ala Pro Leu Asn Leu Thr
145                 150                 155                 160

Pro Asp Gln Val Val Ala Ile Ala Ser Asn Asn Gly Gly Lys Gln Ala
                165                 170                 175

Leu Glu Thr Val Gln Arg Leu Leu Pro Val Leu Cys Gln Asp His Gly
            180                 185                 190

Leu Thr Pro Asp Gln Val Val Ala Ile Ala Ser Asn Gly Gly Gly Lys
```

```
                195                 200                 205
Gln Ala Leu Glu Thr Val Gln Arg Leu Leu Pro Val Leu Cys Gln Asp
210                 215                 220
His Gly Leu Thr Pro Asp Gln Val Val Ala Ile Ala Ser His Asp Gly
225                 230                 235                 240
Gly Lys Gln Ala Leu Glu Thr Val Gln Arg Leu Leu Pro Val Leu Cys
                245                 250                 255
Gln Asp His Gly Leu Thr Pro Asp Gln Val Val Ala Ile Ala Ser His
            260                 265                 270
Asp Gly Gly Lys Gln Ala Leu Glu Thr Val Gln Arg Leu Leu Pro Val
            275                 280                 285
Leu Cys Gln Asp His Gly Leu Thr Pro Asp Gln Val Val Ala Ile Ala
        290                 295                 300
Ser Asn Gly Gly Gly Lys Gln Ala Leu Glu Thr Val Gln Arg Leu Leu
305                 310                 315                 320
Pro Val Leu Cys Gln Asp His Gly Leu Thr Pro Asp Gln Val Val Ala
                325                 330                 335
Ile Ala Ser Asn Gly Gly Gly Lys Gln Ala Leu Glu Thr Val Gln Arg
            340                 345                 350
Leu Leu Pro Val Leu Cys Gln Asp His Gly Leu Thr Pro Asp Gln Val
            355                 360                 365
Val Ala Ile Ala Ser His Asp Gly Gly Lys Gln Ala Leu Glu Thr Val
        370                 375                 380
Gln Arg Leu Leu Pro Val Leu Cys Gln Asp His Gly Leu Thr Pro Asp
385                 390                 395                 400
Gln Val Val Ala Ile Ala Ser Asn Gly Gly Gly Lys Gln Ala Leu Glu
                405                 410                 415
Thr Val Gln Arg Leu Leu Pro Val Leu Cys Gln Asp His Gly Leu Thr
            420                 425                 430
Pro Asp Gln Val Val Ala Ile Ala Ser His Asp Gly Gly Lys Gln Ala
            435                 440                 445
Leu Glu Thr Val Gln Arg Leu Leu Pro Val Leu Cys Gln Asp His Gly
        450                 455                 460
Leu Thr Pro Asp Gln Val Val Ala Ile Ala Ser His Asp Gly Gly Lys
465                 470                 475                 480
Gln Ala Leu Glu Thr Val Gln Arg Leu Leu Pro Val Leu Cys Gln Asp
                485                 490                 495
His Gly Leu Thr Pro Asp Gln Val Val Ala Ile Ala Ser Asn Gly Gly
            500                 505                 510
Gly Lys Gln Ala Leu Glu Ser Ile Val Ala Gln Leu Ser Arg Pro Asp
            515                 520                 525
Pro Ala Leu Ala Ala Leu Thr Asn Asp His Leu Val Ala Leu Ala Cys
        530                 535                 540
Leu Gly Gly Arg Pro Ala Met Asp Ala Val Lys Lys Gly Leu Pro His
545                 550                 555                 560
Ala Pro Glu Leu Ile Arg Arg Val Asn Arg Arg Ile Gly Glu Arg Thr
                565                 570                 575
Ser His Arg Val Ala Ile Ser Arg Val Gly Gly Ser Ser Arg Arg Glu
            580                 585                 590
Ser Ile Asn Pro Trp Ile Leu Thr Gly Phe Thr Asp Ala Glu Gly Ser
        595                 600                 605
Phe Met Leu Arg Ile Arg Asn Thr Asn Asn Arg Ser Val Gly Tyr Tyr
        610                 615                 620
```

Thr Ser Leu Val Phe Glu Ile Thr Leu His Asn Lys Asp Lys Ser Ile
625                 630                 635                 640

Leu Glu Asn Ile Gln Ser Thr Trp Lys Val Gly Thr Ile Asn Asn Arg
        645                 650                 655

Gly Asp Gly Thr Ala Arg Leu Ser Val Thr Arg Phe Glu Asp Leu Lys
            660                 665                 670

Val Ile Ile Asp His Phe Glu Lys Tyr Pro Leu Ile Thr Gln Lys Leu
                675                 680                 685

Gly Asp Tyr Lys Leu Phe Lys Gln Ala Phe Ser Val Met Glu Asn Lys
690                 695                 700

Glu His Leu Lys Glu Asn Gly Ile Lys Glu Leu Val Arg Ile Lys Ala
705                 710                 715                 720

Lys Met Asn Trp Gly Leu Asn Asp Glu Leu Lys Lys Ala Phe Pro Glu
                725                 730                 735

Asn Ile Ser Lys Glu Arg Pro Leu Ile Asn Lys Asn Ile Pro Asn Leu
                740                 745                 750

Lys Trp Leu Ala Gly Phe Thr Ser Gly Glu Gly Thr Phe Tyr Val His
                755                 760                 765

Leu Ala Lys Ser Glu Ala Ser Gly Lys Val Tyr Val Arg Leu Arg Phe
770                 775                 780

Ile Ile Gly Gln His Ile Arg Asp Lys Asn Leu Met Asn Ser Leu Ile
785                 790                 795                 800

Thr Tyr Leu Gly Cys Gly Thr Ile Gln Glu Lys Asn Arg Ser Lys Gly
                805                 810                 815

Ser Met Leu His Phe Ile Val Thr Lys Phe Ser Asp Ile Asn Asp Lys
                820                 825                 830

Ile Ile Pro Val Phe Gln Glu Asn Thr Leu Ile Gly Val Lys Leu Glu
            835                 840                 845

Asp Phe Glu Asp Trp Cys Lys Val Ala Lys Leu Ile Glu Gly Lys Lys
850                 855                 860

His Leu Thr Glu Ser Gly Leu Asp Glu Ile Lys Lys Ile Lys Leu Asn
865                 870                 875                 880

Met Asn Lys Gly Arg Val Phe
                885

<210> SEQ ID NO 26
<211> LENGTH: 2661
<212> TYPE: RNA
<213> ORGANISM: artificial sequence
<220> FEATURE:
<223> OTHER INFORMATION: MegaTal CCR5_S08

<400> SEQUENCE: 26
augggauccu gcagguaucc auaugaugu ccagauuaug cgccaccuaa gaagaaacgc    60 aaagucugg aucuacgcac gcucggcuac agucagcagc agcaagagaa gaucaaaccg   120
aaggugcguu cgacagugg gcagcaccac gaggcacugg ugggccaugg guuuacacac   180
gcgcacaucg uugcgcucag ccaacacccg gcagcguuag ggaccgucgc ugucacguau   240
cagcacauaa ucacggcguu gccagaggcg acacacgaag acaucguugg cgucggcaaa   300 caguguccg gcgcacgcgc ccuggaggcc uugcucacgg augcggggga guugagaggu   360
ccgccguuac aguuggacac aggccaacuu ugaagauug caaaacgugg cggcgugacc   420
gcaauggagg cagucaugc aucgcgcaau gcacugacgg ugcccccccu gaaccugacc   480
ccggaccaag ugguggcuau cgccagcaac aauggcggca agcaagcgcu cgaaacgguc   540

```
cagcggcugu ugccggugcu gugccaggac cauggccuga ccccggacca agugguggcu    600
aucgccagca acgguggcgg caagcaagcg cucgaaacgg ugcagcggcu guugccggug    660
cugugccagg accauggccu gacuccggac caaguggugg cuaucgccag ccacgauggc    720
ggcaagcaag cgcucgaaac ggugcagcgg cguugccggu gcugugccag gaccauggc    780 cugacuccgg accaaguggu ggcuaucgcc agccacgaug cggcaagca agcgcucgaa    840 acggugcagc ggcuguugcc ggugcugugc caggaccaug gccgaccccc ggaccaagug    900
guggcuaucg ccagcaacgg uggcggcaag caagcgcucg aaacggugca gcggcuguug    960
ccggugcugu gccaggacca uggccugacc cggaccaag uggugcuau cgccagcaac    1020 gguggcggca agcaagcgcu cgaaacggug cagcggcugu ugccggugcu gugccaggac    1080
cauggccuga cuccggacca aguggugcu aucgccagcc acgauggcgg caagcaagcg    1140
cucgaaacgg ugcagcggcu guugccggug cugugccagg accauggccu gaccccggac    1200
caaguggugu cuaucgccag caacgguggc ggcaagcaag cgcucgaaac ggugcagcgg    1260
cguugccggu gcugugcca ggaccauggc cugacuccgg accaaguggu ggcuaucgcc    1320
agccacgaug cggcaagca agcgcucgaa acggugcagc ggcuguugcc ggugcugugc    1380
caggaccaug gccgaccccc ggaccaagug guggcuaucg ccagcacga uggcggcaag    1440 caagcgcucg aaacggugca gcggcuguug ccggugcugu gccaggacca uggccugacc    1500
ccggaccaag uggugcuau cgccagcaac gguggcggca agcaagcgcu cgaaagcauu    1560
guggcccagc ugagccggcc ugauccggcg uggccgcgu ugaccaacga ccaccucguc    1620
gccuuggccu gccucggcgg acguccugcc auggaugcag ugaaaaaggg auugccgcac    1680
gcgccggaau ugaucagaag agucaaucgc cguauuggcg aacgcacguc ccaucgcguu    1740
gcgauaucua gagugggagg aagcucucgc agagaguccca ucaacccaug gauucugacu    1800
gguuucacug augccgaagg aucauucaug cuaagaaucc guaacacgaa caaccgguca    1860 guagggguacu acacuucacu gguauucgaa ucacucugc acaacaagga caaaucgauu    1920
cuugagaaua uccagucgac uuggaagguc ggcacaauca acaaccgagg cgacggcacc    1980
gccagacuga gcgucacucg uuucgaagau uugaaaguga uuaucgacca cuucgagaaa    2040
uauccgcuga uuacccagaa auugggggcau acaaguugu uuaaacaggc auucagcguc    2100
auggagaaca agaacaucu uaaggagaau gggauuaagg agcucguacg aaucaaagcu    2160
aagaugaauu ggggucucaa ugacgaauug aaaaaagcau uccagagaa caucagcaaa    2220 gagcgccccc uuaucaauaa gaacauuccg aaucucaaau ggcuggcugg auucacaucu    2280
ggugaaggca cauucuacgu gcaccuagca aagucugaag cuagcggcaa gguauacgug    2340
cgacugaggu ucauaaucgg ccagcacauc agagacaaga accugaugaa ucauugaua    2400 acauaccuag gcugugguac gauccaggag aagaacaggu cuaagggcag uaugcuccac    2460
uucauaguaa cuaaauucag cgauaucaac gacaagauca uuccgguauu ccaggaaaau    2520
acucugauug gcgucaaacu cgaggacuuu gaagauuggu gcaagguugc caaauugauc    2580
gaagagaaga acaccugac cgaauccggu uuggaugaga uuaagaaaau caagcugaac    2640
augaacaaag gucgugucuu c                                              2661
```

<210> SEQ ID NO 27
<211> LENGTH: 9605
<212> TYPE: DNA
<213> ORGANISM: artificial sequence
<220> FEATURE:

<223> OTHER INFORMATION: MegaTAL CCR5_S08 LHE lentiviral vector

<400> SEQUENCE: 27

```
gacgtcaatg tagtcttatg caatactctt gtagtcttgc aacatggtaa cgatgagtta      60
gcaacatgcc ttacaaggag agaaaaagca ccgtgcatgc cgattggtgg aagtaaggtg     120
gtacgatcgt gccttattag gaaggcaaca gacgggtctg acatggattg gacgaaccac     180
tgaattgccg cattgcagag atattgtatt taagtgccta gctcgataca taaacgggtc     240
tctctggtta gaccagatct gagcctggga gctctctggc taactaggga acccactgct     300
taagcctcaa taaagcttgc cttgagtgct tcaagtagtg tgtgcccgtc tgttgtgtga     360
ctctggtaac tagagatccc tcagaccctt ttagtcagtg tggaaaatct ctagcagtgg     420
cgcccgaaca gggacttgaa agcgaaaggg aaaccagagg agctctctcg acgcaggact     480
cggcttgctg aagcgcgcac ggcaagaggc gaggggcggc gactggtgag tacgccaaaa     540
attttgacta gcggaggcta aaggagaga tgggtgcg agagcgtcag tattaagcgg     600
gggagaatta gatcgcgatg ggaaaaaatt cggttaaggc caggggaaaa gaaaaaatat     660
aaattaaaac atatagtatg ggcaagcagg gagctagaac gattcgcagt taatcctggc     720
ctgttagaaa catcagaagg ctgtagacaa atactggac agctacaacc atcccttcag     780
acaggatcag aagaacttag atcattatat aatacagtag caaccctcta ttgtgtgcat     840
caaaggatag agataaaaga caccaaggaa gctttagaca atagagga agagcaaaac     900
aaaagtaaga ccaccgcaca gcaagcggcc ctgatcttca gacctggagg aggagatatg     960
agggacaatt ggagaagtga attatataaa tataaagtag taaaaattga accattagga    1020
gtagcaccca ccaaggcaaa gagaagagtg gtgcagagag aaaaaagagc agtgggaata    1080
ggagctttgt tccttgggtt cttgggagca gcaggaagca ctatgggcgc agcgtcaatg    1140
acgctgacgg tacaggccag acaattattg tctggtatag tgcagcagca gaacaatttg    1200
ctgagggcta ttgaggcgca acagcatctg ttgcaactca cagtctgggg catcaagcag    1260
ctccaggcaa gaatcctggc tgtggaaaga tacctaaagg atcaacagct cctggggatt    1320
tggggttgct ctggaaaact catttgcacc actgctgtgc cttggaatgc tagttggagt    1380
aatgaatctc tggaacagat ttggaatcac acgacctgga tggagtggga cagagaaatt    1440
aacaattaca caagcttaat acactcctta attgaagaat cgcaaaacca gcaagaaaag    1500
aatgaacaag aattattgga attagataaa tgggcaagtt tgtggaattg gtttaacata    1560
acaaattggc tgtggtatat aaaattattc ataatgatag taggaggctt ggtaggttta    1620
agaatagttt ttgctgtact ttctatagtg aatagagtta ggcagggata ttcaccatta    1680
tcgtttcaga cccacctccc aaccccgagg ggacccgaca ggcccgaagg aatagaagaa    1740
gaaggtggag agagagacag agacagatcc attcgattag tgaacggatc tcgacggtat    1800
cggttaactt ttaaaagaaa aggggggatt ggggggtaca gtgcagggga agaatagta    1860
gacataatag caacagacat acaaactaaa gaattacaaa aacaaattac aaaaattcaa    1920
aattttatcg attacgcgtg tggcatctga agcaccacca gcgagcgaga gctagagaga    1980
aggaaagcca ccgacttcac cgcctccgag ctgctccggg tcgcgggtct gcagcgtcta    2040
cggccctccg cgcctacagc tcaagccaca tccgaagggg agggagccg ggagctgcgc    2100
gcggggccgc cggggggagg ggtggcaccg cccacgccgg gcggccacga agggcggggc    2160
agcgggcgcg cgcccggcgg ggggagggc cgcgcgccgc cccgctggg aattgggcc    2220
ctaggggag ggcggaggcg ccgacgaccg cggcacttac cgttcgcggc gtggcgcccg    2280
```

```
gtggtcccca aggggaggga aggggaggc ggggcgagga cagtgaccgg agtctcctca    2340
gcggtggctt ttctgcttgg cagcctcagc ggctggcgcc aaaaccggac tccgcccact    2400
tcctcgcccc tgcggtgcga gggtgtggaa tcctccagac gctggggag ggggagttgg     2460
gagcttaaaa actagtaccc ctttgggacc actttcagca gcgaactctc ctgtacacca    2520
ggggtcagtt ccacagacgc gggccagggg tgggtcattg cggcgtgaac aataatttga    2580
ctagaagttg attcgggtgt ttccggaatt cctagctgca gtaacgccat tttgcaaggc    2640
atggaaaaat accaaaccaa gaatagagaa gttcagatca agggcgggta catgaaaata    2700
gctaacgttg ggccaaacag gatatctgcg gtgagcagtt tcggccccgg cccgggcca     2760
agaacagatg gtcaccgcag tttcggcccc ggcccgaggc caagaacaga tggtccccag    2820
atatggccca accctcagca gtttcttaag acccatcaga tgtttccagg ctcccccaag    2880
gacctgaaat gaccctgcgc cttatttgaa ttaaccaatc agcctgcttc tcgcttctgt    2940
tcgcgcgctt ctgcttcccg agctctataa aagagctcac aacccctcac tcggcgcgcc    3000
taatacgact cactataggg gccgccacca tgggatcctg caggtatcca tatgatgtcc    3060
cagattatgc gccacctaag aagaaacgca agtcgtgga tctacgcacg ctcggctaca     3120
gtcagcagca gcaagagaag atcaaaccga aggtgcgttc gacagtggcg cagcaccacg    3180
aggcactggt gggccatggg tttacacacg cgcacatcgt tgcgctcagc caacacccgg    3240
cagcgttagg gaccgtcgct gtcacgtatc agcacataat cacggcgttg ccagaggcga    3300
cacacgaaga catcgttggc gtcggcaaac agtggtccgg cgcacgcgcc ctggaggcct    3360
tgctcacgga tgcgggggag ttgagaggtc gccgttaca gttggacaca ggccaacttg     3420
tgaagattgc aaaacgtggc ggcgtgaccg caatggaggc agtgcatgca tcgcgcaatg    3480
cactgacggg tgccccctg aacctgaccc cggaccaagt ggtggctatc gccagcaaca    3540
atggcggcaa gcaagcgctc gaaacggtgc agcggctgtt gccggtgctg tgccaggacc    3600
atggcctgac cccggaccaa gtggtggcta tcgccagcaa cggtggcggc aagcaagcgc    3660
tcgaaacggt gcagcggctg ttgccggtgc tgtgccagga ccatggcctg actccggacc    3720
aagtggtggc tatcgccagc cacgatggcg gcaagcaagc gctcgaaacg gtgcagcggc    3780
tgttgccggt gctgtgccag gaccatggcc tgactccgga ccaagtggtg gctatcgcca    3840
gccacgatgc cggcaagcaa gcgctcgaaa cggtgcagcg gctgttgccg gtgctgtgcc    3900
aggaccatgg cctgaccccg gaccaagtgg tggctatcgc cagcaacggt ggcggcaagc    3960
aagcgctcga aacggtgcag cggctgttgc cggtgctgtg ccaggaccat ggcctgaccc    4020
cggaccaagt ggtggctatc gccagcaacg gtggcggcaa gcaagcgctc gaaacggtgc    4080
agcggctgtt gccggtgctg tgccaggacc atggcctgac tccggaccaa gtggtggcta    4140
tcgccagcca cgatggcggc aagcaagcgc tcgaaacggt gcagcggctg ttgccggtgc    4200
tgtgccagga ccatggcctg accccggacc aagtggtggc tatcgccagc aacggtggcg    4260
gcaagcaagc gctcgaaacg gtgcagcggc tgttgccggt gctgtgccag gaccatggcc    4320
tgactccgga ccaagtggtg gctatcgcca gccacgatgg cggcaagcaa gcgctcgaaa    4380
cggtgcagcg gctgttgccg gtgctgtgcc aggaccatgg cctgactccg gaccaagtgg    4440
tggctatcgc cagccacgat ggcggcaagc aagcgctcga aacggtgcag cggctgttgc    4500
cggtgctgtg ccaggaccat ggcctgaccc cggaccaagt ggtggctatc gccagcaacg    4560
gtggcggcaa gcaagcgctc gaaagcattg tggcccagct gagccggcct gatccggcgt    4620
```

```
tggccgcgtt gaccaacgac cacctcgtcg ccttggcctg cctcggcgga cgtcctgcca    4680
tggatgcagt gaaaaaggga ttgccgcacg cgccggaatt gatcagaaga gtcaatcgcc    4740
gtattggcga acgcacgtcc catcgcgttg cgatatctag agtgggagga agctctcgca    4800
gagagtccat caacccatgg attctgactg gtttcactga tgccaaagga tcattcatgc    4860
taagaatccg taacacgaac aaccggtcag tagggtacta cacttcactg gtattcgaaa    4920
tcactctgca caacaaggac aaatcgattc ttgagaatat ccagtcgact tggaaggtcg    4980
gcacaatcaa caaccgaggc gacggcaccg ccagactgag cgtcactcgt ttcgaagatt    5040
tgaaagtgat tatcgaccac ttcgagaaat atccgctgat tacccagaaa ttgggcgatt    5100
acaagttgtt taaacaggca ttcagcgtca tggagaacaa agaacatctt aaggagaatg    5160
ggattaagga gctcgtacga atcaaagcta agatgaattg gggtctcaat gacgaattga    5220
aaaaagcatt tccagagaac atcagcaaag agcgccccct tatcaataag aacattccga    5280
atctcaaatg gctggctgga ttcacatctg gtgaaggcac attctacgtg cacctagcaa    5340
agtctgaagc tagcggcaag gtatacgtgc gactgaggtt cataatcggc cagcacatca    5400
gagacaagaa cctgatgaat tcattgataa catacctagg ctgtggtacg atccaggaga    5460
agaacaggtc taagggcagt atgctccact tcatagtaac taaattcagc gatatcaacg    5520
acaagatcat tccggtattc caggaaaata ctctgattgg cgtcaaactc gaggactttg    5580
aagattggtg caaggttgcc aaattgatcg aagagaagaa acacctgacc gaatccggtt    5640
tggatgagat taagaaaatc aagctgaaca tgaacaaagg tcgtgtcttc agcggccgct    5700
ccggtgaggg cagaggaagt cttctaacat gcggtgacgt ggaggagaat ccgggccccct   5760 ccggatctga gccacctcgg gctgagacct ttgtattcct ggacctagaa gccactgggc    5820
tcccaaacat ggaccctgag attgcagaga tatccctttt tgctgttcac cgctcttccc    5880
tggagaaccc agaacgggat gattctggtt ccttggtgct gccccgtgtt ctggacaagc    5940
tcacactgtg catgtgcccg gagcgcccct ttactgccaa ggccagtgag attactggtt    6000
tgagcagcga aagcctgatg cactgcggga aggctggttt caatggcgct gtggtaagga    6060
cactgcaggg cttcctaagc cgccaggagg gccccatctg ccttgtggcc cacaatggct    6120
tcgattatga cttcccactg ctgtgcacgg agctacaacg tctgggtgcc catctgcccc    6180 aagcacactgt ctgcctggac acactgcctg cattgcgggg cctggaccgt gctcacagcc    6240
acggcaccag ggctcaaggc cgcaaaagct acagcctggc cagtctcttc caccgctact    6300
tccaggctga acccagtgct gcccattcag cagaaggtga tgtgcacacc ctgcttctga    6360
tcttcctgca tcgtgctcct gagctgctcg cctgggcaga tgagcaggcc cgcagctggg    6420
ctcatattga gccatgtac gtgccacctg atggtccaag cctcgaagcc tgagcgatcg    6480
cgcgaccgag catcttaccg ccatttatac ccatatttgt tctgtttttc ttgatttggg    6540
tatacattta aatgttaata gaacaaaatg gtggggcaat catttacatt tttagggata    6600
tgtaattact agttcaggtg tattgccaca agacaaacat gttaagaaac tttcccgtta    6660
tttacgctct gttcctgtta atcaacctct ggattacaaa atttgtgaaa gattgactga    6720
tattcttaac tatgttgctc cttttacgct gtgtggatat gctgctttat agcctctgta    6780
tctagctatt gcttcccgta cggctttcgt tttctcctcc ttgtataaat cctggttgct    6840
gtctctttta gaggagttgt ggcccgttgt ccgtcaacgt ggcgtggtgt gctctgtgtt    6900
tgctgacgca accccactg gctggggcat tgccaccacc tgtcaactcc tttctgggac    6960
tttcgctttc cccctcccga tcgccacggc agaactcatc gccgcctgcc ttgcccgctg    7020
```

```
ctggacaggg gctaggttgc tgggcactga taattccgtg gtgttgtcat cgaattcggt    7080 accttttaa aagaaaaggg gggactggaa gggctaattc actcccaacg aagacaagat    7140
atcataactt cgtatagcat acattatacg aagttataat ttatttgtga aatttgtgat    7200
gctattgctt tatttgtaac catatgttta tttgtgaaat ttgtgatgct attgctttat    7260
ttgtaaccat tgcttttgc ttgtactggg tctctctggt tagaccagat ctgagcctgg    7320
gagctctctg gctaactagg gaacccactg cttaagcctc aataaagctt gcctcgacca    7380
gcctcgactg tgccttctag ttgccagcca tctgttgttt gcccctcccc cgtgccttcc    7440
ttgaccctgg aaggtgccac tcccactgtc ctttcctaat aaaatgagga aattgcatcg    7500
cattgtctga gtaggtgtca ttctattctg ggggtgggg tgggcagga cagcaagggg    7560 gaggattggg aagacaatag caggcatgct ggggatgcgg tgggctctat ggcctgcagc    7620
tgcattaatg aatcggccaa cgcgcgggga gaggcggttt gcgtattggg cgctcttccg    7680
cttcctcgct cactgactcg ctgcgctcgg tcgttcggct gcggcgagcg gtatcagctc    7740
actcaaaggc ggtaatacgg ttatccacag aatcaggga taacgcagga agaacatgt    7800 gagcaaaagg ccagcaaaag gccaggaacc gtaaaaaggc cgcgttgctg gcgttttcc    7860 ataggctccg ccccctgac gagcatcaca aaaatcgacg ctcaagtcag aggtggcgaa    7920
acccgacagg actataaaga taccaggcgt ttccccctgg aagctccctc gtgcgctctc    7980
ctgttccgac cctgccgctt accggatacc tgtccgcctt tctcccttcg ggaagcgtgg    8040
cgctttctca tagctcacgc tgtaggtatc tcagttcggt gtaggtcgtt cgctccaagc    8100
tgggctgtgt gcacgaaccc cccgttcagc ccgaccgctg cgccttatcc ggtaactatc    8160
gtcttgagtc caacccggta agacacgact tatcgccact ggcagcagcc actggtaaca    8220
ggattagcag agcgaggtat gtaggcggtg ctacagagtt cttgaagtgg tggcctaact    8280
acggctacac tagaaggaca gtatttggta tctgcgctct gctgaagcca gttaccttcg    8340
gaaaaagagt tggtagctct tgatccggca acaaaccac cgctggtagc ggtggttttt    8400
ttgtttgcaa gcagcagatt acgcgcagaa aaaaaggatc tcaagaagat cctttgatct    8460
tttctacggg gtctgacgct cagtggaacg aaaactcacg ttaagggatt ttggtcatga    8520
gattatcaaa aaggatcttc acctagatcc ttttaaatta aaaatgaagt tttaaatcaa    8580
tctaaagtat atatgagtaa acttggtctg acagttacca atgcttaatc agtgaggcac    8640
ctatctcagc gatctgtcta tttcgttcat ccatagttgc ctgactcccc gtcgtgtaga    8700
taactacgat acgggagggc ttaccatctg gccccagtgc tgcaatgata ccgcgagacc    8760
cacgctcacc ggctccagat ttatcagcaa taaaccagcc agccggaagg gccgagcgca    8820
gaagtggtcc tgcaacttta tccgcctcca tccagtctat taattgttgc cgggaagcta    8880
gagtaagtag ttcgccagtt aatagtttgc gcaacgttgt tgccattgct acaggcatcg    8940
tggtgtcacg ctcgtcgttt ggtatggctt cattcagctc cggttcccaa cgatcaaggc    9000
gagttacatg atcccccatg ttgtgcaaaa aagcggttag ctccttcggt cctccgatcg    9060
ttgtcagaag taagttggcc gcagtgttat cactcatggt tatggcagca ctgcataatt    9120
ctcttactgt catgccatcc gtaagatgct tttctgtgac tggtgagtac tcaaccaagt    9180
cattctgaga atagtgtatg cggcgaccga gttgctcttg cccggcgtca atacgggata    9240
ataccgcgcc acatagcaga actttaaaag tgctcatcat tggaaaacgt tcttcggggc    9300
gaaaactctc aaggatctta ccgctgttga gatccagttc gatgtaaccc actcgtgcac    9360
```

```
ccaactgatc ttcagcatct tttactttca ccagcgtttc tgggtgagca aaaacaggaa    9420
ggcaaaatgc cgcaaaaaag ggaataaggg cgacacggaa atgttgaata ctcatactct    9480
tccttttcca atattattga agcatttatc agggttattg tctcatgagc ggatacatat    9540
ttgaatgtat ttagaaaaat aaacaaatag gggttccgcg cacatttccc cgaaaagtgc    9600
cacct                                                                9605

<210> SEQ ID NO 28
<211> LENGTH: 3441
<212> TYPE: RNA
<213> ORGANISM: artificial sequence
<220> FEATURE:
<223> OTHER INFORMATION: MegaTal CCR5_S08 Trex2

<400> SEQUENCE: 28
augggauccu gcagguaucc auaugaugac ccagauuaug cgccaccuaa gaagaaacgc     60
aaagucgugg aucuacgcac gcucggcuac agucagcagc agcaagagaa gaucaaaccg    120
aaggugcguu cgacagugga gcagcaccac gaggcacugg ugggccaugg guuuacacac    180
gcgcacaucg uugcgcucag ccaacacccg gcagcguuag ggaccgucgc ugucacguau    240
cagcacauaa ucacggcguu gccagaggcg acacacgaag acaucguugg cgucggcaaa    300 caguguccg gcgcacgcgc ccuggaggcc uugcucacgg augcggggga uugagaggu    360 ccgccguuac aguggacac aggccaacuu gugaagauuc aaaacgugg cggcgugacc    420 gcaauggagg cagugcaugc aucgcgcaau gcacugacgg ugccccccu gaaccugacc    480 ccggaccaag ugguggcuau cgccagcaac aauggcggca agcaagcgcu cgaaacggug    540
cagcggcugu ugccggugcu gugccaggac cauggccuga ccccggacca aguggugcu    600 aucgccagca acguggcgg caagcaagcg cucgaaacgg ugcagcggcu guugccggug    660
cugugccagg accauggccu gacuccggac caaguggugg cuaucgccag ccacgauggc    720
ggcaagcaag cgcucgaaac ggugcagcgg cuguugccgg ugcugugcca ggaccauggc    780
cugacuccgg accaaguggu ggcuaucgcc agccacgaug cggcaagca agcgcucgaa    840 acggugcagc ggcuguugcc ggugcugugc caggaccaug ccugaccccc ggaccaagug    900
guggcuaucg ccagcaacgg uggcggcaag caagcgcucg aaacggugca gcggcuguug    960
ccggugcugu gccaggacca uggccugacc ccggaccaag ugguggcuau cgccagcaac   1020
gguggcggca agcaagcgcu cgaaacggug cagcggcugu ugccggugcu gugccaggac   1080
cauggccuga cuccggacca aguggugcu aucgccagcc acgauggcgg caagcaagcg   1140
cucgaaacgg ugcagcggcu guugccggug cugugccagg accauggccu gacccggac   1200 caagguggug cuaucgccag caacgguggc ggcaagcaag cgcucgaaac ggugcagcgg   1260
cuguugccgg ugcugugcca ggaccauggc cugacuccgg accaagguggu ggcuaucgcc   1320 agccacgaug cggcaagca agcgcucgaa acggugcagc ggcuguugcc ggugcugugc   1380
caggaccaug ccugacucc ggaccaagug guggcuaucg ccagccacga uggcggcaag   1440
caagcgcucg aaacggugca gcggcuguug ccggugcugu gccaggacca uggccugacc   1500
ccggaccaag ugguggcuau cgccagcaac gguggcggca agcaagcgcu cgaaagcauu   1560
guggcccagc ugagccggcc ugauccggcg uuggccgcgu ugaccaacga ccaccucguc   1620
gccuuggccu gccgggcgg acguccgcc auggaugcag ugaaaaggg auugccgcac   1680 gcgccggaau ugaucagaag agucaaucgc cguauuggcg aacgcacguc ccaucgcguu   1740
gcgauaucua gaguggaagg aagcucucgc agagagucca ucaacccaug gauucugacu   1800
```

```
gguuucacug augccgaagg aucauucaug cuaagaauoc guaacacgaa caaccgguca    1860 guagggua cu acacuucacu gguauucgaa aucacucugc acaacaagga caaaucgauu    1920
cuugagaaua uccagucgac uuggaagguc ggcacaauca caaccgagg cgacggcacc      1980 gccagacuga gcgucacucg uuucgaagau uugaaaguga uuaucgacca cuucgagaaa    2040
uauccgcuga uuacccagaa auugggcgau acaaguugu uuaaacaggc auucagcguc      2100
auggagaaca aagaacaucu uaaggagaau gggauuaagg agcucguacg aaucaaagcu    2160
aagaugaauu gggucucaa ugacgaauug aaaaaagcau uccagagaa caucagcaaa      2220 gagcgccccc uuaucaauaa gaacauuccg aaucucaaau ggcuggcugg auucacaucu    2280
ggugaaggca cauucuacgu gcaccuagca aagucugaag cuagcggcaa gguauacgug    2340
cgacugaggu ucauaaucgg ccagcacauc agagacaaga accugaugaa uucauugaua    2400
acauaccuag gcugugguac gauccaggag aagaacaggu cuaagggcag uaugcuccac    2460
uucauaguaa cuaaauucag cgauaucaac gacaagauca uuccgguauu ccaggaaaau    2520
acucugauug gcgucaaacu cgaggacuuu gaagauuggu gcaagguugc caaauugauc    2580
gaagagaaga acaccugac cgaauccggu uuggaugaga uuaagaaaau caagcugaac      2640
augaacaaag gucgucucuu cagcggccgc uccggugagg gcagaggaag ucuucuaaca    2700
ugcggugacg uggaggagaa uccggggccc uccggaucug agccaccucg ggcugagacc    2760
uuuguauucc uggaccuaga agccacuggg cucccaaaca uggaccccuga gauugcagag    2820 auaucccuuu uugcuguuca ccgcucuucc cuggagaacc cagaacggga ugauucuggu    2880
uccuuggugc ugccccgugu ucuggacaag cucacacugu gcaugugcoc ggagcgcccc    2940 uuuacugoca aggccaguga gauuacuggu uugagcagcg aaagccugau gcacugcggg    3000
aaggcugguu ucaauggcgc uguguaagg acacugcagg gcuuccuaag ccgccaggag    3060
ggccccaucu gccuugugoc ccacaauggc uucgauuaug acuucccacu gcugugcacg    3120
gagcuacaac gucugggugc ccaucugccc caagacacgu cugccugga cacacugccu    3180 gcauugcggg gccuggaccg ugcucacagc cacggcacca gggcucaagg ccgcaaaagc    3240
uacagccugg ccagucucuu ccaccgcuac uuccaggcug aacccagugc ugcccauuca    3300
gcagaaggug augugcacac ccugcuucug aucuuoocgc aucgugcucc ugagcugcuc    3360
gccugggcag augagcaggc ccgcagcugg gcucauauug agcccaugua cgugccaccu    3420
gaugguccaa gccucgaagc c                                              3441
```

<210> SEQ ID NO 29
<211> LENGTH: 9605
<212> TYPE: DNA
<213> ORGANISM: artificial sequence
<220> FEATURE:
<223> OTHER INFORMATION: MegaTAL CCR5_S08 LHE Trex2 lentiviral vector

<400> SEQUENCE: 29

```
gacgtcaatg tagtcttatg caatactctt gtagtcttgc aacatggtaa cgatgagtta     60
gcaacatgcc ttacaaggag agaaaaagca ccgtgcatgc cgattggtgg aagtaaggtg    120
gtacgatcgt gccttattag gaaggcaaca acgggtctg acatggattg gacgaaccac    180
tgaattgccg cattgcagag atattgtatt taagtgccta gctcgataca taaacgggtc    240
tctctggtta gaccagatct gagcctggga gctctctggc taactaggga acccactgct    300
taagcctcaa taaagcttgc cttgagtgct tcaagtagtg tgtgcccgtc tgttgtgtga    360
```

```
ctctggtaac tagagatccc tcagacccctt ttagtcagtg tggaaaatct ctagcagtgg    420
cgcccgaaca gggacttgaa agcgaaaggg aaaccagagg agctctctcg acgcaggact    480
cggcttgctg aagcgcgcac ggcaagaggc gaggggcggc gactggtgag tacgccaaaa    540
attttgacta gcggaggcta aaggagaga gatgggtgcg agagcgtcag tattaagcgg    600
gggagaatta gatcgcgatg ggaaaaaatt cggttaaggc caggggaaa gaaaaaatat    660 aaattaaaac atatagtatg ggcaagcagg gagctagaac gattcgcagt taatcctggc    720
ctgttagaaa catcagaagg ctgtagacaa atactgggac agctacaacc atcccttcag    780
acaggatcag aagaacttag atcattatat aatacagtag caaccctcta ttgtgtgcat    840
caaaggatag agataaaaga caccaaggaa gctttagaca agatagagga agagcaaaac    900
aaaagtaaga ccaccgcaca gcaagcggcc ctgatcttca gacctggagg aggagatatg    960
agggacaatt ggagaagtga attatataaa tataaagtag taaaaattga accattagga   1020
gtagcaccca ccaaggcaaa gagaagagtg gtgcagagag aaaaaagagc agtgggaata   1080
ggagctttgt tccttgggtt cttgggagca gcaggaagca ctatgggcgc agcgtcaatg   1140
acgctgacgg tacaggccag acaattattg tctggtatag tgcagcagca gaacaatttg   1200
ctgagggcta ttgaggcgca acagcatctg ttgcaactca cagtctgggg catcaagcag   1260
ctccaggcaa gaatcctggc tgtggaaaga tacctaaagg atcaacagct cctggggatt   1320
tggggttgct ctggaaaact catttgcacc actgctgtgc cttggaatgc tagttggagt   1380
aatgaatctc tggaacagat ttggaatcac acgacctgga tggagtggga cagagaaatt   1440
aacaattaca caagcttaat acactcctta attgaagaat cgcaaaacca gcaagaaaag   1500
aatgaacaag aattattgga attagataaa tgggcaagtt tgtggaattg gtttaacata   1560
acaaattggc tgtggtatat aaaattattc ataatgatag taggaggctt ggtaggttta   1620
agaatagttt ttgctgtact ttctatagtg aatagagtta ggcagggata ttcaccatta   1680
tcgtttcaga cccacctccc aaccccgagg ggacccgaca ggcccgaagg aatagaagaa   1740
gaaggtggag agagagacag agacagatcc attcgattag tgaacggatc tcgacggtat   1800
cggttaactt ttaaaagaaa aggggggatt ggggggtaca gtgcagggga agaatagta   1860 gacataatag caacagacat acaaactaaa gaattacaaa aacaaattac aaaaattcaa   1920
aattttatcg attacgcgtg tggcatctga agcaccacca gcgagcgaga gctagagaga   1980
aggaaagcca ccgacttcac cgcctccgag ctgctccggg tcgcgggtct gcagcgtcta   2040
cggccctccg cgcctacagc tcaagccaca tccgaagggg gagggagccg ggagctgcgc   2100
gcggggccgc cggggggagg ggtggcaccg cccacgccgg gcggccacga agggcggggc   2160
agcgggcgcg cgcccggcgg ggggagggc cgcgcgccgc gcccgctggg aattggggcc   2220 ctaggggag ggcggaggcg ccgacgaccg cggcacttac cgttcgcggc gtggcgcccg   2280
gtggtcccca aggggaggga aggggaggc ggggcgagga cagtgaccgg agtctcctca   2340
gcggtggctt ttctgcttgg cagcctcagc ggctggcgcc aaaaccggac tccgcccact   2400
tcctcgcccc tgcggtgcga gggtgtggaa tcctccagac gctgggggag ggggagttgg   2460
gagcttaaaa actagtaccc ctttgggacc actttcagca gcgaactctc ctgtacacca   2520
ggggtcagtt ccacagacgc gggccagggg tgggtcattg cggcgtgaac aataatttga   2580
ctagaagttg attcgggtgt ttccggaatt cctagctgca gtaacgccat tttgcaaggc   2640
atggaaaaat accaaaccaa gaatagagaa gttcagatca agggcgggta catgaaaata   2700
gctaacgttg ggccaaacag gatatctgcg gtgagcagtt tcggccccgg cccggggcca   2760
```

```
agaacagatg gtcaccgcag tttcggcccc ggcccgaggc caagaacaga tggtccccag    2820
atatggccca accctcagca gtttcttaag acccatcaga tgtttccagg ctcccccaag    2880
gacctgaaat gaccctgcgc cttatttgaa ttaaccaatc agcctgcttc tcgcttctgt    2940
tcgcgcgctt ctgcttcccg agctctataa aagagctcac aaccccctcac tcggcgcgcc   3000 taatacgact cactataggg gccgccacca tgggatcctg caggtatcca tatgatgtcc    3060
cagattatgc gccacctaag aagaaacgca aagtcgtgga tctacgcacg ctcggctaca    3120
gtcagcagca gcaagagaag atcaaaccga aggtgcgttc gacagtggcg cagcaccacg    3180
aggcactggt gggccatggg tttacacacg cgcacatcgt tgcgctcagc caacacccgg    3240
cagcgttagg gaccgtcgct gtcacgtatc agcacataat cacggcgttg ccagaggcga    3300
cacacgaaga catcgttggc gtcggcaaac agtggtccgg cgcacgcgcc ctggaggcct    3360
tgctcacgga tgcgggggag ttgagaggtc cgccgttaca gttggacaca ggccaacttg    3420
tgaagattgc aaaacgtggc ggcgtgaccg caatggaggc agtgcatgca tcgcgcaatg    3480
cactgacggg tgcccccctg aacctgaccc cggaccaagt ggtggctatc gccagcaaca    3540
atggcggcaa gcaagcgctc gaaacggtgc agcggctgtt gccggtgctg tgccaggacc    3600
atggcctgac cccggaccaa gtggtggcta tcgccagcaa cggtggcggc aagcaagcgc    3660
tcgaaacggt gcagcggctg ttgccggtgc tgtgccagga ccatggcctg actccggacc    3720
aagtggtggc tatcgccagc cacgatggcg gcaagcaagc gctcgaaacg gtgcagcggc    3780
tgttgccggt gctgtgccag gaccatggcc tgactccgga ccaagtggtg ctatcgcca     3840 gccacgatgg cggcaagcaa gcgctcgaaa cggtgcagcg gctgttgccg gtgctgtgcc    3900
aggaccatgg cctgaccccg gaccaagtgg tggctatcgc cagcaacggt ggcggcaagc    3960
aagcgctcga aacggtgcag cggctgttgc cggtgctgtg ccaggaccat ggcctgaccc    4020
cggaccaagt ggtggctatc gccagcaacg gtggcggcaa gcaagcgctc gaaacggtgc    4080
agcggctgtt gccggtgctg tgccaggacc atggcctgac tccggaccaa gtggtggcta    4140
tcgccagcca cgatggcggc aagcaagcgc tcgaaacggt gcagcggctg ttgccggtgc    4200
tgtgccagga ccatggcctg accccggacc aagtggtggc tatcgccagc aacggtggcg    4260
gcaagcaagc gctcgaaacg gtgcagcggc tgttgccggt gctgtgccag gaccatggcc    4320
tgactccgga ccaagtggtg ctatcgcca gccacgatgg cggcaagcaa gcgctcgaaa    4380
cggtgcagcg gctgttgccg gtgctgtgcc aggaccatgg cctgactccg gaccaagtgg    4440
tggctatcgc cagccacgat ggcggcaagc aagcgctcga acggtgcag cggctgttgc     4500 cggtgctgtg ccaggaccat ggcctgaccc ggaccaagt ggtggctatc gccagcaacg     4560
gtggcggcaa gcaagcgctc gaaagcattg tggcccagct gagccggcct gatccggcgt    4620
tggccgcgtt gaccaacgac cacctcgtcg ccttggcctg cctcggcgga cgtcctgcca    4680
tggatgcagt gaaaaaggga ttgcgcacg cgccggaatt gatcagaaga gtcaatcgcc     4740
gtattggcga acgcacgtcc catcgcgttg cgatatctag agtgggagga agctctcgca    4800
gagagtccat caacccatgg attctgactg gtttcactga tgccgaagga tcattcatgc    4860
taagaatccg taacacgaac aaccggtcag tagggtacta cacttcactg gtattcgaaa    4920
tcactctgca caacaaggac aaatcgattc ttgagaatat ccagtcgact tggaaggtcg    4980
gcacaatcaa caaccgaggc gacggcaccg ccagactgag cgtcactcgt ttcgaagatt    5040
tgaaagtgat tatcgaccac ttcgagaaat atccgctgat tacccagaaa ttgggcgatt    5100
```

-continued

```
acaagttgtt taaacaggca ttcagcgtca tggagaacaa agaacatctt aaggagaatg    5160
ggattaagga gctcgtacga atcaaagcta agatgaattg gggtctcaat gacgaattga    5220
aaaaagcatt tccagagaac atcagcaaag agcgcccct tatcaataag aacattccga     5280
atctcaaatg gctggctgga ttcacatctg gtgaaggcac attctacgtg cacctagcaa    5340
agtctgaagc tagcggcaag gtatacgtgc gactgaggtt cataatcggc cagcacatca    5400
gagacaagaa cctgatgaat tcattgataa catacctagg ctgtggtacg atccaggaga    5460
agaacaggtc taagggcagt atgctccact tcatagtaac taaattcagc gatatcaacg    5520
acaagatcat tccggtattc caggaaaata ctctgattgg cgtcaaactc gaggactttg    5580
aagattggtg caaggttgcc aaattgatcg aagagaagaa acacctgacc gaatccggtt    5640
tggatgagat taagaaaatc aagctgaaca tgaacaaagg tcgtgtcttc agcggccgct    5700
ccggtgaggg cagaggaagt cttctaacat gcggtgacgt ggaggagaat ccgggcccct    5760
ccggatctga gccacctcgg gctgagacct ttgtattcct ggacctagaa gccactgggc    5820
tcccaaacat ggaccctgag attgcagaga tatcccttt tgctgttcac cgtcttccc      5880 tggagaaccc agaacgggat gattctggtt ccttggtgct gccccgtgtt ctggacaagc    5940
tcacactgtg catgtgcccg gagcgccct ttactgccaa ggccagtgag attactggtt     6000
tgagcagcga aagcctgatg cactgcggga aggctggttt caatggcgct gtggtaagga    6060
cactgcaggc cttcctaagc cgccaggagg cccccatctg ccttgtggcc cacaatggct    6120
tcgattatga cttcccactg ctgtgcacgg agctacaacg tctgggtgcc catctgcccc    6180
aagacactgt ctgcctggac acactgcctg cattgcgggg cctggaccgt gctcacagcc    6240
acggcaccag ggctcaaggc cgcaaaagct acagcctggc cagtctcttc caccgctact    6300
tccaggctga acccagtgct gcccattcag cagaaggtga tgtgcacacc ctgcttctga    6360
tcttcctgca tcgtgctcct gagctgctcg cctgggcaga tgagcaggcc cgcagctggg    6420
ctcatattga gcccatgtac gtgccacctg atggtccaag cctcgaagcc tgagcgatcg    6480
cgcgaccgag catcttaccg ccatttatac ccatatttgt tctgtttttc ttgatttggg    6540
tatacattta aatgttaata gaacaaaatg gtggggcaat catttacatt tttagggata    6600
tgtaattact agttcaggtg tattgccaca agacaaacat gttaagaaac tttcccgtta    6660
tttacgctct gttcctgtta atcaacctct ggattacaaa atttgtgaaa gattgactga    6720
tattcttaac tatgttgctc cttttacgct gtgtggatat gctgctttat agcctctgta    6780
tctagctatt gcttcccgta cggctttcgt tttctcctcc ttgtataaat cctggttgct    6840
gtctctttta gaggagttgt ggcccgttgt ccgtcaacgt ggcgtggtgt gctctgtgtt    6900
tgctgacgca acccccactg gctggggcat tgccaccacc tgtcaactcc tttctgggac    6960
tttcgctttc cccctcccga tcgccacggc agaactcatc gccgcctgcc ttgcccgctg    7020
ctggacaggg gctaggttgc tgggcactga taattccgtg gtgttgtcat cgaattcggt    7080 accttttaa aagaaaaggg gggactggaa gggctaattc actcccaacg aagacaagat     7140
atcataactt cgtatagcat acattatacg aagttataat ttatttgtga aatttgtgat    7200
gctattgctt tatttgtaac catatgttta tttgtgaaat tgtgatgct attgctttat     7260 ttgtaaccat tgcttttgc ttgtactggg tctctctggt tagaccagat ctgagcctgg     7320
gagctctctg gctaactagg gaacccactg cttaagcctc aataaagctt gcctcgacca    7380
gcctcgactg tgccttctag ttgccagcca tctgttgttt gccctcccc cgtgccttcc     7440 ttgaccctgg aaggtgccac tcccactgtc ctttcctaat aaaatgagga aattgcatcg    7500
```

```
cattgtctga gtaggtgtca ttctattctg gggggtgggg tggggcagga cagcaagggg    7560
gaggattggg aagacaatag caggcatgct ggggatgcgg tgggctctat ggcctgcagc    7620
tgcattaatg aatcggccaa cgcgcgggga gaggcggttt gcgtattggg cgctcttccg    7680
cttcctcgct cactgactcg ctgcgctcgg tcgttcggct gcggcgagcg gtatcagctc    7740
actcaaaggc ggtaatacgg ttatccacag aatcagggga taacgcagga agaacatgt    7800 gagcaaaagg ccagcaaaag gccaggaacc gtaaaaaggc cgcgttgctg gcgtttttcc    7860
ataggctccg ccccctgac gagcatcaca aaaatcgacg ctcaagtcag aggtggcgaa    7920
acccgacagg actataaaga taccaggcgt ttccccctgg aagctccctc gtgcgctctc    7980
ctgttccgac cctgccgctt accggatacc tgtccgcctt ctcccttcg ggaagcgtgg    8040 cgctttctca tagctcacgc tgtaggtatc tcagttcggt gtaggtcgtt cgctccaagc    8100
tgggctgtgt gcacgaaccc cccgttcagc ccgaccgctg cgccttatcc ggtaactatc    8160
gtcttgagtc caacccggta agacacgact tatcgccact ggcagcagcc actggtaaca    8220
ggattagcag agcgaggtat gtaggcggtg ctacagagtt cttgaagtgg tggcctaact    8280
acggctacac tagaaggaca gtatttggta tctgcgctct gctgaagcca gttaccttcg    8340
gaaaaagagt tggtagctct tgatccggca acaaaccac cgctggtagc ggtggttttt    8400
ttgtttgcaa gcagcagatt acgcgcagaa aaaaggatc tcaagaagat cctttgatct    8460
tttctacggg gtctgacgct cagtggaacg aaaactcacg ttaagggatt ttggtcatga    8520
gattatcaaa aaggatcttc acctagatcc ttttaaatta aaatgaagt tttaaatcaa    8580 tctaaagtat atatgagtaa acttggtctg acagttacca atgcttaatc agtgaggcac    8640
ctatctcagc gatctgtcta tttcgttcat ccatagttgc ctgactcccc gtcgtgtaga    8700
taactacgat acgggagggc ttaccatctg gccccagtgc tgcaatgata ccgcgagacc    8760
cacgctcacc ggctccagat ttatcagcaa taaaccagcc agccggaagg gccgagcgca    8820
gaagtggtcc tgcaacttta tccgcctcca tccagtctat taattgttgc cgggaagcta    8880
gagtaagtag ttcgccagtt aatagtttgc gcaacgttgt tgccattgct acaggcatcg    8940
tggtgtcacg ctcgtcgttt ggtatggctt cattcagctc cggttcccaa cgatcaaggc    9000
gagttacatg atccccatg ttgtgcaaaa aagcggttag ctccttcggt cctccgatcg    9060
ttgtcagaag taagttggcc gcagtgttat cactcatggt tatggcagca ctgcataatt    9120
ctcttactgt catgccatcc gtaagatgct tttctgtgac tggtgagtac tcaaccaagt    9180
cattctgaga atagtgtatg cggcgaccga gttgctcttg cccggcgtca atacgggata    9240
ataccgcgcc acatagcaga actttaaaag tgctcatcat tggaaaacgt tcttcggggc    9300
gaaaactctc aaggatctta ccgctgttga tccagttc gatgtaaccc actcgtgcac    9360
ccaactgatc ttcagcatct tttactttca ccagcgtttc tgggtgagca aaaacaggaa    9420
ggcaaaatgc cgcaaaaaag gaataagggc gacacggaa atgttgaata ctcatactct    9480
tcctttttca atattattga agcatttatc agggttattg tctcatgagc ggatacatat    9540
ttgaatgtat ttagaaaaat aaacaaatag gggttccgcg cacatttccc cgaaaagtgc    9600
cacct                                                                9605
```

<210> SEQ ID NO 30
<211> LENGTH: 909
<212> TYPE: DNA
<213> ORGANISM: artificial sequence
<220> FEATURE:

<223> OTHER INFORMATION: LHE CCR5_S08_-10+10+11

<400> SEQUENCE: 30

```
atggcataca tgtcgcgcag agagtccatc aacccatgga ttctgactgg tttcgctgat    60
gccgaagcat ccttcatgct aagaatccgt agcgcgaaca accggtcagt agggtactac   120
actgacctgg tattcgaaat cactctgcac aacaaggaca atcgattct ggagaatatc    180
cagtcgactt ggaaggtcgg cacaatcaac aaccgaggcg acggcaccgt cagactgagc   240
gtcacgcgcc acgaagattt gaaagtgatt atcgaccact tcgagaaata tccgctgatt   300
acccagaaat tgggcgatta caagttgttt aaacaggcat tcagcgtcat ggagaacaaa   360
gaacatctta aggagaatgg gattaaggag ctcgtacgaa tcaaagctaa gatgaattgg   420
ggtctcaatg acgaattgaa aaagcatttt ccagagaaca tcagcaaaga gcgccccctt   480
atcaataaga acattccgaa tctcaaatgg ctggctggat tcacatctgg tgaaggcaca   540
ttctacgtgc acctagcaaa gcccacccgc cagaacaagg tacaggtgcg actgaggttc   600
ataatcggcc agcacatccg agacaagaac ctgatgaatt cattgataac atacctaggc   660
tgtggtacga tccaggagaa gaacaggtct aagggcagta tgctccactt catagtaact   720
aaattcagcg atatcaacga caagatcatt ccggtattcc aggaaaatac tctgattggc   780
gtcaaactcg aggactttga agattggtgc aaggttgcca aattgatcga agagaagaaa   840
cacctgaccg aatccggttt ggatgagatt aagaaaatca agctgaacat gaacaaaggt   900
cgtgtcttc                                                           909
```

<210> SEQ ID NO 31
<211> LENGTH: 303
<212> TYPE: PRT
<213> ORGANISM: artificial sequence
<220> FEATURE:
<223> OTHER INFORMATION: LHE CCR5_S08_-10+10+11

<400> SEQUENCE: 31

```
Met Ala Tyr Met Ser Arg Arg Glu Ser Ile Asn Pro Trp Ile Leu Thr
1               5                   10                  15

Gly Phe Ala Asp Ala Glu Ala Ser Phe Met Leu Arg Ile Arg Ser Ala
            20                  25                  30

Asn Asn Arg Ser Val Gly Tyr Tyr Thr Asp Leu Val Phe Glu Ile Thr
        35                  40                  45

Leu His Asn Lys Asp Lys Ser Ile Leu Glu Asn Ile Gln Ser Thr Trp
    50                  55                  60

Lys Val Gly Thr Ile Asn Asn Arg Gly Asp Gly Thr Val Arg Leu Ser
65                  70                  75                  80

Val Thr Arg His Glu Asp Leu Lys Val Ile Ile Asp His Phe Glu Lys
                85                  90                  95

Tyr Pro Leu Ile Thr Gln Lys Leu Gly Asp Tyr Lys Leu Phe Lys Gln
            100                 105                 110

Ala Phe Ser Val Met Glu Asn Lys Glu His Leu Lys Glu Asn Gly Ile
        115                 120                 125

Lys Glu Leu Val Arg Ile Lys Ala Lys Met Asn Trp Gly Leu Asn Asp
    130                 135                 140

Glu Leu Lys Lys Ala Phe Pro Glu Asn Ile Ser Lys Glu Arg Pro Leu
145                 150                 155                 160

Ile Asn Lys Asn Ile Pro Asn Leu Lys Trp Leu Ala Gly Phe Thr Ser
                165                 170                 175
```

Gly Glu Gly Thr Phe Tyr Val His Leu Ala Lys Pro Thr Arg Gln Asn
            180                 185                 190

Lys Val Gln Val Arg Leu Arg Phe Ile Ile Gly Gln His Ile Arg Asp
        195                 200                 205

Lys Asn Leu Met Asn Ser Leu Ile Thr Tyr Leu Gly Cys Gly Thr Ile
    210                 215                 220

Gln Glu Lys Asn Arg Ser Lys Gly Ser Met Leu His Phe Ile Val Thr
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Glu Asp Trp Cys Lys Val
            260                 265                 270

Ala Lys Leu Ile Glu Glu Lys Lys His Leu Thr Glu Ser Gly Leu Asp
        275                 280                 285

Glu Ile Lys Lys Ile Lys Leu Asn Met Asn Lys Gly Arg Val Phe
    290                 295                 300

<210> SEQ ID NO 32
<211> LENGTH: 3378
<212> TYPE: DNA
<213> ORGANISM: artificial sequence
<220> FEATURE:
<223> OTHER INFORMATION: MegaTAL CCR5_S08_-10+10+11_Trex2

<400> SEQUENCE: 32

```
atgggatcct gcaggtatcc atatgatgtc cagattatg cgccacctaa gagaaacgc      60
aaagtcgtgg atctacgcac gctcggctac agtcagcagc agcaagagaa gatcaaaccg    120
aaggtgcgtt cgacagtggc gcagcaccac gaggcactgg tgggccatgg gtttacacac    180
gcgcacatcg ttgcgctcag ccaacacccg gcagcgttag gaccgtcgc tgtcacgtat     240
cagcacataa tcacggcgtt gccagaggcg acacacgaag acatcgttgg cgtcggcaaa    300
cagtggtccg gcgcacgcgc cctggaggcc ttgctcacgg atgcggggga ttgagaggt     360
ccgccgttac agttggacac aggccaactt gtgaagattg caaaacgtgg cggcgtgacc    420
gcaatggagg cagtgcatgc atcgcgcaat gcactgacgg gtgccccccct gaacctgacc    480
ccggaccaag tggtggctat cgccagcaac aatggcggca agcaagcgct cgaaacggtg    540
cagcggctgt tgccggtgct gtgccaggac catggcctga ccccggacca agtggtggct    600
atcgccagca acggtggcgg caagcaagcg ctcgaaacgg tgcagcggct gttgccggtg    660
ctgtgccagg accatggcct gactccggac caagtggtgg ctatcgccag ccacgatggc    720
ggcaagcaag cgctcgaaac ggtgcagcgg ctgttgccgg tgctgtgcca ggaccatggc    780
ctgactccgg accaagtggt ggctatcgcc agccacgatg gcggcaagca agcgctcgaa    840
acggtgcagc ggctgttgcc ggtgctgtgc caggaccatg gcctgacccc ggaccaagtg    900
gtggctatcg ccagcaacgg tggcggcaag caagcgctcg aaacggtgca gcggctgttg    960
ccggtgctgt gccaggacca tggcctgacc ccggaccaag tggtggctat cgccagcaac   1020
ggtggcggca agcaagcgct cgaaacggtg cagcggctgt tgccggtgct gtgccaggac   1080
catggcctga ctccggacca agtggtggct atcgccagcc acgatggcgg caagcaagcg   1140
ctcgaaacgg tgcagcggct gttgccggtg ctgtgccagg accatggcct gaccccggac   1200
caagtggtgg ctatcgccag caacggtggc ggcaagcaag cgctcgaaac ggtgcagcgg   1260
ctgttgccgg tgctgtgcca ggaccatggc ctgactccgg accaagtggt ggctatcgcc   1320
agccacgatg gcggcaagca agcgctcgaa acggtgcagc ggctgttgcc ggtgctgtgc   1380
```

```
caggaccatg gcctgactcc ggaccaagtg gtggctatcg ccagccacga tggcggcaag    1440
caagcgctcg aaacggtgca gcggctgttg ccggtgctgt gccaggacca tggcctgacc    1500
ccggaccaag tggtggctat cgccagcaac ggtggcggca agcaagcgct cgaaagcatt    1560
gtggcccagc tgagccggcc tgatccggcg ttggccgcgt tgaccaacga ccacctcgtc    1620
gccttggcct gcctcggcgg acgtcctgcc atggatgcag tgaaaaaggg attgccgcac    1680
gcgccggaat tgatcagaag agtcaatcgc cgtattggcg aacgcacgtc ccatcgcgtt    1740
gcgatatcta gagtgggagg aagctcgcgc agagagtcca tcaacccatg gattctgact    1800
ggtttcgctg atgccgaagc atccttcatg ctaagaatcc gtagcgcgaa caaccggtca    1860
gtagggtact acactgacct ggtattcgaa atcactctgc acaacaagga caaatcgatt    1920
ctggagaata tccagtcgac ttggaaggtc ggcacaatca caaccgagg cgacggcacc    1980 gtcagactga gcgtcacgcg ccacgaagat ttgaaagtga ttatcgacca cttcgagaaa    2040
tatccgctga ttacccagaa attgggcgat acaagttgt ttaaacaggc attcagcgtc    2100
atggagaaca agaacatct taaggagaat gggattaagg agctcgtacg aatcaaagct    2160
aagatgaatt ggggtctcaa tgacgaattg aaaaaagcat tccagagaa catcagcaaa    2220 gagcgcccc ttatcaataa gaacattccg aatctcaaat ggctggctgg attcacatct    2280
ggtgaaggca cattctacgt gcacctagca aagcccaccc gccagaacaa ggtacaggtg    2340
cgactgaggt tcataatcgg ccagcacatc cgagacaaga acctgatgaa ttcattgata    2400
acatacctag gctgtggtac gatccaggag aagaacaggc taagggcag tatgctccac    2460 ttcatagtaa ctaaattcag cgatatcaac gacaagatca ttccggtatt ccaggaaaat    2520
actctgattg gcgtcaaact cgaggacttt gaagattggt gcaaggttgc caaattgatc    2580
gaagagaaga aacacctgac cgaatccggt ttggatgaga ttaagaaaat caagctgaac    2640
atgaacaaag gtcgtgtctt cgctagcacc ggttctgagc cacctcgggc tgagaccttt    2700
gtattcctgg acctagaagc cactgggctc ccaaacatgg accctgagat tgcagagata    2760
tccctttttg ctgttcaccg ctcttccctg gagaacccag aacgggatga ttctggttcc    2820
ttggtgctgc cccgtgttct ggacaagctc acactgtgca tgtgcccgga cgcccctt    2880 actgccaagg ccagtgagat tactggtttg agcagcgaaa gcctgatgca ctgcgggaag    2940
gctggtttca tgcgctgt ggtaaggaca ctgcagggct tcctaagccg ccaggagggc    3000
cccatctgcc ttgtggccca caatggcttc gattatgact tcccactgct gtgcacggag    3060
ctacaacgtc tgggtgccca tctgccccaa gacactgtct gcctggacac actgcctgca    3120
ttgcggggcc tggaccgtgc tcacagccac ggcaccaggg ctcaaggccg caaaagctac    3180
agcctggcca gtctcttcca ccgctacttc caggctgaac ccagtgctgc ccattcagca    3240
gaaggtgatg tgcacaccct gcttctgatc ttcctgcatc gtgctcctga gctgctcgcc    3300
tgggcagatg agcaggcccg cagctgggct catattgagc ccatgtacgt gccacctgat    3360
ggtccaagcc tcgaagcc                                                 3378
```

<210> SEQ ID NO 33
<211> LENGTH: 1126
<212> TYPE: PRT
<213> ORGANISM: artificial sequence
<220> FEATURE:
<223> OTHER INFORMATION: MegaTAL CCR5_S08_-10+10+11_Trex2

<400> SEQUENCE: 33

```
Met Gly Ser Cys Arg Tyr Pro Tyr Asp Val Pro Asp Tyr Ala Pro Pro
1               5                   10                  15

Lys Lys Lys Arg Lys Val Val Asp Leu Arg Thr Leu Gly Tyr Ser Gln
            20                  25                  30

Gln Gln Gln Glu Lys Ile Lys Pro Lys Val Arg Ser Thr Val Ala Gln
        35                  40                  45

His His Glu Ala Leu Val Gly His Gly Phe Thr His Ala His Ile Val
    50                  55                  60

Ala Leu Ser Gln His Pro Ala Ala Leu Gly Thr Val Ala Val Thr Tyr
65                  70                  75                  80

Gln His Ile Ile Thr Ala Leu Pro Glu Ala Thr His Glu Asp Ile Val
                85                  90                  95

Gly Val Gly Lys Gln Trp Ser Gly Ala Arg Ala Leu Glu Ala Leu Leu
            100                 105                 110

Thr Asp Ala Gly Glu Leu Arg Gly Pro Pro Leu Gln Leu Asp Thr Gly
        115                 120                 125

Gln Leu Val Lys Ile Ala Lys Arg Gly Gly Val Thr Ala Met Glu Ala
        130                 135                 140

Val His Ala Ser Arg Asn Ala Leu Thr Gly Ala Pro Leu Asn Leu Thr
145                 150                 155                 160

Pro Asp Gln Val Val Ala Ile Ala Ser Asn Asn Gly Gly Lys Gln Ala
                165                 170                 175

Leu Glu Thr Val Gln Arg Leu Leu Pro Val Leu Cys Gln Asp His Gly
            180                 185                 190

Leu Thr Pro Asp Gln Val Val Ala Ile Ala Ser Asn Gly Gly Gly Lys
        195                 200                 205

Gln Ala Leu Glu Thr Val Gln Arg Leu Leu Pro Val Leu Cys Gln Asp
        210                 215                 220

His Gly Leu Thr Pro Asp Gln Val Val Ala Ile Ala Ser His Asp Gly
225                 230                 235                 240

Gly Lys Gln Ala Leu Glu Thr Val Gln Arg Leu Leu Pro Val Leu Cys
                245                 250                 255

Gln Asp His Gly Leu Thr Pro Asp Gln Val Val Ala Ile Ala Ser His
            260                 265                 270

Asp Gly Gly Lys Gln Ala Leu Glu Thr Val Gln Arg Leu Leu Pro Val
        275                 280                 285

Leu Cys Gln Asp His Gly Leu Thr Pro Asp Gln Val Val Ala Ile Ala
        290                 295                 300

Ser Asn Gly Gly Gly Lys Gln Ala Leu Glu Thr Val Gln Arg Leu Leu
305                 310                 315                 320

Pro Val Leu Cys Gln Asp His Gly Leu Thr Pro Asp Gln Val Val Ala
                325                 330                 335

Ile Ala Ser Asn Gly Gly Gly Lys Gln Ala Leu Glu Thr Val Gln Arg
            340                 345                 350

Leu Leu Pro Val Leu Cys Gln Asp His Gly Leu Thr Pro Asp Gln Val
        355                 360                 365

Val Ala Ile Ala Ser His Asp Gly Gly Lys Gln Ala Leu Glu Thr Val
        370                 375                 380

Gln Arg Leu Leu Pro Val Leu Cys Gln Asp His Gly Leu Thr Pro Asp
385                 390                 395                 400

Gln Val Val Ala Ile Ala Ser Asn Gly Gly Gly Lys Gln Ala Leu Glu
                405                 410                 415

Thr Val Gln Arg Leu Leu Pro Val Leu Cys Gln Asp His Gly Leu Thr
```

```
                420             425             430
Pro Asp Gln Val Val Ala Ile Ala Ser His Asp Gly Gly Lys Gln Ala
            435                 440                 445

Leu Glu Thr Val Gln Arg Leu Leu Pro Val Leu Cys Gln Asp His Gly
        450                 455                 460

Leu Thr Pro Asp Gln Val Val Ala Ile Ala Ser His Asp Gly Gly Lys
465                 470                 475                 480

Gln Ala Leu Glu Thr Val Gln Arg Leu Leu Pro Val Leu Cys Gln Asp
                485                 490                 495

His Gly Leu Thr Pro Asp Gln Val Val Ala Ile Ala Ser Asn Gly Gly
            500                 505                 510

Gly Lys Gln Ala Leu Glu Ser Ile Val Ala Gln Leu Ser Arg Pro Asp
        515                 520                 525

Pro Ala Leu Ala Ala Leu Thr Asn Asp His Leu Val Ala Leu Ala Cys
    530                 535                 540

Leu Gly Gly Arg Pro Ala Met Asp Ala Val Lys Lys Gly Leu Pro His
545                 550                 555                 560

Ala Pro Glu Leu Ile Arg Arg Val Asn Arg Arg Ile Gly Glu Arg Thr
                565                 570                 575

Ser His Arg Val Ala Ile Ser Arg Val Gly Gly Ser Ser Arg Arg Glu
            580                 585                 590

Ser Ile Asn Pro Trp Ile Leu Thr Gly Phe Ala Asp Ala Glu Ala Ser
        595                 600                 605

Phe Met Leu Arg Ile Arg Ser Ala Asn Asn Arg Ser Val Gly Tyr Tyr
    610                 615                 620

Thr Asp Leu Val Phe Glu Ile Thr Leu His Asn Lys Asp Lys Ser Ile
625                 630                 635                 640

Leu Glu Asn Ile Gln Ser Thr Trp Lys Val Gly Thr Ile Asn Asn Arg
                645                 650                 655

Gly Asp Gly Thr Val Arg Leu Ser Val Thr Arg His Glu Asp Leu Lys
            660                 665                 670

Val Ile Ile Asp His Phe Glu Lys Tyr Pro Leu Ile Thr Gln Lys Leu
        675                 680                 685

Gly Asp Tyr Lys Leu Phe Lys Gln Ala Phe Ser Val Met Glu Asn Lys
    690                 695                 700

Glu His Leu Lys Glu Asn Gly Ile Lys Glu Leu Val Arg Ile Lys Ala
705                 710                 715                 720

Lys Met Asn Trp Gly Leu Asn Asp Glu Leu Lys Lys Ala Phe Pro Glu
                725                 730                 735

Asn Ile Ser Lys Glu Arg Pro Leu Ile Asn Lys Asn Ile Pro Asn Leu
            740                 745                 750

Lys Trp Leu Ala Gly Phe Thr Ser Gly Glu Gly Thr Phe Tyr Val His
        755                 760                 765

Leu Ala Lys Pro Thr Arg Gln Asn Lys Val Gln Val Arg Leu Arg Phe
    770                 775                 780

Ile Ile Gly Gln His Ile Arg Asp Lys Asn Leu Met Asn Ser Leu Ile
785                 790                 795                 800

Thr Tyr Leu Gly Cys Gly Thr Ile Gln Glu Lys Asn Arg Ser Lys Gly
                805                 810                 815

Ser Met Leu His Phe Ile Val Thr Lys Phe Ser Asp Ile Asn Asp Lys
            820                 825                 830

Ile Ile Pro Val Phe Gln Glu Asn Thr Leu Ile Gly Val Lys Leu Glu
        835                 840                 845
```

```
Asp Phe Glu Asp Trp Cys Lys Val Ala Lys Leu Ile Glu Lys Lys
    850             855             860

His Leu Thr Glu Ser Gly Leu Asp Glu Ile Lys Lys Ile Lys Leu Asn
865             870             875             880

Met Asn Lys Gly Arg Val Phe Ala Ser Thr Gly Ser Glu Pro Pro Arg
                885             890             895

Ala Glu Thr Phe Val Phe Leu Asp Leu Glu Ala Thr Gly Leu Pro Asn
            900             905             910

Met Asp Pro Glu Ile Ala Glu Ile Ser Leu Phe Ala Val His Arg Ser
        915             920             925

Ser Leu Glu Asn Pro Glu Arg Asp Asp Ser Gly Ser Leu Val Leu Pro
    930             935             940

Arg Val Leu Asp Lys Leu Thr Leu Cys Met Cys Pro Glu Arg Pro Phe
945             950             955             960

Thr Ala Lys Ala Ser Glu Ile Thr Gly Leu Ser Ser Glu Ser Leu Met
                965             970             975

His Cys Gly Lys Ala Gly Phe Asn Gly Ala Val Val Arg Thr Leu Gln
            980             985             990

Gly Phe Leu Ser Arg Gln Glu Gly Pro Ile Cys Leu Val Ala His Asn
    995             1000            1005

Gly Phe Asp Tyr Asp Phe Pro Leu Leu Cys Thr Glu Leu Gln Arg Leu
    1010            1015            1020

Gly Ala His Leu Pro Gln Asp Thr Val Cys Leu Asp Thr Leu Pro Ala
1025            1030            1035            1040

Leu Arg Gly Leu Asp Arg Ala His Ser His Gly Thr Arg Ala Gln Gly
                1045            1050            1055

Arg Lys Ser Tyr Ser Leu Ala Ser Leu Phe His Arg Tyr Phe Gln Ala
                1060            1065            1070

Glu Pro Ser Ala Ala His Ser Ala Glu Gly Asp Val His Thr Leu Leu
                1075            1080            1085

Leu Ile Phe Leu His Arg Ala Pro Glu Leu Leu Ala Trp Ala Asp Glu
    1090            1095            1100

Gln Ala Arg Ser Trp Ala His Ile Glu Pro Met Tyr Val Pro Pro Asp
1105            1110            1115            1120

Gly Pro Ser Leu Glu Ala
                1125
```

LAGLIDADG HOMING ENDONUCLEASE CLEAVING THE C-C CHEMOKINE RECEPTOR TYPE-5 (CCR5) GENE AND USES THEREOF

FIELD OF THE INVENTION

The present disclosure relates to molecular and cellular biology, genetics, genomics, and their applications in human therapeutics. Particular aspects relate to a rare-cutting endonuclease cleaving a nucleic acid target sequence from the CCR5 gene, more particularly to a new meganuclease variant of I-Onul or homologues that is particularly efficient in disrupting the expression of this gene in T-cells, and the use thereof for anti-HIV therapy.

BACKGROUND

Site-specific nucleases are powerful reagents for specifically and efficiently targeting and modifying a DNA sequence within a complex genome. The double-stranded DNA breaks caused by site-specific nucleases are commonly repaired through the distinct mechanisms of homologous recombination or non-homologous end joining (NHEJ). Although homologous recombination typically uses the sister chromatid of the damaged DNA as a donor matrix from which to perform perfect repair of the genetic lesion, NHEJ is an imperfect repair process that often results in changes to the DNA sequence at the site of the double strand break. Mechanisms involve rejoining of what remains of the two DNA ends through direct re-ligation (Critchlow and Jackson 1998) or via the so-called microhomology-mediated end joining (Ma, Kim et al. 2003). Repair via non-homologous end joining (NHEJ) often results in small insertions or deletions and can be used for the creation of specific gene knockouts. There are numerous applications of genome engineering by site-specific nucleases extending from basic research to bioindustrial applications and human therapeutics. Re-engineering a DNA-binding protein for this purpose has been mainly limited to the naturally occurring LADLIDADG homing endonuclease (LHE), artificial zinc finger proteins (ZFP), the Transcription Activator-Like Effectors nucleases (TALE-nucleases), and the recently described CRISPR-Cas system.

Homing endonucleases, also known as meganucleases, are sequence-specific endonucleases with large (>14 bp) cleavage sites that can deliver DNA double-strand breaks at specific loci (Thierry and Dujon 1992). There are a handful of known homing endonuclease families which are demarcated on the basis of canonical motifs and the structural features which comprise them. However, they all share the property of recognizing and cleaving long DNA targets. Homing endonucleases were the first, and to date only, naturally occurring endonucleases with specificities at or approaching 'genome level', meaning having putative target sequences that occur very infrequently, or perhaps singularly, in their host genome. As a general property, HEs have a moderate degree of fidelity to their DNA target sequences, such that most base pair substitutions to their DNA target sequences reduce or eliminate the ability of the HE to bind or cleave it. HEs are therefore the most specific naturally occurring endonucleases yet discovered, and indeed this property is critical to the natural life cycle of the genetic elements in which they are encoded.

Homing endonuclease genes (HEGs) are classified as a type of selfish genetic element, as their DNA recognition and cleavage activity can lead to a DNA repair event that results in the copying of the HEG into the cleavage site. This mechanism of horizontal gene transfer, referred to as 'homing' results in a super-Mendelian inheritance pattern. Using this mechanism, HEGs and their endonuclease gene products can spread rapidly within their host species populations, and have also spread throughout all kingdoms of life over evolutionary time. HEGs are most commonly found in highly conserved genomic locations that do not impart fitness costs on their host organisms, such as within introns or as non-disruptive N- or C-terminal fusions to host proteins.

The LAGLIDADG homing endonuclease family (LHE) comprises a group of compact (<320 amino acids) nucleases whose structural and mechanistic properties have been studied extensively owing to their attractive properties for genome engineering applications. LHEs operate either as dimers or as pseudo-dimeric monomers, with the DNA cleaving active site occurring at the DNA-facing end of the interface of the two subunits (in dimeric LHEs) or domains (in monomeric LHEs). The LAGLIDADG consensus motifs for which LHEs are named are found in the two central alpha helices which form this interface between the two subunits or domains. At the bottom of each LAGLIDADG helix are the residues which together coordinate the hydrolysis reaction if the appropriate conditions are met, such as if the LHE finds and binds to an appropriate DNA target sequence. The active site covers the 'central-4' DNA bases of the DNA target sequence.

On either side of the active site are the two DNA binding domains LHEs use to recognize their DNA target sequences. Each domain comprises an anti-parallel beta sheet which wraps around nearly a complete turn of DNA and contacts 9 base pairs of DNA sequence. Members of the LHE family thus recognize 22 base pair DNA target sequences (9 base pairs for each domain, and 4 base pairs covered by the active site), which are partially palindromic in the case of dimeric LHEs, but can be entirely asymmetric for monomeric LHEs. Emanating from each anti-parallel beta sheet are the amino acid side chains which comprise the DNA recognition interface. While there is much amino acid conservation throughout the non-DNA interfacing residues amongst the LHE family, DNA recognition interface amino acid compositions vary significantly. This is because for each LHE the DNA recognition interface comprises an extensive network of side chain-to-side chain and side chain-to-DNA contacts, most of which is necessarily unique to a particular LHE's DNA target sequence. The amino acid composition of the DNA recognition interface (and the correspondence of it to a particular DNA sequence) is therefore the definitive feature of any natural or engineered LHE. The DNA recognition interface functions in determining the identity of the DNA target sequence which can be accommodated and hydrolyzed and also the affinity and specificity properties which define the quality of the LHE according to the demands of the application.

Owing to their small size and exquisite specificity properties, LHEs have been the subject of numerous efforts to engineer their DNA recognition properties with the desired outcome of cleaving and altering genes of interest in research, biotechnology, crop science, global health, and human therapeutics applications. However, the extent of the networks of residues which form the DNA recognition interface has generally prevented efficient methods for re-addressing LHEs to DNA target sequences of interest. This has led to continued innovation in field of gene-specific nuclease engineering, with three endonuclease alternative platforms now validated as having the capacity to target DNA sequences with ranging (but generally high) levels of specificity, as well as new and improved methods for overcoming the challenges of engineering the DNA recognition interfaces of LHEs.

Zinc finger nucleases (ZFNs) generating by fusing a plurality of Zinc finger-based DNA binding domains to an independent catalytic domain (Kim, Cha et al. 1996; Smith, Berg et al. 1999; Smith, Bibikova et al. 2000) represent another type of engineered nuclease commonly used to stimulate gene targeting and have been successfully used to induce gene correction, gene insertion and gene deletion in research and therapeutic applications. The archetypal ZFNs are based on the catalytic domain of the Type IIS restriction enzyme FokI and Zinc Finger-based DNA binding domains made of strings of 3 or 4 individual Zinc Fingers, each recognizing a DNA triplet (Pabo, Peisach et al. 2001). Two Zinc Finger-FokI monomers have to bind to their respective Zinc Finger DNA-recognition sites on opposite strands in an inverted orientation in order to form a catalytically active dimer that catalyze double strand cleavage (Bitinaite, Wah et al. 1998).

Transcription activator-like effectors (TALEs) were the next artificial endonuclease platform. TALEs derived from a family of proteins used in the infection process by plant pathogens of the *Xanthomonas* or *Ralstonia* genus are repetitive proteins characterized by 14-20 repeats of 33-35 amino acids differing essentially by two positions. Each base pair in the DNA target is contacted by a single repeat, with the specificity resulting from the two variant amino acids of the repeat (the so-called repeat variable dipeptide, RVD). The apparent modularity of these DNA binding domains has been confirmed to a certain extent by modular assembly of designed TALE-derived protein with new specificities (Boch, Scholze et al. 2009; Moscou and Bogdanove 2009). Very similarly to ZFNs, TALEs were readily adapted into site-specific nucleases by arraying TALE repeats with RVDs corresponding to the target sequence of choice and fusing the resultant array to a FokI domain. As such, DNA cleavage by a TALE-Nuclease requires two DNA recognition regions flanking an unspecific central region. TALE nucleases have proliferated widely since 2010 owing to their ease of production and improved double-strand break generating efficiency.

Of these distinct technologies, it is important to distinguish the advantaged properties of each and to determine innovative ways to capture these properties for the appropriate genome engineering applications. One of the most powerful applications of site-specific nuclease technology is in the field of human therapeutics. In one prominent genome engineering strategy to treat human immunodeficiency virus type-1 (HIV-1), site-specific nucleases have been developed to target the CCR5 gene. The CCR5 gene encodes the primary co-receptor which HIV-1 uses to enter into human T cells. Longstanding genetic and experimental evidence has shown that individuals who are homozygous for a disruption allele of CCR5 (the CCR5$^{\Delta 32}$ allele) are almost completely resistant to HIV-1 infection. Moreover, a recent clinical case file demonstrated that an HIV-1 infected patient transplanted with bone marrow from a donor homozygous for the CCR5$^{\Delta 32}$ allele was eradicated of his HIV-1 infection—the first confirmed case of an HIV-1 cure. These findings beget the development of improved, scalable genome engineering strategies targeting the CCR5 gene.

ZFN reagents have been evaluated in early phase clinical trials focused on disrupting the CCR5 gene in the T cells of HIV-1 patients. Early proof-of-concept results have shown that nuclease-mediated CCR5 gene disruption leads to promising clinical responses. Unfortunately, these results have been mitigated by the low efficiency of disruption, leading to difficulties in manufacturing biallelic CCR5 disrupted T cells, and also reports of poor ZFN specificity characteristics, which bring into question the safety of these particular nuclease reagents. Improvements in the efficiency, specificity, and manufacturability of a nuclease-based genome engineering strategy targeting the CCR5 gene are manifest if this approach is capable of producing 'functional cures' for HIV-1 infection.

SUMMARY OF THE INVENTION

A genome engineering strategy to treat human HIV-1 requires the use of safe and effective endonucleases for disrupting CCR5 gene. The endonuclease I-OnuI encoded within a group I intron in the Rps3 host gene from *Ophiostoma novo-ulmi* subsp *americana*, and its closely related homologs, have been recently characterized to be monomeric proteins displaying the characteristics of the LAGLIDADG homing endonucleases and to be sufficiently active for use in genome editing (WO2011/156430, (Sethuraman, Majer et al. 2009; Takeuchi, Lambert et al. 2011)).

In particular aspects, several I-OnuI variants were created in an attempt to target different DNA sequences in the CCR5 gene. In additional aspects, new LHE variants targeting the CCR5 gene at the boundary of the sixth transmembrane helix and the final extracellular loop are provided. These particular I-OnuI variants unexpectedly showed much higher efficiency in disrupting the expression of CCR5 in T-cells, while causing much less cell toxicity than the previous ones. In further aspects, these particular variants of the invention were then fused to some engineered nucleic acid binding domains, so as to form chimeric endonucleases that also showed improved properties, especially increases in specificity and efficiency which are required for obtaining safe and useful reagents for treating primary human cells. These molecules have proven efficiency for genome editing at the CCR5 locus and will be useful in methods for treating HIV infection.

DETAILED DESCRIPTION OF THE INVENTION

Unless specifically defined herein, all technical and scientific terms used have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, N.Y.: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

I-Onul and I-Onul Homologues Variants

The present invention relates to rare-cutting endonucleases involving I-Onul variants and I-Onul homologues variants of I-LtrI, I-LtrWI, I-PanMI, I-PanMII, I-PanMIII, I-GzeI, I-GzeMII, I-GzeMIII, I-GpiI, I-GpeMI, I-AabMI, I-AaeMI, I-ApaMI, I-CpaMI, I-CpaMII, I-CpaMIII, I-CpaMIV, I-CpaMV, I-EjeMI, I-CkaMI, I-CraMI, I-MpeMI, I-MveMI, I-NcrMI, I-OheMI, I-OsoMI, I-OsoMII, I-OsoMIII, I-OsoMIV, I-SmaMI, I-SscMI, I-Vdi141I, I-PnoMI or I-ScuMI (Takeuchi, Lambert et al. 2011)) able to specifically target a nucleic acid sequence present in the CCR5 gene.

The rare-cutting endonucleases according to the present invention refer to variant enzymes capable of catalyzing the hydrolysis (cleavage) of bonds between nucleic acids within a DNA or RNA molecule, preferably a DNA molecule. The endonucleases according to the present invention recognize and cleave nucleic acids at specific polynucleotide sequences, further referred to as the "nucleic acid target sequence".

To engineer rare-cutting endonucleases specific for target sites in the CCR5 gene, the inventors constructed libraries of I-Onul variants in which amino acid residues localized in the DNA recognition interface of natural I-Onul were varied. The libraries were screened for target cleavage activity against each predicted CCR5 target sites using previously described cleavage assays (Jarjour, West-Foyle et al. 2009). The specificity of the DNA recognition interface of I-Onul was thus altered to target sequences present in the human CCR5 gene.

By "variant(s)", is meant a protein or a polynucleotide encoding thereof that do not naturally exist in nature and that are obtained by genetic engineering or by random mutagenesis. I-Onul or I-Onul homologue variants according to the invention can for example be obtained by deletion or substitution with a different amino acid of at least one residue in the amino acid sequence of their wild-type sequences. Substitution(s) and deletions can for example be introduced by directed mutagenesis and/or by random mutagenesis. In the frame aspects of the present invention, I-Onul or I-Onul homologues variants have the ability to target CCR5 gene, which mean that they can interact with some specific DNA sequences encoding said gene.

The variants or homologues according to the invention comprise the DNA recognition interface as described herein and as provided in Table 1.

A DNA recognition interface refers to the residues of the protein domains of homing endonuclease or variant thereof which interact with nucleic acid target bases as well as those residues that are adjacent. For each homing endonuclease, the DNA recognition interface comprises an extensive network of side chain-to-side chain and side chain-to-DNA contacts, most of which is necessarily unique to recognize a particular nucleic acid target sequence. Thus, the DNA recognition interface amino acid compositions (and the correspondence of it to a particular nucleic acid sequence) vary significantly and is therefore the definitive feature of any natural or engineered homing endonuclease.

According to the present invention, the I-Onul or I-Onul homologue variants comprise one or more substitutions in the DNA recognition interface. Accordingly, the I-Onul variant or homologue according to the present invention has at least 70%, more preferably at least 75%, more preferably at least 80%, more preferably at least 85%, more preferably at least 90%, more preferably at least 95%, more preferably at least 97%, more preferably at least 99% sequence identity with the DNA recognition interface of I-Onul (Takeuchi, Lambert et al. 2011).

In a particular embodiment, said I-Onul or I-Onul homologue variants comprise one or more substitution(s) and/or mutations in the DNA recognition interface, particularly in the subdomains situated from positions 24-50, 68 to 82, 180 to 203 and 223 to 240 of I-Onul (SEQ ID NO: 2). The I-Onul variant or homologue can also comprise one or more substitutions at additional positions situated anywhere within the entire I-Onul sequence. The residues which are substituted and/or mutated may include residues contacting the nucleic acid target or interacting with the nucleic acid backbone or with the nucleotide bases, directly or via a water molecule as described in Takeuchi, Lambert et al. 2011.

For example, said I-Onul variant comprises one or more substitutions and/or mutations, preferably at least 10, preferably at least 15, more preferably at least 20, even more preferably at least 25 in at least one position selected from the position group consisting of positions: 19, 24, 26, 28, 30, 32, 34, 35, 36, 37, 38, 40, 42, 44, 46, 48, 68, 70, 72, 75, 76 77, 78, 80, 82, 168, 180, 182, 184, 186, 188, 189, 190, 191, 192, 193, 195, 197, 199, 201, 203, 223, 225, 227, 229, 231, 232, 234, 236, 238, 240 of I-Onul (SEQ ID NO: 2). In particular embodiments, said substitutions and/or mutations are replacement of at least one of the initial amino acids, in each case with an amino acid selected from the group consisting of: A, D, E, G, H, K, N, P, Q, R, S, T, Y, C, V, L, W, M and I.

As non-limiting examples, the alanine (A) at position 19 may be replaced by/mutated to threonine (T), the leucine (L) at position 26 may be replaced by/mutated to methionine (M); the asparagine (N) at position 32 may be replaced by/mutated to threonine (T); the lysine (K) at position 34 may be replaced by/mutated to asparagine (N); the serine (S) at position 35 may be replaced by/mutated to arginine (R); the serine (S) at position 36 may be replaced by/mutated to threonine (T); the serine (S) t position 40 may be replaced by/mutated to tyrosine (Y); the glutamic acid (E) at position 42 may be replaced by/mutated to serine (S); the glycine (G) at position 44 may be replaced by/mutated to valine (V); the glutamine (Q) t position 46 may be replaced by/mutated to glutamic acid (E) (see Table1).

The valine (V) at position 68 may be replaced by/mutated to threonine (T); the alanine (A) at position 70 may be replaced by/mutated to asparagine (N); the serine (S) t position 72 may be replaced by/mutated to arginine (R); the asparagine (N) at position 75 may be replaced by/mutated to glycine (G); the alanine (A) at position 76 may be replaced by/mutated to threonine (T); the valine (V) at position 77 may be replaced by/mutated to alanine (A); the serine (S) at position 78 may be replaced by/mutated to arginine (R); the lysine (K) t position 80 may be replaced by/mutated to serine (S) (see Table1).

The phenylalanine (F) at position 168 may be replaced by/mutated to leucine (L); the cysteine (C) at position 180 may be replaced by/mutated to threonine (T); the phenylalanine (F) at position 182 may be replaced by/mutated to tyrosine (Y); the asparagine (N) at position 184 may be replaced by/mutated to histidine (H); the isoleucine (I) at position 186 may be replaced by/mutated to alanine (A); the lysine (K) t position 189 may be replaced by/mutated to glutamic acid (E); the serine (S) t position 190 may be replaced by/mutated to alanine (A); the lysine (K) at position 191 may be replaced by/mutated to serine (S); the leucine (L) at position 192 may be replaced by/mutated to glycine (G); the glycine (G) t position 193 may be replaced by/mutated to lysine (K); the glutamine (Q) t position 195 may be replaced by/mutated to tyrosine (Y); the glutamine (Q) at position 197 may be replaced by/mutated to arginine (R); the valine (V) at position 199 may be t arginine (R); the serine (S) t position 201 may be replaced by/mutated to isoleucine (I); the threonine (T) t position 203 may be replaced by/mutated to glycine (G) (see Table1)

The tyrosine (Y) at position 223 may be replaced by/mutated to lysine (K) or threonine (T); the lysine (K) at position 225 may be replaced by/mutated to glutamine (Q); the lysine (K) at position 229 may be replaced by/mutated to arginine (R); the glutamic acid (E) t position 231 may be replaced by/mutated to lysine (K); the phenylalanine (F) at position 232 may be replaced by/mutated to glycine (G); the tryptophane (W) at position 234 may be replaced by/mutated to methionine (M); the aspartic acid (D) t position 236 may be replaced by/mutated to histidine (H); the valine (V) t position 238 may be replaced by/mutated to isoleucine (I) (see table 1).

In a more preferred embodiment the I-OnuI variant comprises the protein sequence selected from the group consisting of SEQ ID NO: 12, SEQ ID NO: 15, SEQ ID NO:17 and SEQ ID NO: 19 and SEQ ID NO.31.

In a preferred embodiment, the I-OnuI or I-OnuI homologue variant according to the present invention has at least 70%, more preferably at least 75%, more preferably at least 80%, more preferably at least 85%, more preferably at least 90%, more preferably at least 95%, more preferably at least 97%, more preferably at least 99% sequence identity with the protein sequence SEQ ID NO: 12, SEQ ID NO: 15, SEQ ID NO: 17 and SEQ ID NO: 19.

According to a preferred embodiment of the invention the I-OnuI or I-OnuI homologues variants according to the invention cleave a target sequence that is different from the target sequence of the corresponding wild-type endonuclease. Cleavage in the nucleic acid target sequence can correspond to either a double-stranded break or a single-stranded break The present invention is based on the finding that such variant endonucleases with novel specificities can be used to allow efficient targeted modification of the CCR5 gene.

The present inventors have indeed identified putative I-OnuI target sequences in the human CCR5 gene based on a series of common features intrinsic to the group of monomeric I-OnuI-like LHE subfamily members recently described in (Takeuchi, Lambert et al. 2011; Baxter, Lambert et al. 2012). The putative LHE target sequences are also identified on the basis of the locations within CCR5 gene wherein endonuclease-mediated insertions or deletions can cause significant disruptions to the CCR5 protein. As an additional consideration, optimal targets were selected which contained adjacent downstream stop codons in alternative reading frames, which would therefore be expressed following NHEJ-mediated base pair insertions/deletions to prevent the production of long out-of-frame peptides which could serve as the basis for immunological rejection. The present inventors identified six putative target sequences in the human CCR5 gene (SEQ ID NO: 3 to SEQ ID NO: 8) upon which the DNA recognition interface of the I-OnuI variants were engineered. Among these six putative target sites, only two sequences (CCR5_S02 and CCR5_S08) have been successfully targeted by the resulting I-OnuI variants, but only those targeting CCR5_S08 have appeared not being toxic (see experimental results).

Accordingly, the present invention relates to a rare-cutting endonuclease comprising an I-OnuI or I-OnuI homologue variant that recognizes a target nucleic acid sequence present within CCR5 gene, preferably those present in the exon 4 of the CCR5 gene, more preferably a target nucleic acid sequence comprising nucleic acid sequence SEQ ID NO: 5.

Chimeric Endonucleases

In another aspect, the invention relates to a rare-cutting endonuclease under the form of chimeric endonuclease comprising an I-OnuI or I-OnuI homologue variant as described above, optionally fused to at least one additional protein domain, by a peptide linker. The additional protein domain may be selected from the group consisting of: a nucleic acid binding domain to allow higher specificity on target nucleic acid sequence and avoid off target site; a catalytic domain to process (eg. polymerize, depolymerize, modify) target nucleic acid sequence; and one or more terminal epitope tags or fluorescent proteins to follow and visualize the chimeric protein.

In a particular embodiment, the I-OnuI or I-OnuI homologue variant is fused to a nucleic acid binding domain such as TALE nucleic acid binding domain as non-limiting example to improve CCR5 gene targeting.

Said Transcription Activator like Effector (TALE) corresponds to an engineered TALE comprising a plurality of TALE repeat sequences, each repeat comprising a RVD specific to each nucleotide base of a TALE recognition site. In the present invention, each TALE repeat sequence of said TALE is made of 30 to 42 amino acids, more preferably 33 or 34 wherein two critical amino acids (the so-called repeat variable dipeptide, RVD) located at positions 12 and 13 mediates the recognition of one nucleotide of said TALE binding site sequence; equivalent two critical amino acids can be located at positions other than 12 and 13 particularly in TALE repeat sequence larger than 33 or 34 amino acids long. Preferably, RVDs associated with recognition of the different nucleotides are HD for recognizing C, NG for recognizing T, NI for recognizing A, NN for recognizing G or A, NS for recognizing A, C, G or T, HG for recognizing T, IG for recognizing T, NK for recognizing G, HA for recognizing C, ND for recognizing C, HI for recognizing C, HN for recognizing G, NA for recognizing G, SN for recognizing G or A and YG for recognizing T, TL for recognizing A, VT for recognizing A or G and SW for recognizing A. In another embodiment, critical amino acids 12 and 13 can be mutated towards other amino acid residues in order to modulate their specificity towards nucleotides A, T, C and G and in particular to enhance this specificity. By other amino acid residues is intended any of the twenty natural amino acid residues or unnatural amino acids derivatives.

In another embodiment, said TALE of the present invention comprises between 5 and 30 TALE repeat sequences. More preferably, said TALE of the present invention comprises between 8 and 20 TALE repeat sequences; again more preferably 10 TALE repeat sequences.

In another embodiment, said TALE comprises an additional single truncated TALE repeat sequence made of 20 amino acids located at the C-terminus of said set of TALE repeat sequences, i.e. an additional C-terminal half-TALE repeat sequence. In this case, said TALE of the present invention comprises between 5.5 and 30.5 TALE repeat sequences, "0.5" referring to previously mentioned half-TALE repeat sequence (or terminal RVD, or half-repeat). More preferably, said TALE of the present invention comprises between 5.5 and 20.5 TALE repeat sequences, again more preferably, 10.5 TALE repeat sequences. In a preferred embodiment, said half-TALE repeat sequence is in a TALE context which allows a lack of specificity of said half-TALE repeat sequence toward nucleotides A, C, G, T. In a more preferred embodiment, said half-TALE repeat sequence is absent. In another embodiment, said TALE of the present invention comprises TALE like repeat sequences of different origins. In a preferred embodiment, said TALE comprises TALE like repeat sequences originating from different naturally occurring TAL effectors. In another preferred embodiment, internal structure of some TALE like repeat sequences of the TALE of the present invention are constituted by structures or sequences originated from different naturally occurring TAL effectors. In another embodiment, said TALE of the present invention comprises TALE like repeat sequences. TALE like repeat sequences have a sequence different from naturally occurring TALE repeat sequences but have the same function and/or global structure within said core scaffold of the present invention.

The chimeric endonuclease according to the invention can therefore correspond to the fusion of an I-Onul variant or I-Onul homologue variant as previously described to a modular nucleic acid binding domain, such as a TALE or a zinc-finger domain, said fusion being active under monomeric form, as part as a single chain polypeptide.

According to a further aspect of the invention, the protein domain fused to the I-Onul variant or I-Onul homologue variant may have at least one catalytical activity selected from the group consisting of: nuclease activity, polymerase activity, kinase activity, phosphatase activity, methylase activity, topoisomerase activity, integrase activity, transposase activity, ligase activity, helicase activity, recombinase activity. In a preferred embodiment, protein domain has an endonuclease activity, whereas the I-Onul variant retains its own cleavage activity or solely retains binding affinity to CCR5; in another preferred embodiment, said protein domain is or comprises an exonuclease activity. As non-limiting examples, catalytic domains may be or comprise in part one of the proteins selected in the group consisting of: MmeI, Colicin-E7 (CEA7_ECOLX), Colicin-E9, APFL, EndA, Endo I (END1_ECOLI), Human Endo G (NUC-G_HUMAN), Bovine Endo G (NUCG_BOVIN), R.HinPlI, I-BasI, I-BmoI, I-HmuI, I-TevI, I-TevII, I-TevIII, I-TwoI, R.MspI, R.MvaI, NucA, NucM, Vvn, Vvn_CLS, Staphylococcal nuclease (NUC_STAAU), Staphylococcal nuclease (NUC_STAHY), Micrococcal nuclease (NUC_SHIFL), Endonuclease yncB, Endodeoxyribonuclease I (ENRN_BPT7), Metnase, Nb.BsrDI, BsrDI A, Nt.BspD6I (R.BspD6I large subunit), ss.BspD6I (R.BspD6I small subunit), R.PleI, MlyI, AlwI, Mva1269I, BsrI, BsmI, Nb.BtsCI, Nt.BtsCI, R1.BtsI, R2.BtsI, BbvCI subunit 1, BbvCI subunit 2, Bpu10I alpha subunit, Bpu10I beta subunit, BmrI, BfiI, I-CreI, hExoI (EXO1_HUMAN), Yeast ExoI (EXO1_YEAST), *E. coli* ExoI, Human TREX2, Mouse TREX1, Human TREX1, Bovine TREX1, Rat TREX1, Human DNA2, Yeast DNA2 (DNA2_YEAST), TdT and VP16 or a functional mutant thereof.

In a preferred embodiment, the catalytic domain is a DNA end-processing enzyme. Non limiting examples of DNA end-processing enzymes include 5-3' exonucleases, 3-5' exonucleases, 5-3' alkaline exonucleases, 5' flap endonucleases, helicases, phosphatase, hydrolases and template-independent DNA polymerases. In a more preferred embodiment, said catalytic domain has an exonuclease activity, in particular a 3'-5' exonuclease activity. In a more preferred embodiment, said catalytic domain is TREX2 or a functional variant thereof. In another preferred embodiment, said catalytic domain is encoded by a single chain TREX2 polypeptide. In a particular embodiment, said catalytic domain is fused to the N-terminus or C-terminus of said rare-cutting endonuclease. In a more preferred embodiment, said catalytic domain is fused to said rare-cutting endonuclease by a peptide linker.

In particular aspects, peptide linkers act as a communication device/linking or joining element between the rare-cutting endonuclease and an additional protein domain to act in concert for activity. Said peptide linker provides a peptide sequence which allows the connection of different monomers in a fusion protein and the adoption of the correct conformation for said fusion protein activity, but does not alter the specificity of either of the monomers for their targets. Peptide linkers can be of various sizes, from 2 amino acids to 50 amino acids as a non-limiting indicative range. Peptide linkers can also be structured or unstructured.

Alternatively, the I-Onul variant or I-Onul homologue variant according to the invention is used in conjunction with another protein not being fused thereto, having the same catalytic activity as the protein domain described above.

Another aspect of the invention provides polynucleotides comprising nucleic acid sequence encoding the rare-cutting endonucleases, preferably I-Onul variants, homologues or chimeric endonuclease as described herein and vectors comprising such polynucleotides. Nucleic acid or vectors according to additional aspects of the present invention can comprise a nucleic acid sequence encoding one or more subcellular localization motifs, protease cleavage sites or ribosomal skip sequences.

In particular embodiments, the nucleic acids of the present invention can comprise at least one subcellular localization motif. A subcellular localization motif refers to a sequence that facilitates transporting or confining a protein to a defined subcellular location that includes at least one of the nucleus, cytoplasm, plasma membrane, endoplasmic reticulum, golgi apparatus, endosomes, peroxisomes and mitochondria. Subcellular localization motifs are well-known in the art. A Subcellular localization motif requires a specific orientation, e.g., N- and/or C-terminal to the protein. As a non-limiting example, the nuclear localization signal (NLS) of the simian virus 40 large T-antigen can be oriented at the N and/or C-terminus. NLS is an amino acid sequence which acts to target the protein to the cell nucleus through Nuclear Pore Complex and to direct a newly synthesized protein into the nucleus via its recognition by cytosolic nuclear transport receptors. Typically, a NLS consists of one or more short sequences of positively charged amino acids such as lysines or arginines.

Methods of Genome Engineering

Another aspect of the invention concerns the use of I-OnuI variant, I-OnuI homologue variant or I-OnuI derived chimeric endonuclease as described above to allow efficient CCR5 gene targeting in a cell. More particularly, the invention relates to a method for targeted modification in the CCR5 gene in a cell comprising introducing into a cell the rare-cutting endonuclease or chimeric endonuclease as described above. In a particular embodiment, the present invention relates to a method for modifying the CCR5 gene in a cell comprising, introducing into the cell the rare-cutting endonuclease more particularly the I-OnuI variant, I-OnuI homologue variant or chimeric endonuclease, such that the rare-cutting endonuclease cleaves a nucleic acid target sequence in CCR5 gene.

According to a further embodiment of the invention, the rare-cutting endonuclease is expressed into a cell in order to obtain targeted mutagenesis at the CCR5 locus. The nucleic acid strand breaks caused by the rare-cutting endonuclease are commonly repaired through the distinct mechanisms of homologous recombination or non-homologous end joining (NHEJ). However, NHEJ is an imperfect repair process that often results in changes to the DNA sequence at the site of the double strand break. Mechanisms involve rejoining of what remains of the two DNA ends through direct re-ligation (Critchlow and Jackson 1998) or via the so-called microhomology-mediated end joining (Ma, Kim et al. 2003). Repair via non-homologous end joining (NHEJ) often results in small insertions or deletions and can be used for the creation of specific gene knockouts. Said modification may be a substitution, deletion, or addition of at least one nucleotide. Cells in which a cleavage-induced mutagenesis event, i.e a mutagenesis event consecutive to an NHEJ event, has occurred can be identified and/or selected by well-known method in the art. As a non-limiting example, deep-sequencing analysis can be generated from the targeted cell genome around the targeted locus. Insertion/deletion events (mutagenesis events) can be therefore detected. As another non-limiting example, assays based on T7 endonuclease that recognizes non-perfectly matched DNA can be used, to quantify from a locus specific PCR on genomic DNA from provided cells, mismatches between reannealed DNA strands coming from cleaved/non-cleaved DNA molecules In a particular embodiment of the methods envisaged herein the mutagenesis is increased by introducing into the cell an additional catalytic domain. In a particular embodiment, the present invention provides improved methods for ensuring targeted modification in the CCR5 gene and provides a method for increasing mutagenesis at the target CCR5 nucleic acid sequence to generate at least one nucleic acid cleavage and a loss of genetic information around said target nucleic acid sequence thus preventing any scarless re-ligation by NHEJ. In a more preferred embodiment, said catalytic domain is a DNA end-processing enzyme. Non limiting examples of DNA end-processing enzymes include 5-3' exonucleases, 3-5' exonucleases, 5-3' alkaline exonucleases, 5' flap endonucleases, helicases, hosphatase, hydrolases and template-independent DNA polymerases. Non limiting examples of such catalytic domain comprise at least one protein domain or catalytically active derivative of the protein domain selected from the group consisting of hExoI (EXO1_HUMAN), Yeast ExoI (EXO1_YEAST), *E. coli* ExoI, Human TREX2, Mouse TREX1, Human TREX1, Bovine TREX1, Rat TREX1, TdT (terminal deoxynucleotidyl transferase) Human DNA2, Yeast DNA2 (DNA2_YEAST). In a more preferred embodiment, said catalytic domain has an exonuclease activity, in particular a 3'-5' exonuclease activity. In a more preferred embodiment, said catalytic domain is TREX2 or functional variant thereof. In another preferred embodiment, said catalytic domain is encoded by a single chain TREX polypeptide. In a particular embodiment, said catalytic domain is fused to the N-terminus or C-terminus of said rare-cutting endonuclease. It has been found that the coupling of the enzyme TREX2 or single chain TREX2 with an endonuclease such as a meganuclease ensures high frequency of targeted mutagenesis. Alternatively, the above catalytic domain can be separately brought into the cell as part of an independent protein.

Endonucleolytic breaks are known to stimulate homologous recombination. Therefore, in particular embodiments, the present invention also relates to a method for inducing homologous gene targeting in the target nucleic acid sequence further comprising introducing into the cell a donor matrix comprising a sequence homologous to at least a portion of the target CCR5 gene, such that homologous recombination occurs between the target nucleic acid sequence and the donor matrix.

In particular embodiments, homologous CCR5 gene targeting is achieved by introducing into a cell a rare-cutting endonuclease as described above, to induce a cleavage within or adjacent to a nucleic acid target sequence, as well as a donor matrix comprising a transgene to introduce said transgene by homologous recombination. Following cleavage of the target nucleic acid sequence, a homologous recombination event is stimulated between the genome containing the target nucleic acid sequence and the donor matrix. Said donor matrix comprises a sequence homologous to at least a portion of the target nucleic acid sequence, such that homologous recombination occurs between the target nucleic acid sequence and the donor matrix. Preferably, homologous sequences of at least 50 bp in length, preferably more than 100 bp and more preferably more than 200 bp are used within said donor matrix. Therefore, the donor matrix is preferably from 200 bp to 6000 bp in length, more preferably from 1000 bp to 2000 bp. In another embodiment, said donor matrix comprises two sequences homologous to portions or adjacent portions of said target nucleic acid sequence flanking a sequence to introduce in the target nucleic acid sequence. Indeed, shared DNA homologies are located in regions flanking upstream and downstream the site of the break and the nucleic acid sequence to be introduced should be located between the two homology arms. In particular embodiments, said donor matrix comprises first and second portions which are homologous to region 5' and 3' of the target nucleic acid, respectively. Said donor matrix in these embodiments can also comprise a third portion positioned between the first and the second portion which comprises little or no homology with the regions 5' and 3' of the site of DNA cleavage. In this case, said donor matrix allows introducing new genetic material into a cell. Said new genetic material introduced into a cell can confer a selective or a commercial advantage to said cell. In another embodiment, said donor matrix allows to replace genetic material into a cell. In another embodiment, said donor matrix allows to repair genetic material into a cell.

In particular embodiments, said donor matrix can comprise a positive selection marker between the two homology arms and eventually a negative selection marker upstream of the first homology arm or downstream of the second homology arm. The marker(s) allow(s) the selection of cells having inserted the sequence of interest by homologous recombination at the target site. Depending on the location of the targeted genome sequence wherein cleavage event has occurred, such donor matrix can be used to knock-out a gene, e.g. when the donor matrix is located within the open reading frame of said gene, or to introduce new sequences or genes of interest. Sequence insertions by using such donor matrix can be used to modify a targeted existing gene, by correction or replacement of said gene (allele swap as a non-limiting example), or to up- or down-regulate the expression of the targeted gene (promoter swap as non-limiting example), said targeted gene correction or replacement.

Cells in which a homologous recombination event has occurred can be selected by methods well-known in the art. As a non-limiting example, PCR analysis using one oligonucleotide matching within the exogenous nucleic acid sequence and one oligonucleotide matching the genomic nucleic acid of cells outside said exogenous nucleic acid but close to the targeted locus can be performed. Therefore, cells in which methods of the invention allowed a mutagenesis event or a homologous recombination event to occur can be selected.

The different methods of the invention involve introducing rare-cutting endonuclease or chimeric endonuclease optionally with DNA-end processing enzyme or donor matrix into a cell. As non-limiting example, said rare-cutting endonuclease or chimeric endonuclease optionally with DNA-end processing enzyme or donor matrix can be introduced as transgenes encoded by one or as different plasmidic vectors. Different transgenes can be included in one vector which comprises a nucleic acid sequence encoding ribosomal skip sequence such as a sequence encoding a 2A peptide. 2A peptides, which were identified in the Aphthovirus subgroup of picornaviruses, causes a ribosomal "skip" from one codon to the next without the formation of a peptide bond between the two amino acids encoded by the codons (see Donnelly et al., J. of General Virology 82: 1013-1025 (2001); Donnelly et al., J. of Gen. Virology 78: 13-21 (1997); Doronina et al., Mol. And. Cell. Biology 28(13): 4227-4239 (2008); Atkins et al., RNA 13: 803-810 (2007)). By "codon" is meant three nucleotides on an mRNA (or on the sense strand of a DNA molecule) that are translated by a ribosome into one amino acid residue. Thus, two polypeptides can be synthesized from a single, contiguous open reading frame within an mRNA when the polypeptides are separated by a 2A oligopeptide sequence that is in frame. Such ribosomal skip mechanisms are well known in the art and are known to be used by several vectors for the expression of several proteins encoded by a single messenger RNA. As non-limiting example, in the present invention, 2A peptides have been used to express into the cell the rare-cutting endonuclease and a DNA end-processing enzyme. As non-limiting examples, 2A peptide may be used to express into the cell the rare-cutting endonuclease or the chimeric endonuclease and an additional protein domain with a catalytical activity selected from the group consisting of nuclease activity, polymerase activity, kinase activity, phosphatase activity, methylase activity, topoisomerase activity, integrase activity, transposase activity, ligase activity, helicase activity, recombinase activity as to process target nucleic acid sequence. The 2A peptide may also be used to express into the cell the rare-cutting endonuclease or the chimeric endonuclease and a fluorescent protein.

Said plasmid vector can contain a selection marker which provides for identification and/or selection of cells which received said vector. Vectors can be introduced into a cell by a variety of methods (e.g., injection, direct uptake, projectile bombardment, liposomes, electroporation). Rare-cutting endonucleases, chimeric endonucleases, DNA-end processing enzyme or donor matrix according to the present invention can be stably or transiently expressed into cells using expression vectors. Techniques of expression in eukaryotic cells are well known to those in the art. (See Current Protocols in Human Genetics: Chapter 12 "Vectors For Gene Therapy" & Chapter 13 "Delivery Systems for Gene Therapy"). The polypeptide may be synthesized in situ in the cell as a result of the introduction of polynucleotide encoding polypeptide into the cell. Said protein expression can be induced in selected cells and said rare-cutting endonuclease or chimeric endonuclease cleaves target nucleic acid sequence in selected cells. Alternatively, the polypeptide could be produced outside the cell and then introduced thereto by well-known method of the art.

In another embodiment, said methods of the present invention can be used to generate animals or plants wherein a targeted double-stranded break occurred. Animals may be generated by introducing a rare-cutting endonuclease or a chimeric endonuclease according to the invention into a cell or an embryo. In particular, the present invention relates to a method for generating an animal, comprising providing an eukaryotic cell comprising a nucleic acid target sequence in CCR5 gene into which it is desired to introduce a genetic modification; generating a cleavage within or adjacent to the nucleic acid target sequence by introducing an engineered rare-cutting endonuclease or chimeric endonuclease according to the present invention; and generating an animal from the cell or progeny thereof, in which cleavage has occurred. Typically, the embryo is a fertilized one cell stage embryo. Polynucleotides encoding said rare-cutting endonuclease or chimeric endonuclease may be introduced into the cell by any of the methods known in the art including micro injection into the nucleus or cytoplasm of the embryo. In a particular embodiment, the method for generating an animal, further comprise introducing a donor matrix as desired. Said donor matrix comprises a sequence homologous to at least a portion of the nucleic acid target sequence, such that homologous recombination occurs between said donor matrix and the nucleic acid target sequence in the cell or progeny thereof. The donor matrix can include for example a nucleic acid sequence that disrupts a gene after homologous recombination, a nucleic acid sequence that replaces a gene after homologous recombination, a nucleic acid sequence that introduces a mutation into a gene after homologous recombination or a nucleic acid sequence that introduce a regulatory site after homologous recombination. The embryos are then cultured to develop an animal. In one aspect of the invention, an animal in which at least a nucleic acid target sequence of interest has been engineered is provided. For example, an engineered gene may become inactivated such that it is not transcribed or properly translated, or an alternate form of the gene is expressed. The animal may be homozygous or heterozygous for the engineered gene. More particularly, the present invention relates to a method for making an CCR5 knock-in or knock-out animal, comprising: a) introducing into a pluripotent precursor cell or embryo of an animal, a rare-cutting endonuclease or chimeric endonuclease as defined above sufficient/capable to induce a nucleic acid cleavage in the nucleic acid target present in CCR5 gene; (b) introducing Into the animal precursor cell or embryo of step (a), optionally a donor matrix, wherein said donor matrix comprises a sequence to be introduced flanked by at least one sequence sharing homologies with at least one region of the CCR5 gene surrounding the nucleic acid cleavage site of said rare-cutting endonuclease; (c) developing the genomically modified animal precursor cell or embryo of step (b) into a chimeric animal, and (d) deriving a transgenic animal from the chimeric animal of step (c). Preferably, step (c) comprises the introduction of the genomically modified precursors cells generated in step (b) into blastocysts so as to generate chimeric animals.

In another aspect, the present invention relates to an isolated cell comprising a gene encoding the CCR5 protein inactivated (e.g., with respect to typical CCR5 protein biogenesis and/or CCR5 protein cell surface expression and/or with respect to the CCR5 protein assisting viral infection) by the methods described above.

"Cell" or "cells" as used herein refers to any prokaryotic or eukaryotic living cells, cell lines derived from these organisms for in vitro cultures, primary cells from animal origin.

"Primary cell" or "primary cells" as used herein refers to cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines. These cells thus represent a more valuable model to the in vivo state they refer to.

More preferably the animal cell is of the genus *Homo, Rattus, Mus, Sus, Bos, Danio, Canis, Felis, Equus, Salmo, Oncorhynchus, Gallus, Meleagris, Drosophila, Caenorhabditis*; more preferably, the animal cell is of the species *Homo sapiens, Rattus norvegicus, Mus musculus, Sus scrofa, Bos taurus, Danio rerio, Canis lupus, Felis catus, Equus caballus, Salmo solar, Oncorhynchus mykiss, Gallus gallus, Meleagris gallopavo, Drosophila melanogaster, Caenorhabditis elegans*.

In aspects of the present invention, the cell can a mammalian cell, a or cell lines derived from these organisms for in vitro cultures or primary cells taken directly from living tissue and established for in vitro culture. As non-limiting examples cell lines can be selected from the group consisting of CHO-K1 cells; HEK293 cells; Caco2 cells; U2-OS cells; NIH 3T3 cells; NSO cells; SP2 cells; CHO-S cells; DG44 cells; K-562 cells, U-937 cells; MRC5 cells; IMR90 cells; Jurkat cells; HepG2 cells; HeLa cells; HT-1080 cells; HCT-116 cells; Hu-h7 cells; Huvec cells; Molt 4 cells.

In a more preferred embodiment, said isolated cells can be multipotent cells, for example stem cells. The stem cells can be adult stem cells, embryonic stem cells, more particularly non-human stem cells, cord blood stem cells, progenitor cells, bone marrow stem cells, induced pluripotent stem cells, totipotent stem cells or hematopoietic stem cells. Representative human cells are CD34+ cells. In a particular embodiment of the present invention, the cells are T-cells, preferably human T-cells.

Method for Treating or Preventing HIV Infection

In another aspect, the present invention relates to the use of the I-Onul variants, I-Onul homologue variants or I-Onul derived chimeric endonuclease according to the invention as a medicament.

More particularly, the present invention relates to a method for treating a subject having HIV infection comprising introducing into a cell a rare-cutting endonuclease or chimeric endonuclease according to the invention sufficient to provide for mutagenesis or homologous recombination in the CCR5 gene, optionally with a donor matrix and/or DNA-end processing enzyme, and administrating the cells to the subject. In particular aspects, the method can comprise selecting cultured cells in which the mutagenesis or homologous recombination event has occurred in the CCR5 gene by well-known methods in the art.

Said treatment can be ameliorating, curative or prophylactic. It may be either part of an autologous or part of an allogenic treatment. By autologous, it is meant that cells, cell line or population of cells used for treating patients are originating from said patient. By allogeneic is meant that the cells or population of cells used for treating patients are not originating from said patient but from a donor.

Cells that can be used with the disclosed methods can be multipotent cells, for example stem cells. The stem cells can be adult stem cells, embryonic stem cells, more particularly non-human stem cells, cord blood stem cells, progenitor cells, bone marrow stem cells, induced pluripotent stem cells, totipotent stem cells or hematopoietic stem cells. Representative human cells are CD34+ cells or human T-cells. Prior to expansion and genetic modification of the cells of the invention, a source of cells can be obtained from a subject through a variety of non-limiting methods. T cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available and known to those skilled in the art, may be used.

In another embodiment, isolated cells obtained by the different methods or cell line(s) derived from said isolated cells can be used as a medicament. In another embodiment, said medicament can be used for treating infections in a patient in need thereof. In another embodiment, said isolated cell according to the invention or cell line derived from said isolated cell can be used in the manufacture of a medicament for treatment of a viral infection in a patient in need thereof.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermaliy, intratumorally, intranodally, intramedullary, intramuscularly, by intravenous or intralymphatic injection, or intraperitoneally. In one embodiment, the cell compositions of the present invention are preferably administered by intravenous injection.

In particular aspects, the administration of the cells or population of cells comprises the administration of $10^4$ to $10^9$ cells/kg body weight, preferably $10^5$ to $10^6$ cells/kg body weight, including all values of cell numbers within those ranges. The cells or population of cells can be administrated in one or more doses. In another embodiment, said effective amount of cells are administrated as a single dose. In another embodiment, said effective amount of cells are administrated as more than one dose over a period time. Timing of administration is within the judgment of managing physician and depends on the clinical condition of the patient. The cells or population of cells may be obtained from any source, such as a cell bank or a donor. While individual needs vary, determination of optimal ranges of effective amounts of a given cell type for a particular disease or conditions within the skill of the art. The dosage administrated will be dependent upon the age, health and weight of the recipient, kind of concurrent treatment, if any, frequency of treatment and the nature of the effect desired.

In another embodiment, the present invention relates to a method for treating HIV infection in a subject, the method comprising administrating to a subject a vector encoding a rare-cutting endonuclease according to the present invention.

Definitions

In the description above, a number of terms are used extensively. The following definitions are provided to facilitate understanding of the present embodiments.

As used herein, the term "about" indicates that a value includes the inherent variation of error for the method being employed to determine a value, or the variation that exists among experiments.

- Amino acid residues in a polypeptide sequence are designated herein according to the one-letter code, in which, for example, Q means Gln or Glutamine residue, R means Arg or Arginine residue and D means Asp or Aspartic acid residue.
- Amino acid substitution means the replacement of one amino acid residue with another, for instance the replacement of an Arginine residue with a Glutamine residue in a peptide sequence is an amino acid substitution.
- Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.
- As used herein, "nucleic acid" or "nucleic acid molecule" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.
- by "chimeric endonuclease" it is intended to mean an endonuclease which comprise functional portions of an endonuclease operationally linked to one or more protein functional domains coming from another protein.
- The terms "fusion protein" or "chimeric protein" indicate that the protein includes polypeptide components derived from more than one parental protein or polypeptide. Typically, a fusion protein is expressed from a fusion gene in which a nucleotide sequence encoding a polypeptide sequence from one protein is appended in frame with, and optionally separated by a linker from, a nucleotide sequence encoding a polypeptide sequence from a different protein. The fusion gene can then be expressed by a host cell as a single protein. A fusion protein can comprise at least part of one polypeptide fused with another polypeptide. In some embodiments, a fusion protein can comprise at least a part of one polypeptide fused with at least a part of the same polypeptide.
- by "screening" it is intended to mean the sequential or simultaneous selection of one or more meganuclease variant(s) which exhibits a specified phenotype such as altered cleavage activity.
- by "mutation" is intended the substitution, deletion, insertion of one or more nucleotides/amino acids in a polynucleotide (cDNA, gene) or a polypeptide sequence. Said mutation can affect the coding sequence of a gene or its regulatory sequence. It may also affect the structure of the genomic sequence or the structure/stability of the encoded mRNA.
- By "gene" is meant the basic unit of heredity, consisting of a segment of DNA arranged in a linear manner along a chromosome, which codes for a specific protein or segment of protein. A gene typically includes a promoter, a 5' untranslated region, one or more coding sequences (exons), optionally introns, a 3' untranslated region. The gene may further comprise a terminator, enhancers and/or silencers.
- As used herein, the term "transgene" refers to a sequence encoding a polypeptide. Preferably, the polypeptide encoded by the transgene is either not expressed or expressed but not biologically active, in the cell, tissue or individual in which the transgene is inserted. Most preferably, the transgene encodes a therapeutic polypeptide useful for the treatment of an individual.
- By "delivery vector" or "delivery vectors" is intended any delivery vector which can be used in the present invention to put into cell contact (i.e "contacting") or deliver inside cells or subcellular compartments agents/chemicals and molecules (proteins or nucleic acids) needed in the present invention. It includes, but is not limited to liposomal delivery vectors, viral delivery vectors, drug delivery vectors, chemical carriers, polymeric carriers, lipoplexes, polyplexes, dendrimers, microbubbles (ultrasound contrast agents), nanoparticles, emulsions or other appropriate transfer vectors. These delivery vectors allow delivery of molecules, chemicals, macromolecules (genes, proteins), or other vectors such as plasmids, peptides developed by Diatos. In these cases, delivery vectors are molecule carriers. By "delivery vector" or "delivery vectors" is also intended delivery methods to perform transfection.
- The terms "vector" or "vectors" refer to a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e. g. adenoassociated viruses), coronavirus, negative strand RNA viruses such as orthomyxovirus (e.g., influenza virus), rhabdovirus (e.g., rabies and vesicular stomatitis virus), paramyxovirus (e. g. measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomega-lovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

by "lentiviral vector" is meant HIV-Based lentiviral vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells.

by "integrative lentiviral vectors (or LV)", is meant such vectors as non limiting example, that are able to integrate the genome of a target cell.

At the opposite by "non integrative lentiviral vectors" (or NILV) is meant efficient gene delivery vectors that do not integrate the genome of a target cell through the action of the virus integrase.

One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". A vector according to the present invention comprises, but is not limited to, a YAC (yeast artificial chromosome), a BAC (bacterial artificial), a baculovirus vector, a phage, a phagemid, a cosmid, a viral vector, a plasmid, a RNA vector or a linear or circular DNA or RNA molecule which may consist of chromosomal, non chromosomal, semi-synthetic or synthetic DNA. In general, expression vectors of utility in recombinant DNA techniques are often in the form of "plasmids" which refer generally to circular double stranded DNA loops which, in their vector form are not bound to the chromosome. Large numbers of suitable vectors are known to those of skill in the art. Vectors can comprise selectable markers, for example: neomycin phosphotransferase, histidinol dehydrogenase, dihydrofolate reductase, hygromycin phosphotransferase, herpes simplex virus thymidine kinase, adenosine deaminase, glutamine synthetase, and hypoxanthine-guanine phosphoribosyl transferase for eukaryotic cell culture; TRP1 for *S. cerevisiae*; tetracyclin, rifampicin or ampicillin resistance in *E. coli*. Preferably said vectors are expression vectors, wherein a sequence encoding a polypeptide of interest is placed under control of appropriate transcriptional and translational control elements to permit production or synthesis of said polypeptide. Therefore, said polynucleotide is comprised in an expression cassette. More particularly, the vector comprises a replication origin, a promoter operatively linked to said encoding polynucleotide, a ribosome binding site, a RNA-splicing site (when genomic DNA is used), a polyadenylation site and a transcription termination site. It also can comprise an enhancer or silencer elements. Selection of the promoter will depend upon the cell in which the polypeptide is expressed. Suitable promoters include tissue specific and/or inducible promoters. Examples of inducible promoters are: eukaryotic metallothionine promoter which is induced by increased levels of heavy metals, prokaryotic lacZ promoter which is induced in response to isopropyl-β-D-thiogalacto-pyranoside (IPTG) and eukaryotic heat shock promoter which is induced by increased temperature. Examples of tissue specific promoters are skeletal muscle creatine kinase, prostate-specific antigen (PSA), α-antitrypsin protease, human surfactant (SP) A and B proteins, β-casein and acidic whey protein genes.

Inducible promoters may be induced by pathogens or stress, more preferably by stress like cold, heat, UV light, or high ionic concentrations (reviewed in Potenza C et al. 2004, In vitro Cell Dev Biol 40:1-22). Inducible promoter may be induced by chemicals (reviewed in (Zuo and Chua 2000; Padidam, Gore et al. 2003; Wang, Zhou et al. 2003; Moore, Samalova et al. 2006).

Delivery vectors and vectors can be associated or combined with any cellular permeabilization techniques such as sonoporation or electroporation or derivatives of these techniques.

The term "endonuclease", or "nuclease" refers to any wild-type or variant enzyme capable of catalyzing the hydrolysis (cleavage) of bonds between nucleic acids within a DNA or RNA molecule, preferably a DNA molecule. Endonucleases can be classified as rare-cutting endonucleases when having typically a polynucleotide recognition greater than 12 base pairs (bp) in length, more preferably of 14-45 bp. Rare-cutting endonucleases significantly increase HR by inducing DNA double-strand breaks (DSBs) at a defined locus (Perrin, Buckle et al. 1993; Rouet, Smih et al. 1994; Rouet, Smih et al. 1994; Choulika, Perrin et al. 1995; Pingoud and Silva 2007). Rare-cutting endonucleases can for example be a homing endonuclease (Paques and Duchateau 2007), a chimeric Zinc-Finger nuclease (ZFN) (Eisenschmidt, Lanio et al. 2005; Arimondo, Thomas et al. 2006; Simon, Cannata et al. 2008), A TALE-nuclease or a chemical endonuclease. In chemical endonucleases, a chemical or peptidic cleaver is conjugated either to a polymer of nucleic acids or to another DNA recognizing a specific target sequence, thereby targeting the cleavage activity to a specific sequence. Chemical endonucleases also encompass synthetic nucleases like conjugates of orthophenanthroline, a DNA cleaving molecule, and triplex-forming oligonucleotides (TFOs), known to bind specific DNA sequences (Kalish and Glazer 2005). Such chemical endonucleases are comprised in the term "endonuclease" according to the present invention.

Transcription Activator Like Effector (TALE) is a family of proteins used in the infection process by plant pathogens of the *Xanthomonas* genus (Boch, Scholze et al. 2009; Moscou and Bogdanove 2009; Christian, Cermak et al. 2010; Li, Huang et al. 2011; Li, Huang et al. 2011). The term "TAL effector nuclease" (TALE-Nuclease) refers to a nuclease comprising a TAL-effector domain fused to a nuclease domain. These DNA binding domains may be engineered to bind to a desired target and fused to a nuclease domain, such as the FokI nuclease domain, to derive a TAL effector domain-nuclease fusion protein.

The term "Zinc-finger nuclease" (ZFN) refers to artificial restriction enzymes generated by fusing a zinc finger DNA-binding domain to a DNA-cleavage domain. Zinc finger domains can be engineered to bind to a desired target site. In some embodiments, the cleavage domain comprises the non-specific cleavage domain of FokI (Porteus and Carroll 2005). In other embodiments, the cleavage domain comprises all or an active portion of another nuclease.

By "catalytic domain" is intended the protein domain or module of an enzyme containing the active site of said enzyme; by active site is intended the part of said enzyme at which catalysis of the substrate occurs. Enzymes, but also their catalytic domains, are classified and named according to the reaction they catalyze. The Enzyme Commission number (EC number) is a numerical classification scheme for enzymes, based on the chemical reactions they catalyze.

The term "exonuclease" refers to enzymes that cleave phosphodiester bonds at the end of a polynucleotide chain via a hydrolyzing reaction that breaks phosphodiester bonds at either the 3' or 5' end. The polynucleotide may be double-stranded DNA (dsDNA), single-stranded DNA (ssDNA), RNA, double-stranded hybrids of DNA and RNA, and synthetic DNA (for example, containing bases other than A, C, G, and T). The term "5' exonuclease" refers to exonucleases that cleave the phosphodiester bond at the 5' end. The term "3' exonuclease" refers to exonucleases that cleave the phosphodiester bond at the 3' end. Exonucleases may cleave the phosphodiester bonds at the end of a polynucleotide chain at endonuclease cut sites or at ends generated by other chemical or mechanical means, such as shearing, ionizing radiation, ultraviolet radiation, oxygen radicals, chemical hydrolosis and chemotherapy agents. Exonucleases may cleave the phosphodiester bonds at blunt ends or sticky ends. *E. coli* exonuclease I and exonuclease III are two commonly used 3'-exonucleases that have 3'-exonucleolytic single-strand degradation activity. Other examples of 3'-exonucleases include Nucleoside diphosphate kinases (NDKs), NDK1 (NM23-H1), NDK5, NDK7, and NDK8, WRN, and Three prime repair exonuclease 2 (Trex2). *E. coli* exonuclease VII and T7-exonuclease Gene 6 are two commonly used 5'-3' exonucleases that have 5% exonucleolytic single-strand degradation activity. The exonuclease can be originated from prokaryotes, such as *E. coli* exonucleases, or eukaryotes, such as yeast, worm, murine, or human exonucleases.

by "functional mutant" is intended a catalytically active mutant of a protein or a protein domain; such mutant can have the same activity compared to its parent protein or protein domain or additional properties. This definition applies to chimeric proteins or protein domains that constitute chimeric proteins according to the present invention. Are also encompassed in the scope of this definition "derivatives" of these proteins or protein domains that comprise the entirety or part of these proteins or protein domains fused to other proteic or chemical parts such as tags, antibodies, polyethylene glycol as non-limiting examples.

By nucleic acid or protein "homologous sequence" it is meant a sequence with high percentage of identity or high percentage of homology with sequences at nucleotidic or polypeptidic levels. By high percentage of identity or high percentage of homology it is intended at least 70%, more preferably at least 75%, more preferably at least 80%, more preferably at least 85%, more preferably at least 90%, more preferably at least 95%, more preferably at least 97%, more preferably at least 99% or any percentage value between 70% and 99%.

"identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting.

The term "cleavage" refers to the breakage of the covalent backbone of a polynucleotide. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. Double stranded DNA, RNA, or DNA/RNA hybrid cleavage can result in the production of either blunt ends or staggered ends.

The terms "target site", "target sequence", "target nucleic acid sequence" or "nucleic acid target sequence" refer to a nucleic acid sequence that defines a portion of a nucleic acid to which a binding molecule will bind and/or cleave, provided sufficient conditions for binding and/or cleaving are present.

A "domain" of a protein is any portion of the entire protein, up to and including the complete protein, but typically comprising less than the complete protein. A domain can, but need not, fold independently of the rest of the protein chain and/or be correlated with a particular biological, biochemical, or structural function or location (e.g., an endonuclease domain, a polynucleotide binding domain, such as a DNA-binding domain, or an end-processing domain).

The term "subject" as used herein includes all members of the animal kingdom including non-human primates and humans.

BRIEF DESCRIPTION OF THE TABLES AND THE FIGURES

For a better understanding of the invention and to show how the same may be carried into effect, there will now be shown by way of example only, specific embodiments, methods and processes according to the present invention with reference to the accompanying drawings in which:

Table 1 shows the positions of the amino acid residues in the CCR5_S08-targeting LHE that were varied or otherwise became altered relative to the primary sequence of the wild-type I-OnuI protein during the re-specification process. The CCR5_S08_1B6 LHE contains variations only to the 47 residues which comprise the protein-DNA interface, not all of which retuned amino acids different from the wild-type I-Onul protein, but all of which were varied in the initial stages of re-specification. The top performing variant following refinement screening had additional 8 mutations, 4 of which are located within the protein-DNA interface, 4 of which are elsewhere in the protein.

FIG. 1: depicts the location of six putative target sequences, annotated as Onu_S##, in the protein-coding exon of the human CCR5 gene for which superior LHE-DNA recognition sequences are predicted. The locations of the seven transmembrane helices, annotated as TM1-7, of the CCR5 protein are indicated, along with each of the out-of-frame stop codons (TGA, TAA, TAG) that would putatively be placed in frame upon insertion and primarily deletion of upstream sequences resulting from the non-homologous end joining (NHEJ) repair of nuclease-generated double-stranded DNA breaks.

FIG. 2 shows schematically and structurally the location of the protein-DNA interface that defines the interaction between a LAGLIDADG homing endonuclease (LHE) and its DNA substrate. The schematic illustration generally depicts the concept that there is a continuous region of the LHE that comprises the interaction with DNA. The structural images demonstrate in more detail the nature of this interaction, whereby the protein-DNA interfacial residues of the LHE (whose side-chain atoms are shown as black spheres) interdigitate into the major grooves of DNA helix. It is the constellation of interfacial side chain atoms which determine the complementarity of a natural or engineered LHE to the atoms of the DNA nucleotides, which themselves form sequence specific patterns.

FIG. 3 shows that, of the six target sites that were chosen for protein-DNA interface engineering, only two (CCR5_S02 and CCR5_S08) yielded variant LHEs capable of cleaving the full target sequence. Two such variants are shown in the panels which depict flow cytometric analysis of DNA hydrolysis, whereby the baker's yeast, *Saccharomyces cerevisiae*, express the LHE on the surface of their cells and are interrogated with fluorescent dye-labelled synthetic DNA substrates as has been published. Briefly, samples are first stained with a biotinylated antibody to an epitope appended to the N- or C-terminus of the LHE. During this staining procedure, conjugates of phycoerythrin-labeled streptavidin (x-axis) with biotin- and Alexa fluor-647 (y-axis) labeled synthetic DNA substrates are generated at a relative molarity that preserves some biotin binding sites on the streptavidin. These pre-conjugates are then used to counter stain the yeast cells, resulting in the co-linear streptavidin-PE/Alexa fluor-647 profile. Cleavage-inhibiting (Ca2+) and cleavage-permitting (Mg2+) conditions are then used to determine whether the native or engineered LHE cleaves the tethered target, which, if cleaved, loses signal in the y-axis owing to loss of the Alexa fluor-647 fluorophore.

FIG. 4 shows an assay whereby DNA binding titration is used to establish the affinity properties of the CCR5_S02 and CCR5_S08 targeting LHEs. Samples of yeast displaying each LHE variant were independently incubated with increasing concentrations of fluorescent dye-labeled synthetic DNA substrates (y-axis). An antibody to a C-terminal epitope was also included (x-axis) such that DNA binding activity could be normalized to the amount of LHE protein expressed on the yeast surface, creating the co-linear pattern, with higher signal in the y-axis per x-axis signal where affinity is greater. The results demonstrate that the I-Onul LHE (OnuWT) has an approximate Kd of approximately 80 pM, the CCR5_S02_1F5 has a Kd of approximately 35 pM, and the CCR5_S08_1B6 variant has the highest affinity at approximately 20 pM.

FIG. 5 shows the specificity profiling of the CCR5_S02_1F5 (top panels) and the CCR5_S08_1B6 (bottom panels) LHE variants. Cleavage analysis was performed as described in FIG. 3, however panels of DNA substrates were tested whereby each of the 22 positions along the target was serially altered to each of the 3 non-native base pairs and tested in cleavage-inhibiting and cleavage-permitting conditions. The resulting cleavage profiles for the 67 different substrates (the target in the CCR5 gene and the 66 'one-off' substrates) indicate which LHE variants have most ideal specificity properties and are therefore better candidates for applications demanding tighter specificity, such as in human therapeutics.

FIG. 6 shows the flow cytometry scatter properties of primary human T cells which are highly susceptible to double-stranded DNA breaks resulting in genotoxicity and cell death. T cells transfected with an in vitro transcribed mRNA (IVT-mRNA) species encoding an innocuous protein such as the blue fluorescent protein (BFP), show 62% survival during in vitro culture, a level similar to unmanipulated T cells. In contrast, T cells transfected with mRNA encoding the CCR5_S02_1F5 protein experience a profound toxicity, presumably due to the occurrence of numerous double-stranded DNA breaks that result from the poor specificity properties of the CCR5_S02_1F5 LHE. Conversely, the CCR5_S08_1B6 variant results in only very minor losses of T cell viability, confirming that its global DNA specificity is of high quality.

FIG. 7 shows the initial targeting efficiency of the CCR5_S08_1B6 variant and the progressive improvements in the targeting efficiency achieved by the activity refinement process. Targeting efficiency was measured using a chromosomally integrated double-strand break fluorescent reporter termed the 'traffic light reporter' (TLR). Human embryonic kidney 293T (HEK 293T) fibroblasts were constructed to contain the CCR5_S08 DNA sequence immediately upstream of an out-of-frame mCherry fluorescent protein (y-axis) which, upon one of three possible frame outcomes of the NHEJ DNA repair process becomes fluorescent. The percentage of cells in the y-axis therefore represents approximately ⅓ of all imprecise nuclease-mediated repair events. This cell line was then transfected with expression plasmids which encode the CCR5_S08 targeting LHEs along with a blue fluorescent protein (x-axis) to track transfected cells. The original CCR5_S08_1B6 variant inefficiently caused double-stranded breaks and therefore produced only small percentages of mCherry positive cells ($2^{nd}$ panel from left). Three rounds of activity refinement screening led to vast improvements in the generation of mCherry positive cells.

FIG. 8 shows a comparative alignment of the CCR5_S08_1B6 variant (SEQ ID NO:12) its derivative, CCR5_S08_RD3-21 (aa 1-303 of SEQ ID NO:19), that was identified on the third round of activity refinement. The strand-loop-strand motifs which comprise the DNA binding domain are depicted above the aligned sequences.

FIG. 9 shows a schematic depiction of the location of the CCR5_S08 target site within the CCR5 protein. The target site is located late in the protein at the boundary of the sixth transmembrane helix and the final extracellular loop. Also shown is the CCR5_S08 target sequence (in bold) within the DNA (SEQ ID NO:22) and primary amino acid (SEQ ID NO:23) sequences of the CCR5 gene, and the location of the 11-mer TALE array is indicated both schematically (repetitive units are not annotated but shown upstream of the CCR5_S08 annotation) and its sequence is shown in bold.

FIG. 10 shows schematics of representative self-inactivating (SIN) lentiviral production plasmids from which lentivirus preparations were generated and used as vectors containing CCR5_S08 LHE for the transduction of cell lines and primary cells (A) (SEQ ID NO:24) as well as an exemplary non-limiting vectorcontaining the megaTAL construct used either in lentiviral production or for in vitro transcription for the production of IVT-mRNA (B)(SEQ ID NO:29). The primary features of the vector, in addition to the lentiviral features well known to those familiar with the art such as the long terminal repeats (LTRs), primer binding site (PBS), and central polypurine tract (cPPT), are multicistronic elements for the expression of a CCR5-targeting LHE (A) or megaTAL (B) linked via a T2A peptide dislinker motif to the Trex2 exonuclease which further carries an internal ribosomal entry site (IRES) and blue fluorescent protein (BFP) for tracking transduced cells.

FIG. 11A shows the complete loss of expression of the CCR5 protein from GHOST-Hi5 cells transduced with lentivirus encoding the CCR5_S08 targeting LHE and Trex2 exonuclease. The flow cytometry panels represent independent GHOST-Hi5 cell samples transduced with lentiviruses encoding either the wild-type I-OnuI LHE or the CCR5_S08 targeting LHE, gated on cells expressing BFP and therefore containing integrated copies of the LHE-Trex2-IRES-BFP cassette driven by the SFFV promoter. An antibody recognizing the extracellularly located epitopes of the CCR5 protein was used to stain the cells to differentiate between CCR5 expressing cells and CCR5 deficient cells whose CCR5 gene(s) have undergone nuclease mediated disruption. FIG. 11B. The sequence alignment (nucleotides 4103-4217 of SEQ ID NO:20) shows the frequency of CCR5 gene disruption from cells isolated from the sample transduced with the CCR5_S08 targeting LHE which was FACS sorted on the basis of CCR5 antibody staining.

FIG. 12 shows a schematic representation of the ultra-efficient CCR5 gene disruption technology based on the combination of the megaTAL architecture and Trex2 expression. Also shown are representative flow cytometry plots of GHOST-Hi5 cells electroporated with synthetically generated in vitro transcribed mRNA (IVT-mRNA) encoding either the CCR5_S08 targeting megaTAL alone or when the megaTAL is co-expressed with Trex2. On both axes are independent fluorescent signals from two antibodies recognizing non-overlapping epitopes of the CCR5 protein, providing extra assurance that the protein is indeed being removed from the cell surface by IVT-mRNA mediated transient delivery of the reagents.

FIG. 13 shows an in vitro HIV-1 infection experiment whereby live virus was added to the GHOST-Hi5 cells after they had been treated with the IVT-mRNAs encoding the CCR5_S08 targeting megaTAL and Trex2 as described in FIG. 12. Since GHOST-Hi5 cells contain an integrated cassette comprising an HIV-1 responsive promoter driving the expression of the GFP gene, infected cells can be visualized by flow cytometry. As shown in the bottom row of panels, a significant percentage of HIV-1 infected control (not treated with any IVT-mRNA) GHOST-Hi5 cells become infected and express GFP. From the IVT-mRNA treated cells, those which remained CCR5 positive also remained infectible to an equivalent degree as the untreated controls. However, those cells which had lost CCR5 expression were infected by the HIV-1 virus at a substantially lower rate, confirming that the disruption of the CCR5 gene also disturbs the HIV-1 cell entry machinery.

FIG. 14 depicts schematically one treatment strategy that could be used to generate populations of CCR5-deficient HIV-1 resistant T cells in an HIV-1 infected patient. Briefly, peripheral blood mononuclear cells (PBMCs) would be isolated by apheresis, processed to purify and culture T cells, treated with CCR5-targeting nuclease delivery agents, and reinfused into the patient.

FIG. 15 confirms that disruptive mutations can be generated at the natural CCR5 locus in primary human T cells with extreme efficiencies using synthetic IVT-mRNA encoding the CCR5_S08 targeting megaTAL and Trex2 exonuclease reagents. The sequence alignment (nucleotides 4103-4177 of SEQ ID NO:20) was generated from individual sequencing reads from amplicons generated from genomic DNA isolated from human T cells treated according to the first steps described in FIG. 14.

EXAMPLES

Example 1

Figure 1:
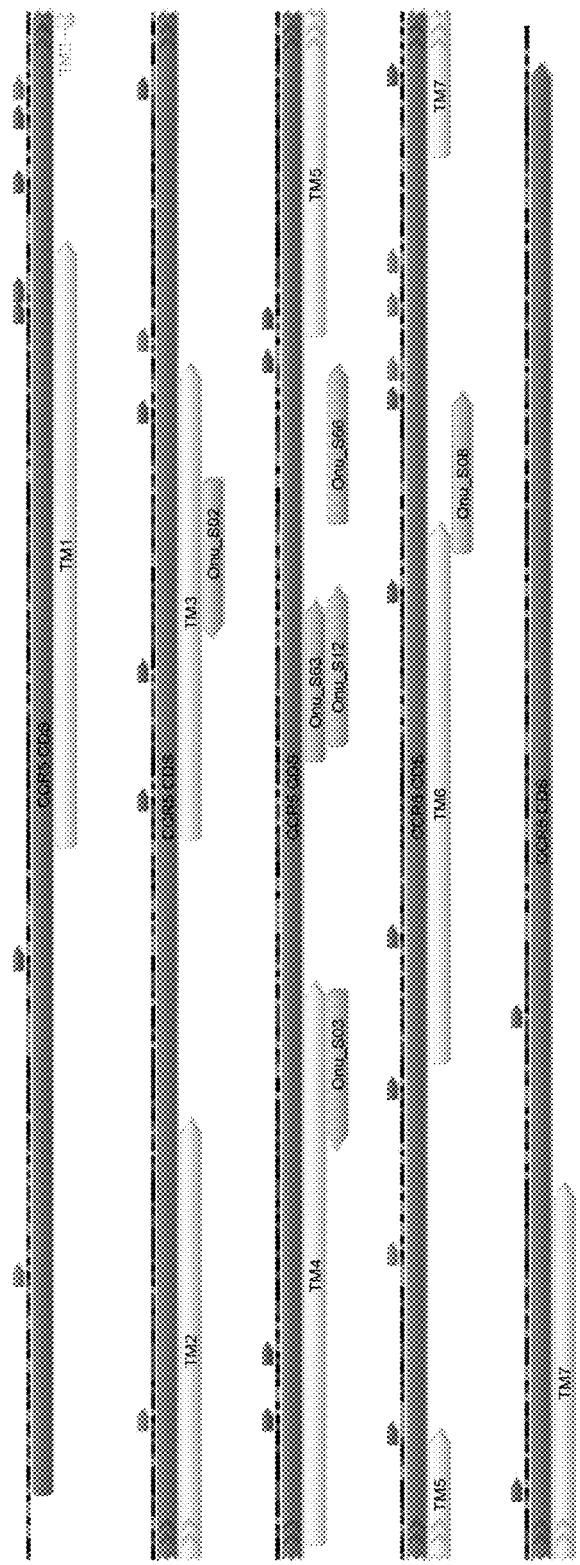

Engineering of LHE Prototypes with DNA Recognition Interfaces Specific for Targets in the Human CCR5 Gene was Performed We first identified putative LHE target sequences in the human CCR5 gene for which high quality engineered DNA recognition interfaces were predicted by the inventor. Such predictions are based on a series of features intrinsic to the LHE scaffold, I-OnuI (SEQ ID NO:2), upon which the CCR5 DNA recognition interfaces were to be engineered. Other considerations, such as locations within the CCR5 gene likely to cause significant disruptions to the CCR5 protein upon endonuclease-mediated insertions or deletions, and/or the occurrence of adjacent downstream TGA, TAG, or TAA stop codons in alternative reading frames to limit the production of out-of-frame peptides which could serve as the basis for immunological rejection, were also incorporated into the target choice process. See FIG. 1 which schematically illustrates the locations of the putative target sequences.

Figure 2:
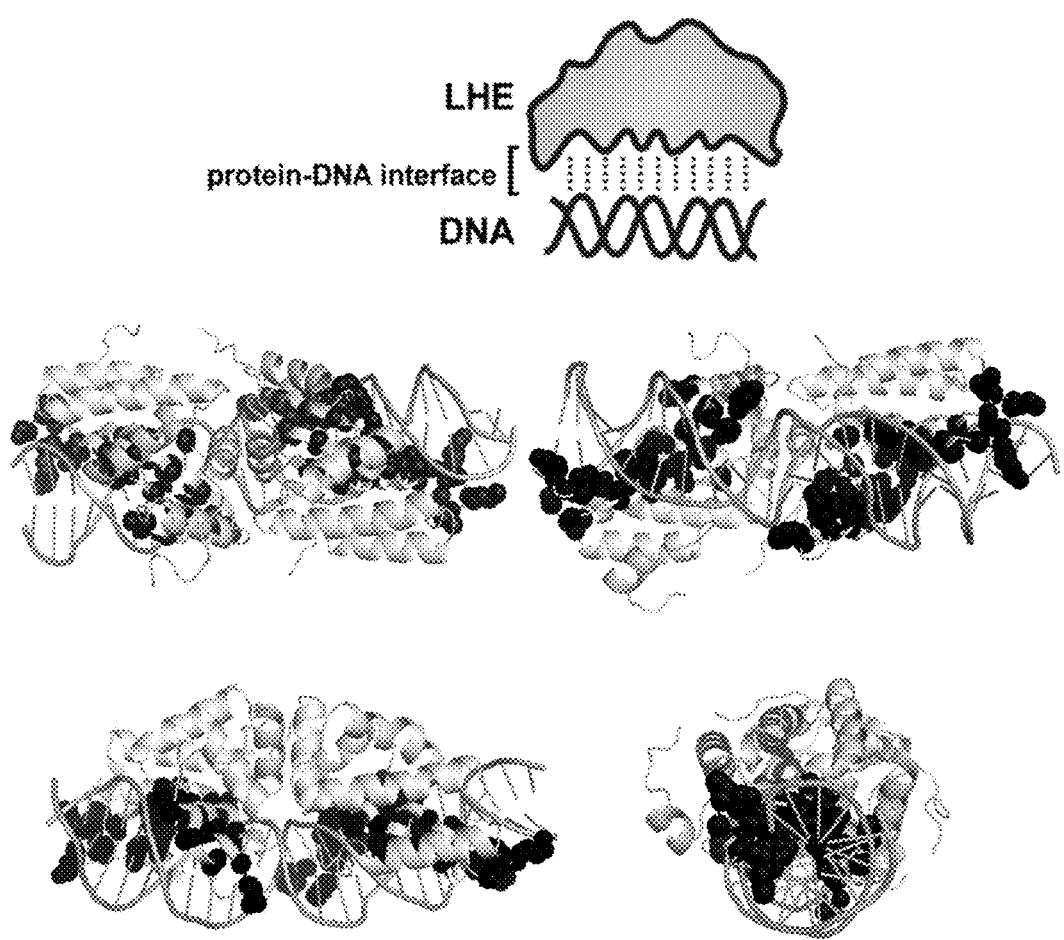
Figure 3:
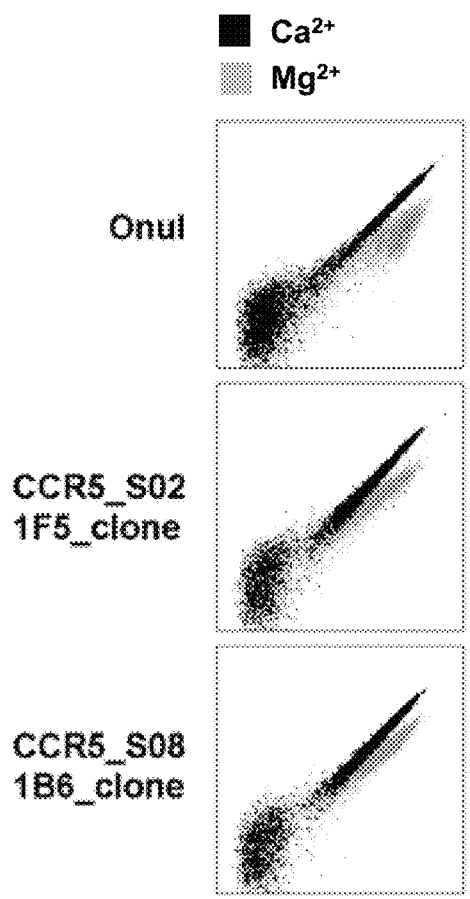

Six putative target sequences (CCR5_S02, CCR5_S03, CCR5_S08, CCR5_S12, CCR5_S63, and CCR5_S66; SEQ ID NOs:3 to SEQ ID NO:8, respectively) were chosen for the initial stages of engineering the DNA recognition interface. Variant libraries were constructed whereby amino acid residues in localized sub-regions of the DNA recognition interface were varied. See FIG. 2 which shows schematic and structural diagrams of the DNA recognition interface. Variation within the DNA recognition interface of I-OnuI nucleic acid sequence (SEQ ID NO:1) was achieved by incorporating degenerate codons into oligonucleotides which served as substrates for PCR reactions to generate variant libraries by gap recombination in the yeast strain *Saccharomyces cerevisiae*. The resulting libraries were screened for target cleavage activity by surface display and flow cytometry based methods as has been described in (Jarjour, West-Foyle et al. 2009). In this manner, the specificity of the DNA recognition interface was altered to recognize targets in the human CCR5 gene. In particular aspects, successfully re-specified DNA recognition interfaces were achieved for CCR5_S02 (SEQ ID NO:3) and CCR5_S08 (SEQ ID NO:5) only, with the process failing for the other four putative target sites at various stages in the engineering process. See FIG. 3 illustrating the successful isolation of variants cleaving the CCR5_S02 and CCR5_S08 targets.

Example 2

Figure 4:
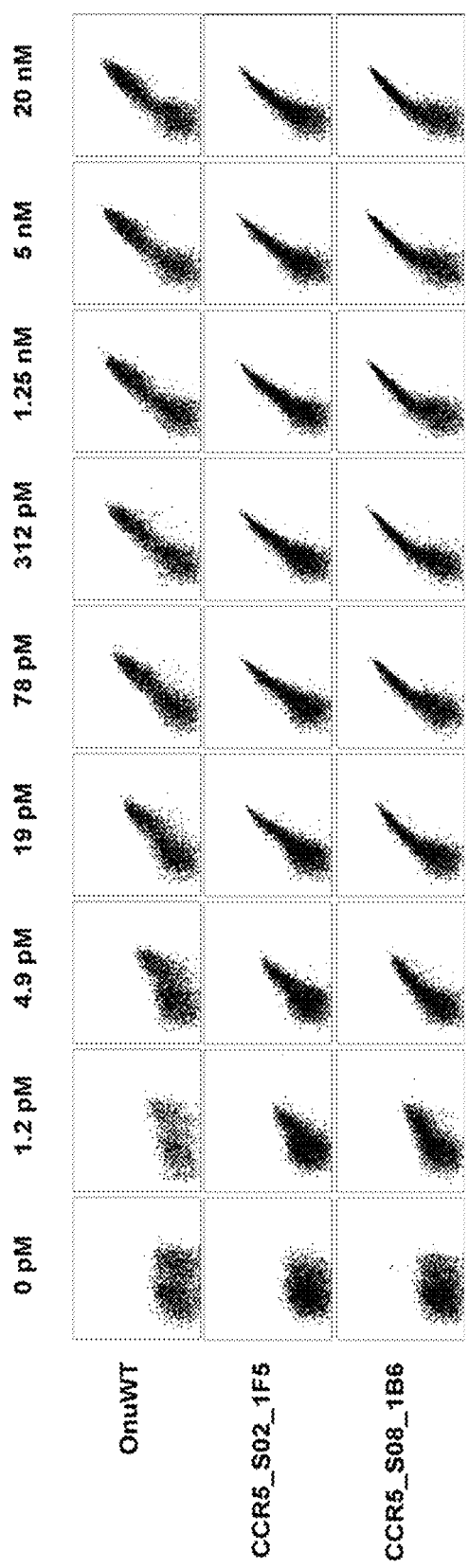
Figure 5:
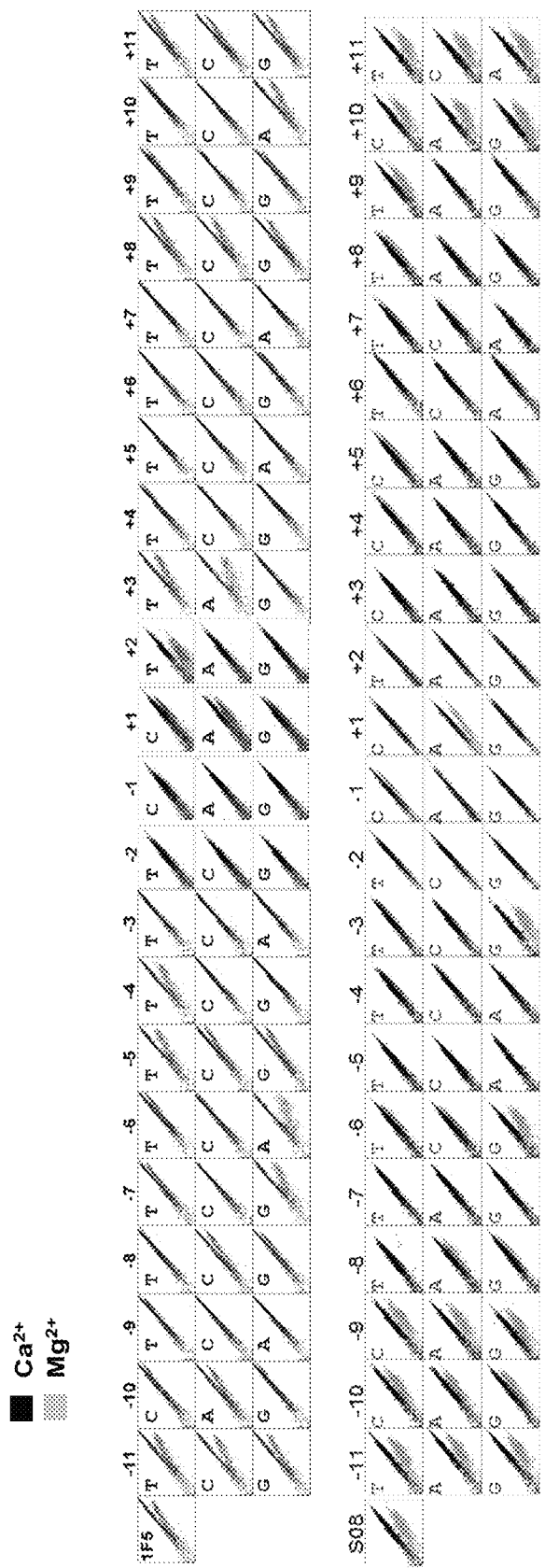
Figure 6:
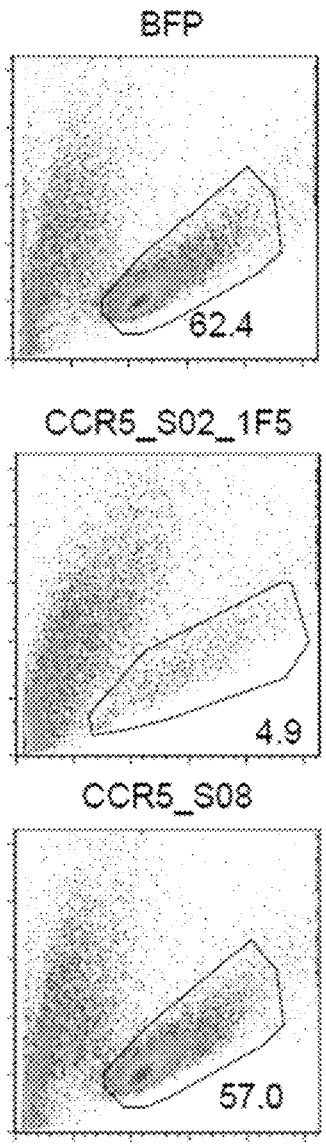

LHEs with DNA Recognition Interfaces having High Affinity, High Specificity, and Low Toxicity were Differentiated The LHEs containing the engineered DNA recognition interfaces for the CCR5_S02 (SEQ ID NO:3) and CCR5_S08 (SEQ ID NO:5) targets were tested for affinity, specificity, and toxicity characteristics. Affinity was tested by independently incubating yeast displaying the CCR5_S02_1F5 variant, (SEQ ID NO: 09 encoding SEQ ID NO: 10), and the CCR5_S08_1B6 variant (SEQ ID NO: 11 encoding SEQ ID NO:12), with DNA substrates containing their target sequences at various concentrations. See FIG. 4 showing the affinity properties of these two variants relative to the wild-type I-OnuI protein. These data demonstrate that both the CCR5_S02_1F5 variant and the CCR5_S08_1B6 variant bind their DNA targets with affinities comparable or higher than that of the interaction between the native I-OnuI LHE and its target sequence (SEQ ID NO:13). Specificity was tested by analyzing the relative ability of each LHE to cleave target sequences containing each of the three alternate DNA base pairs at each position along the substrate. See FIG. 5 illustrating the specificity profile of the CCR5_S02_1F5 and CCR5_S08_1B6 variants. These data demonstrate that the CCR5_S08_1B6 LHE has a greater overall specificity, as in more positions along its target it exclusively cleaves the substrate containing the proper base pair, not tolerating substitutions. Toxicity was analyzed by in vitro transcribing each LHE into mRNA and transfecting primary human T cells by electroporation, followed by flow cytometry analysis of the survival of the cells relative to transfection with a control mRNA encoding a blue fluorescent protein (BFP). See FIG. 6 showing flow cytometry analysis of primary human T cells after treatment with the CCR5_S02_1F5 and CCR5_S08_1B6 variants. These data show that the CCR5_S08_1B6 LHE has minimal toxicity, while the CCR5_S02_1F5 LHE has substantial toxicity indicating that its lower specificity properties correspond to more abundant and harmful double-strand break accumulation when expressed in human cells.

Example 3

LHEs with Engineered DNA Recognition Interfaces were Shown to Cause Disruptive Mutations to the Target Sequences for which they were Engineered to Recognize To measure the activity of the CCR5 targeting LHEs, we used a chromosomally integrated fluorescent reporter system that has been described previously. In this system, the LHE of interest is transfected into a HEK 293T fibroblast cell line that is engineered to contain the CCR5_S08 target sequence upstream of an out-of-frame gene encoding the fluorescent protein mCherry. Cleavage of the embedded CCR5_S08 target and subsequent small insertions or deletions caused by DNA repair via the non-homologous end joining (NHEJ) pathway result in approximately 1 out of three repaired loci placing the fluorescent reporter gene 'in-frame'. Fluorescence in the mCherry channel on a flow cytometer is therefore a surrogate high-throughput readout of LHE cleavage of the chromosomally embedded CCR5_S08 target sequence.

Figure 7:
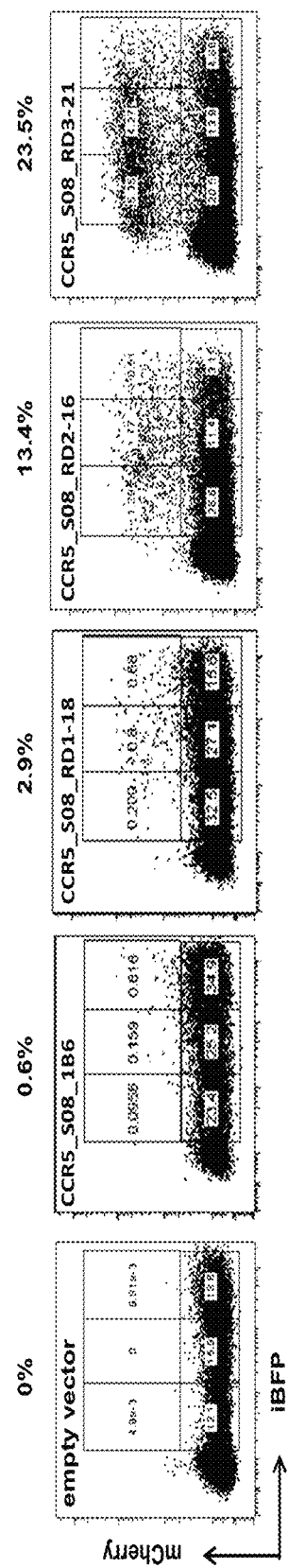
Figure 8:
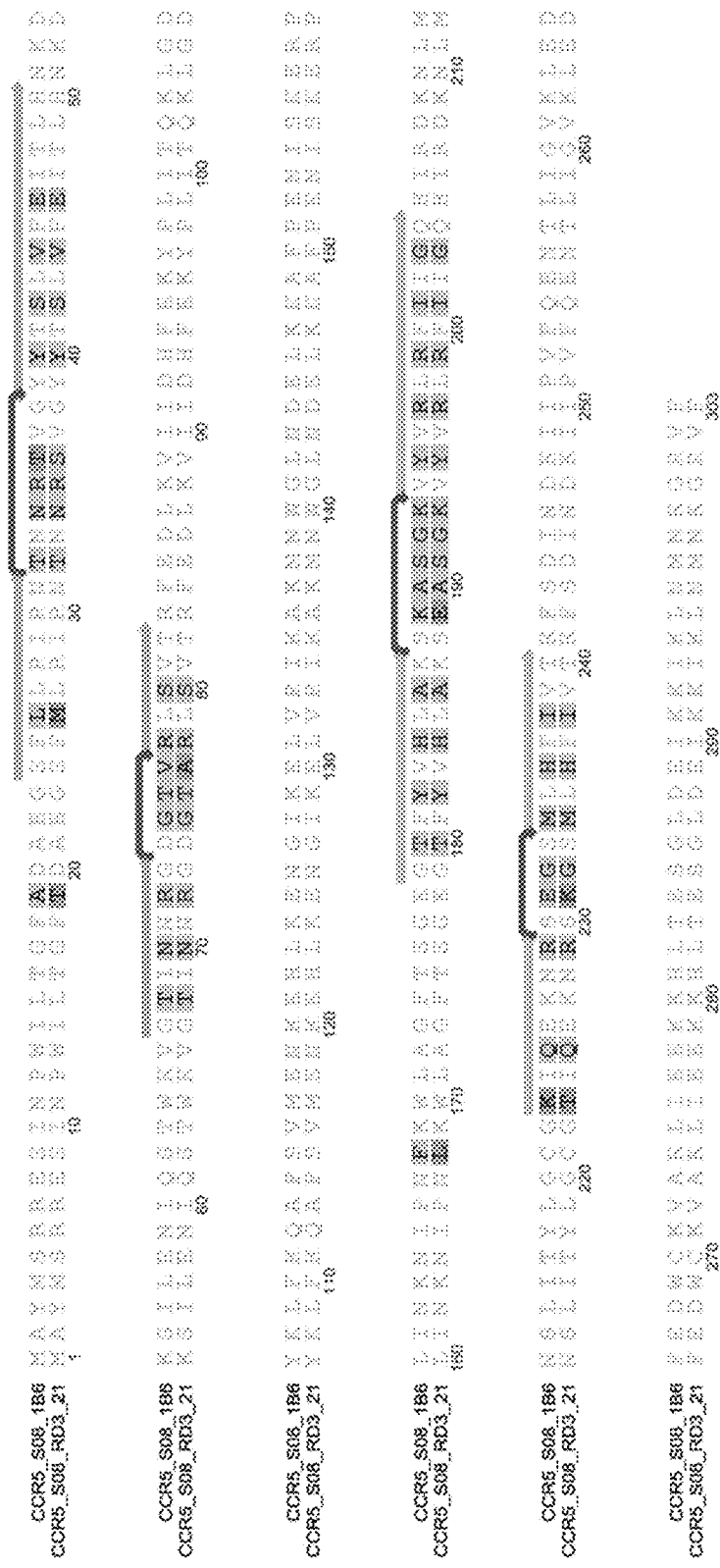

Initial results with the CCR5_S08_1B6 variant showed very low efficiency of mCherry expression, indicating that this variant was not very actively cleaving its target in a cellular chromosomal context. We therefore performed random mutagenesis of the CCR5_S08_1B6 variant and surface display-based screening under more stringent cleavage conditions to isolate variants with improved catalytic activities. Three rounds of mutagenesis and screening led to variants with 40- to 50-fold higher rates of generating mCherry expressing cells. See FIG. 7 illustrating the flow cytometry read-outs from the reporter assay for CCR5_S08_1B6_RD1-18 (SEQ ID NO:14 encoding SEQ ID NO:15), CCR5_S08_1B6_RD2-16 (SEQ ID NO:16 encoding SEQ ID NO:17) and CCR5_S08_1B6_RD3-21 (SEQ ID NO:18 encoding SEQ ID NO:19) variants isolated during the refinement screening process. The top performing variant, CCR5_S08_1B6_RD3-21, (SEQ ID NO:19), contained eight amino acids mutations relative to the CCR5_S08_1B6 variant, four of which are located within the DNA recognition interface and four located elsewhere in the LHE. See FIG. 8 and Table 1 which provide the relative alignments of the indicated variants as well as the positional information of the residues comprising the DNA recognition interface. It is unknown to what extent, if any, the individual mutations identified through this process contribute to the characteristics of the LHE which influence its DNA recognition and cleavage activity. Taken together they led to significant improvements in the frequency of the occurrence disruptive mutations to the CCR5_S08 target sequence.

Example 4

Figure 9:
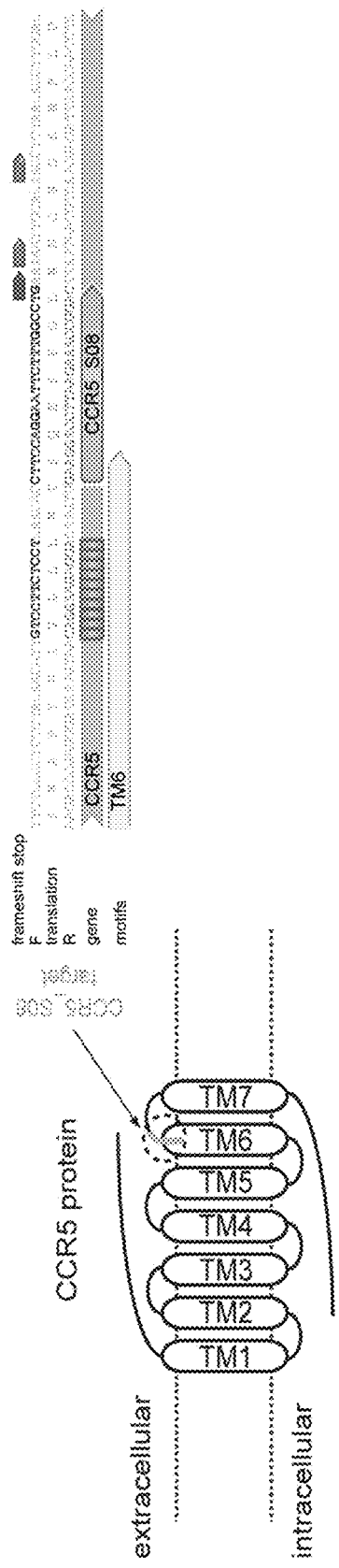

CCR5-targeting LHEs were Shown to Cause Disruptive Mutations at the CCR5 Gene and the Loss of the CCR5 Protein from the Cell Surface We next examined whether the CCR5-targeting LHE: i) efficiently cleaved the CCR5_S08 target site in the CCR5 gene (SEQ ID NO:20) in human cells; and ii) whether the resulting NHEJ-mediated disruptions resulted in the loss of the CCR5 protein from the cell surface. Despite the optimal properties of the engineered LHE and the CCR5_S08 target site, including the ideal specificity and affinity characteristics of the LHE and the presence of adjacent downstream off-frame stop codons as described above, the CCR5_S08 target site is situated in CCR5 gene region encoding the boundary of the $6^{th}$ transmembrane domain and terminal extracellular loop of the CCR5 protein (SEQ ID NO:21). See FIG. 9 which schematically illustrates the location of the CCR5_S08 target site and provides detailed information on the nucleotidic and peptidic sequences (SEQ ID NO:22 and SEQ ID NO:23) comprising and adjacent to the CCR5_S08 target site. It was therefore feasible that disruptions at this location in the gene could result in the continued production of a truncated CCR5 protein that was still able to be expressed on the cell surface and, if so, it could maintain its function as an HIV-1 co-receptor.

Figure 10:
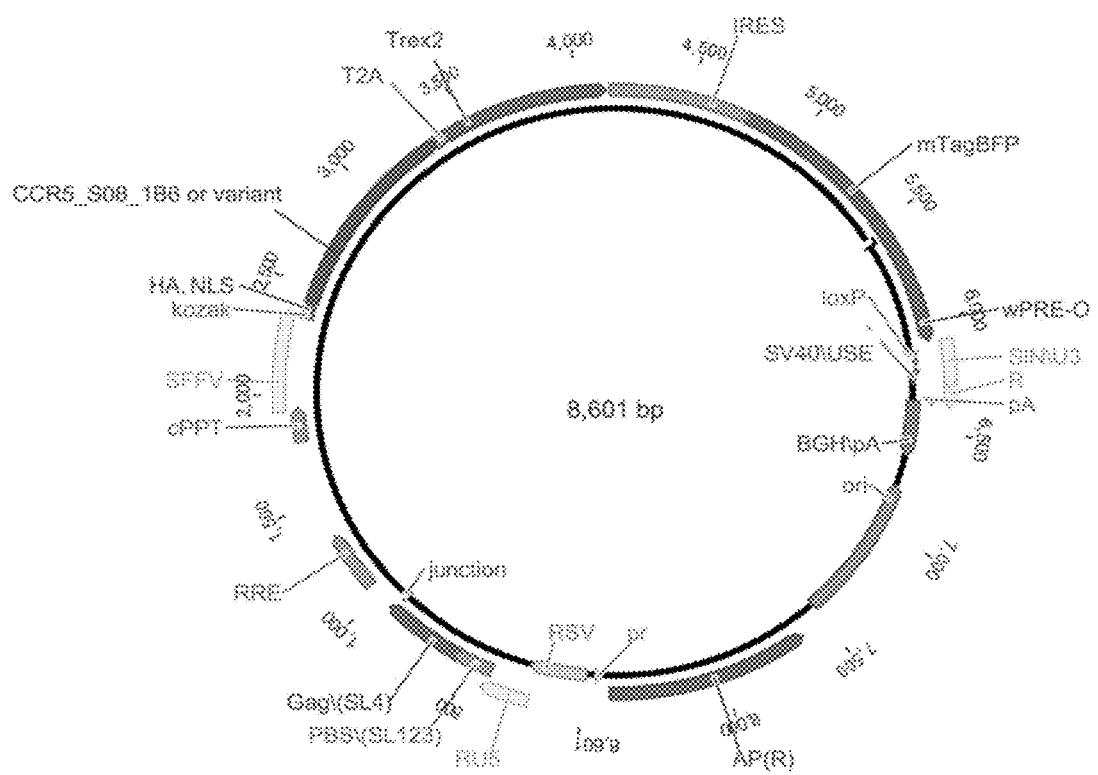

The GHOST-Hi5 cell line, comprising $CD4^+$ human osteosarcoma cells containing multiple retrovirally-integrated copies of the CCR5 gene, was therefore used for to analyze CCR5 gene disruption and its effect on CCR5 surface expression. GHOST-Hi5 cells were transduced with lentivirus preparations encoding either the wild type I-OnuI LHE as a control or the CCR5_S08_1B6 LHE, or variants as described above. An example of a lentiviral production plasmid (SEQ ID NO:24) is shown in FIG. 10. Lentiviral integration of the SFFV promoter-driven LHE-T2A-Trex2-IRES-BFP cassette enables long-term co-expression of the CCR5 targeting LHE as well as the Trex2 exonuclease previously shown to enhance the rate of mutagenesis caused by LHEs and other site-specific nucleases. The IRES-BFP element enables the detection and isolation of GHOST-Hi5 cells which did sustain the permanent integration of the vector.

Figure 11A:
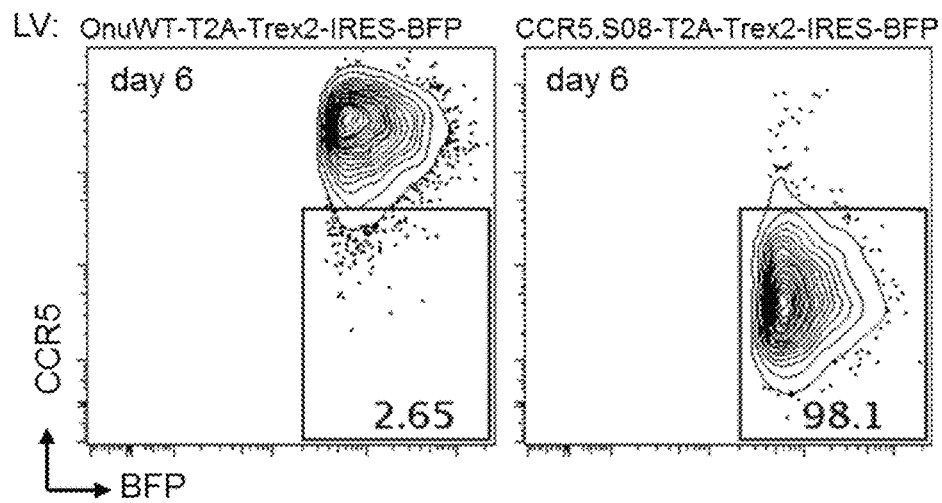
Figure 11B:
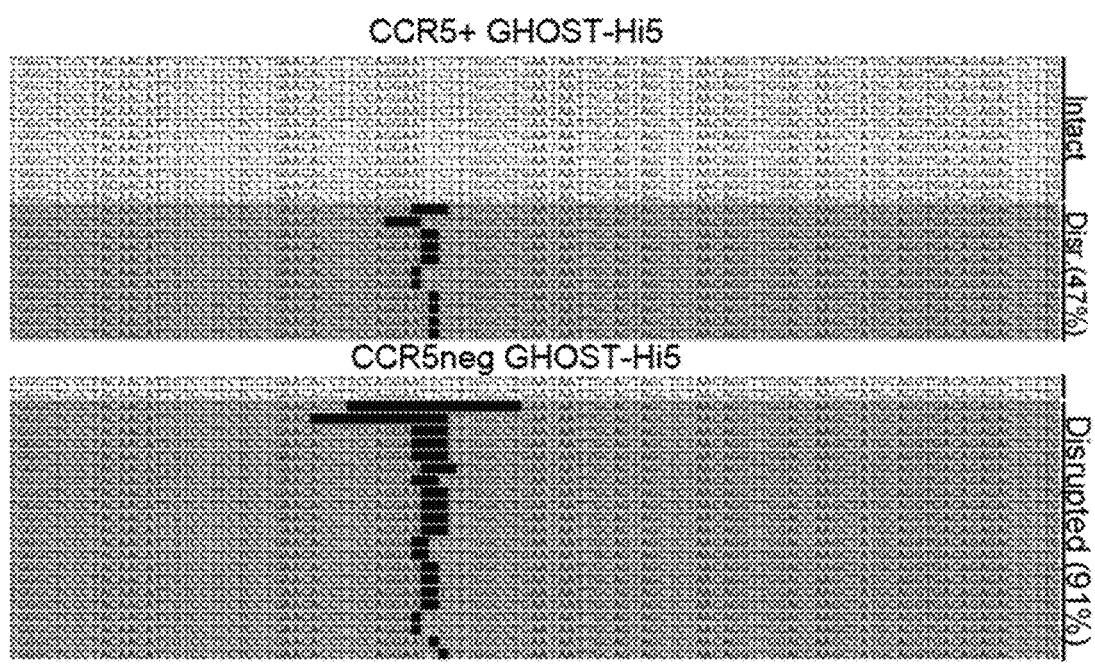

Six days after transduction of GHOST cells with the lentivirus encoding the CCR5-targeting LHE and Trex2, greater than 98% of the transduced cells had lost cell surface expression of the CCR5 protein. Cell surface expression of CCR5 was measured by a sensitive flow cytometry assay using multiple antibodies raised to various extracellular epitopes of the CCR5 protein. See FIG. 11 demonstrating the flow cytometry panels (FIG. 11A) and DNA sequencing confirmation of the disruption of the CCR5 gene (FIG. 11B). Genomic DNA was then isolated from FACS sorted populations comprising the CCR5-positive and CCR5-negative samples, and the region of the CCR5 gene encompassing the CCR5_S08 target sequence was sub-cloned and sequenced to confirm and characterize the spectrum of LHE-induced mutations (FIG. 11B). A critical conclusion from this experiment is that disruptions that reset the continuation of the CCR5 protein to each of the three reading frames are observed in the CCR5-negative sample, and that 3 bp 'in-frame' deletions are not enriched in the CCR5-positive samples (mutations are observed in this sample owing to the multiple CCR5 gene copies and the need to disrupt most or all of them to produce the CCR5-negative phenotype). This indicates that all disruptions, including in-frame deletions, disturb the overall biogenesis of the CCR5 protein and result in its failure to reach the cell surface. This finding confirms that extreme rates of CCR5 disruption with the CCR5_S08 targeting LHE are feasible and have the potential to reach saturation efficiencies of CCR5 removal from the cell surface.

Example 5

CCR5-targeting LHEs were Improved by Fusion with Transcription Activator-like Effector (TALE) Domains, Enabling Efficient CCR5 Gene Disruption with Transient Synthetic Delivery Methods While persistent LHE expression results in efficient CCR5 gene disruption as demonstrated in EXAMPLE 4, there are numerous advantages to achieving similarly high rates of disruptive CCR5 gene mutations from shorter exposures to the nuclease reagents. One primary motivation for achieving high efficiencies is in developing human therapeutic interventions based on CCR5 disrupting nucleases. In such an application, using viral vectors which permanently (such as for retroviral, lentiviral, or foamy viral vectors) or transiently (such as adenoviral or adeno-associated viral vectors) deliver nuclease reagents is laborious, cost and resource-intensive, poorly scalable, and challenging to address from a regulatory perspective. A more attractive therapeutic reagent and process would involve replacing the biological vector with a synthetic expression reagent, such as in vitro transcribed mRNA (IVT-mRNA). However, our initial studies with CCR5_S08 targeting LHE and Trex2 delivery in the IVT-mRNA form showed detectable but low overall rates of CCR5 gene disruption.

Figure 12:
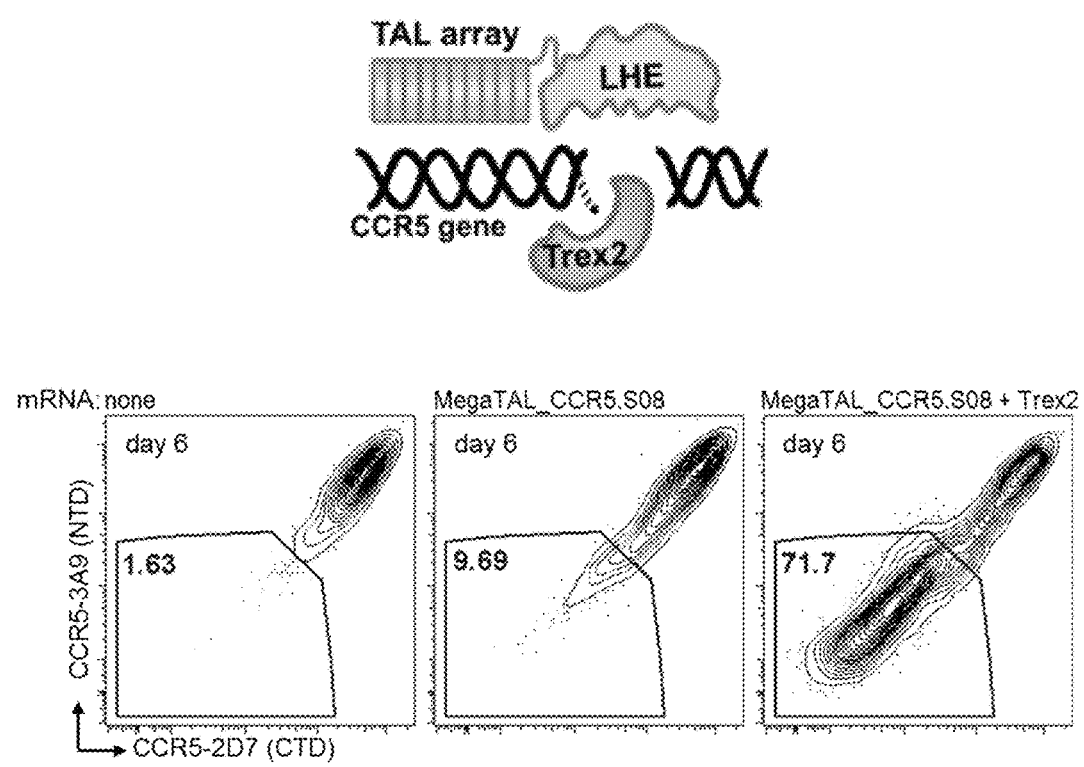

We therefore sought to create a chimeric endonuclease architecture that could improve the efficiency of the CCR5 targeting LHE such that high disruption rates could be achieved with a synthetic delivery agent such as IVT-mRNA. As described herein, TALE proteins offer a uniquely modular mode of DNA recognition. We therefore reasoned that an array of TALE repeats which recognized a target sequence adjacent to the CCR5_S08 target could be fused to the CCR5_S08 targeting LHE to effectively enhance the co-localization of the nuclease and its substrate. See FIG. 12 which schematically illustrates the chimeric endonuclease. This chimeric endonuclease (SEQ ID NO:25)—an architecture termed 'megaTAL'—was then converted into mRNA (SEQ ID NO:26) using MegaTAL CCR5_S08 LHE lentiviral vector as template (SEQ ID NO:27) by in vitro transcription methods well known to those familiar with the art. MegaTAL CCR5_S08 Trex2 IVT-mRNA species (SEQ encoding the CCR5_S08 targeting megaTAL and the Trex2 exonuclease (SEQ ID NO: 28) were synthesized using MegaTAL CCR5_S08 Trex2 lentiviral vector as template (SEQ ID NO:29 and FIG. 10B) and were then delivered by electroporation to GHOST-Hi5 cells. This method of transiently expressing these nuclease reagents resulted in extremely efficient removal of the CCR5 protein from the cell surface. See FIG. 12 which shows the flow cytometry analysis of GHOST-Hi5 cells treated with IVT-mRNA species encoding the megaTAL and Trex2 exonuclease.

Example 6

Cells Treated with CCR5-targeting LHEs are Demonstrated to be Resistant to HIV-1 Infection Next we confirmed that the disruptions to the CCR5 gene and to the cell surface expression of the CCR5 protein caused by the CCR5-targeting LHEs also reduced the ability of the HIV-1 virus to enter the cells. The GHOST-Hi5 cell line expresses both human cell surface proteins, CD4 and CCR5, recognized by the HIV-1 cell entry machinery comprising the viral envelope proteins gp120 and gp41. In addition, GHOST-Hi5 cells contain an integrated GFP reporter gene that is driven by the HIV-1 long terminal repeat (LTR) promoter. Upon HIV-1 infection and expression of virally-encoded trans-activators of the LTR promoter, GHOST-Hi5 cells produce the GFP protein. Owing to this reporter, infection efficiency can be quantified by simply flow cytometry.

Figure 13:
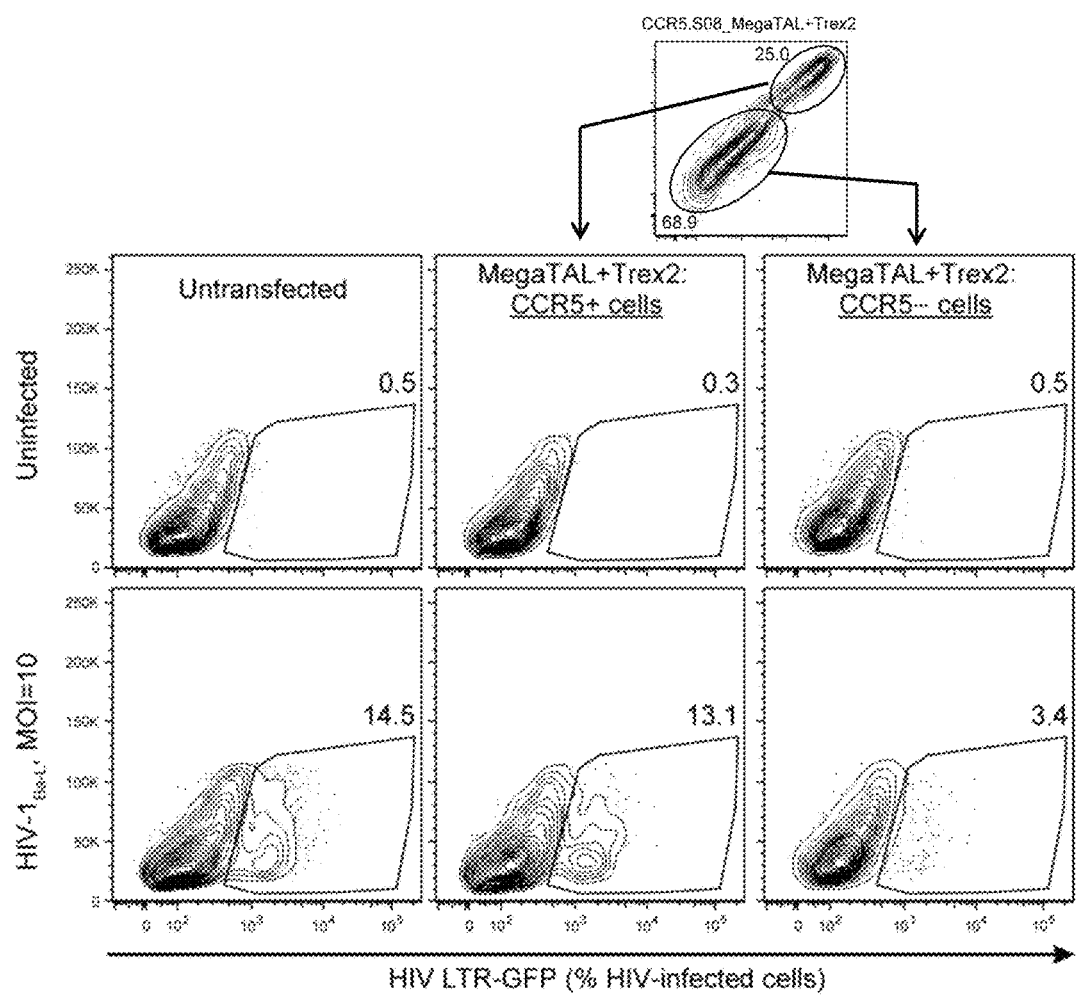

We first treated GHOST-Hi5 cells with the CCR5-targeting megaTAL and Trex2 exonuclease reagents as described in EXAMPLE 5 such that CCR5-expressing and CCR5-deficient cells were present in the cell population. We next exposed these cells to live virus preparations of the HIV-$1_{BAL}$ strain commonly used in laboratory and animal studies of HIV-1 infection. The efficiency of infection of the CCR5-expressing and CCR5-deficient cells was then monitored by flow cytometry, whereby the percentage of GFP expressing cells was determined on populations segregated on the basis of their CCR5 staining properties. This experiment demonstrates that GHOST-Hi5 cells made deficient in cell surface expression of the CCR5 protein through transient delivery of CCR5_S08 targeting megaTAL and Trex2 exonuclease reagents are substantially protected from HIV-1 infection. See FIG. 13 which shows the flow cytometry read-out of HIV-1 infection and how it is abolished in the CCR5 deficient population that arises from the treatment of GHOST-Hi5 cells with IVT-mRNA species described herein.

Example 7

Figure 14:
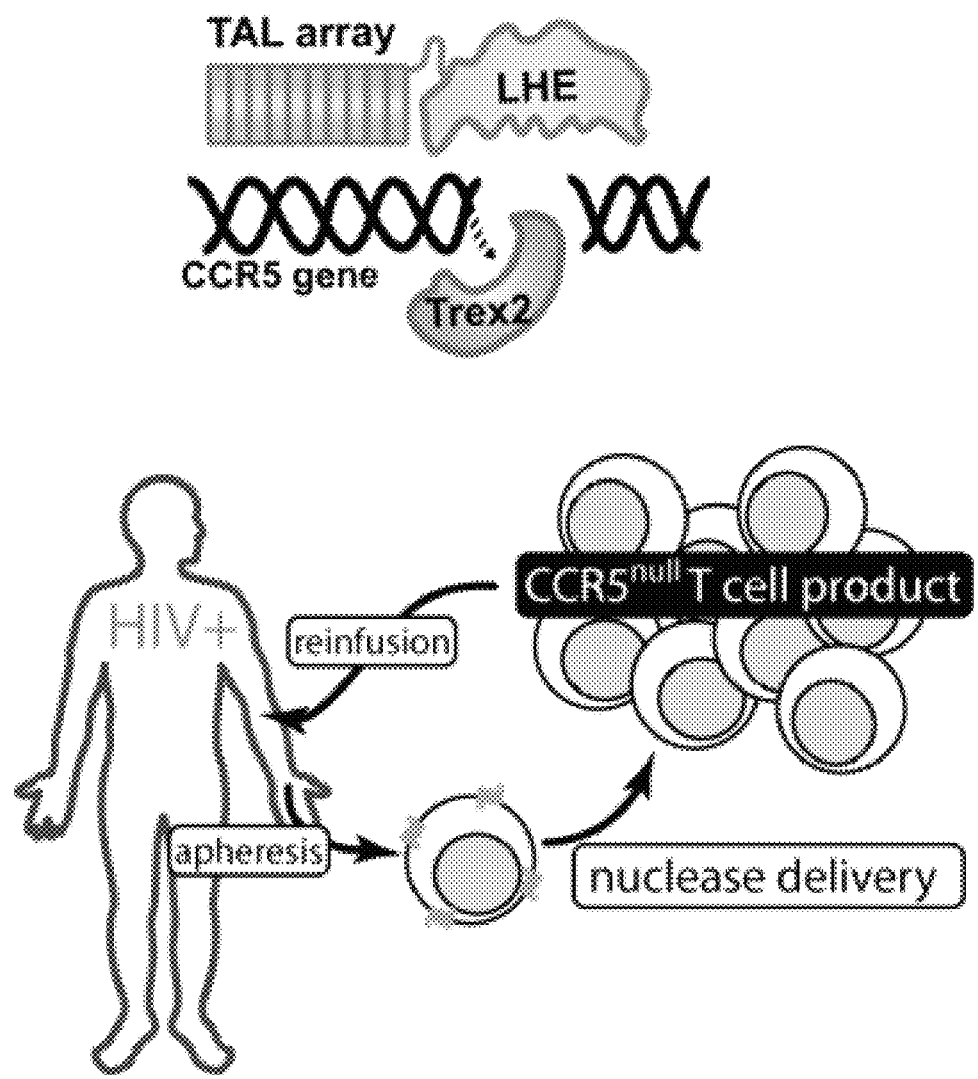

CCR5-targeting LHEs Delivered to Human Primary T Cells were Shown to Cause Disruptive Mutations in the CCR5 Gene The results of the examples provided above demonstrate that the nuclease reagents described herein are able to affect an HIV-1 protective phenotype through the permanent genetic ablation of the CCR5 gene. This conclusively validates the mechanism of action of these reagents and the efficiency of a transient delivery method and formulation. Finally, we sought to extend these findings into primary human T cells, which are the foremost human cell population that is targeted by the HIV-1 virus. Indeed, the most proximal therapeutic strategy for implementing CCR5 targeting nucleases involves isolating T cells from the blood of HIV-1 infected patients, treating the T cells with nuclease reagents, and re-infusing the CCR5-deficient cells back into the patient. See FIG. 14 which schematically shows the proposed therapeutic strategy.

Figure 15:
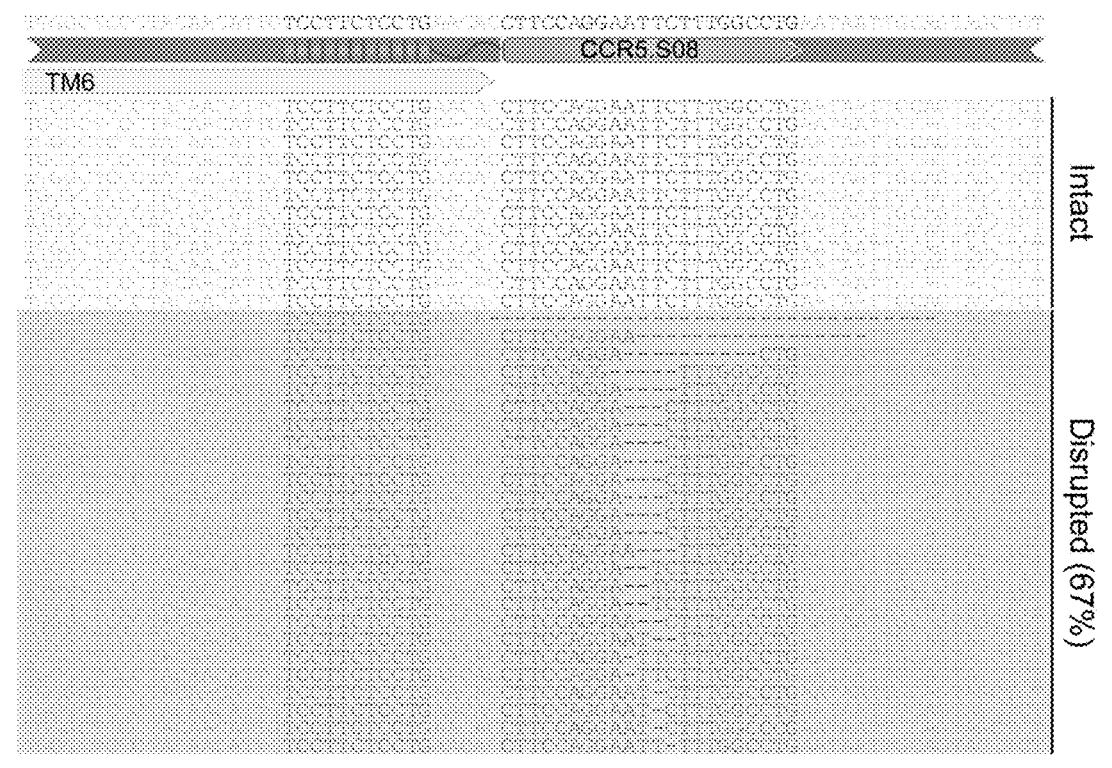

To model the first stages of this putative therapeutic process, primary human T cells were isolated from peripheral blood mononuclear cells (PBMCs) and stimulated and expanded for in vitro culture using established methods well known to those in the art. Similar to the experiment described in EXAMPLE 6, IVT-mRNA species encoding the CCR5_S08 targeting megaTAL with our without the Trex2 exonuclease were electroporated into the human T cells. Several days after electroporation, genomic DNA preparations of the variously treated samples were isolated and the region of the CCR5 gene encompassing the CCR5_S08 target sequence was sub-cloned and sequenced. FIG. 15 shows the results from this analysis which confirm that extremely high rates of disruptive mutations were achieved in the CCR5 gene, as >65% of the sequenced amplicons from cells treated with the megaTAL and Trex2 reagents were modified.

Example 8

Figure 16:
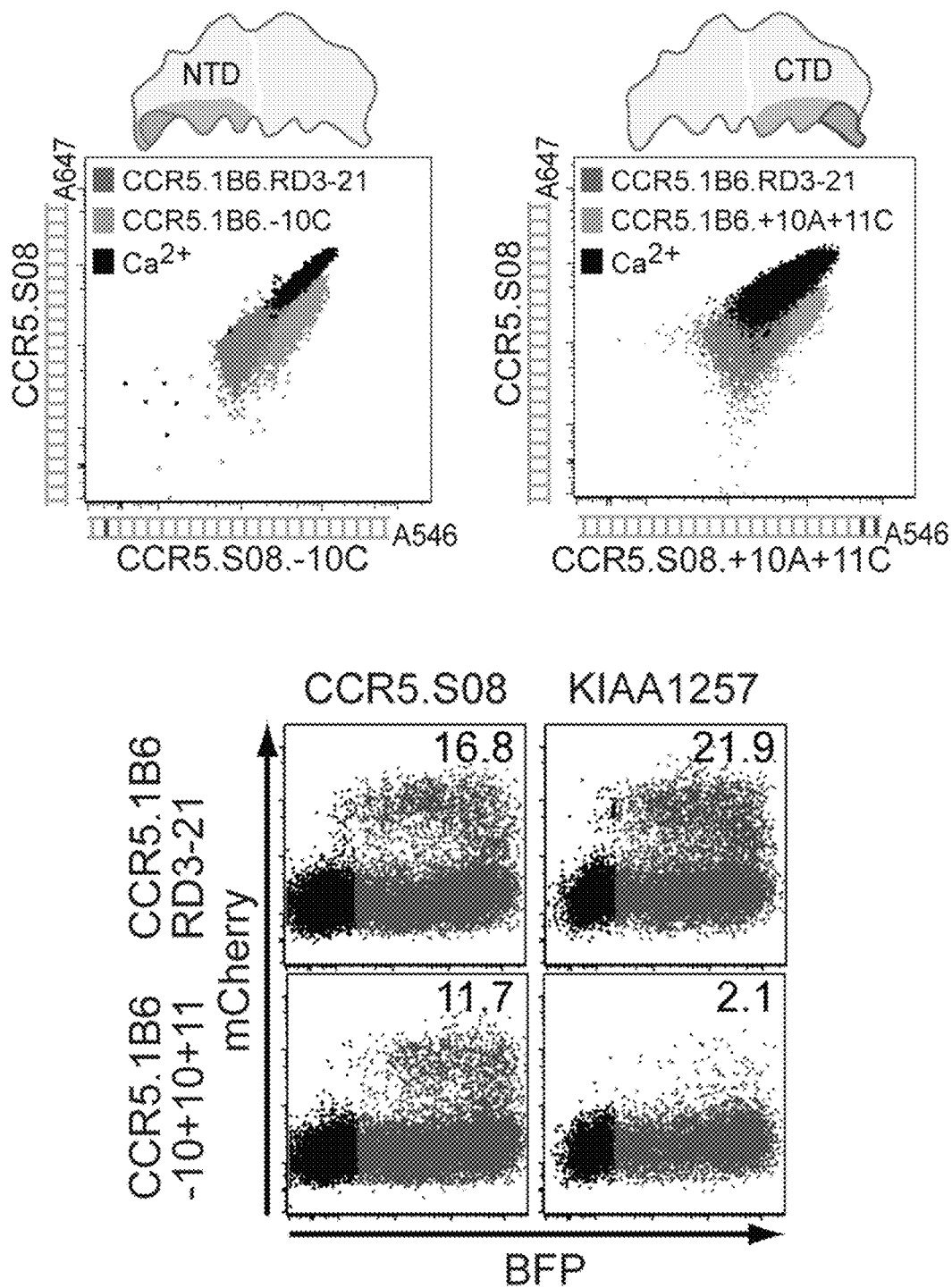
FIG. 16 illustrates specificity refinement of the CCR5.S08 targeting LHE using multiparameter flow screening. The resulting variants showed improved specificity when tested in vivo using a fluorescent reporter of gene disruption.

CCR5-targeting LHEs were Further Refined by Improving the Selectivity for their Target Site in the CCR5 Gene To demonstrate that the selectivity of reprogrammed HEs could be further refined to improve the safety of gene editing applications, the display-based DNA hydrolysis assay was adapted to screen for HE variants that discriminate between DNA substrates conjugated to spectrally unique fluorophores. After confirming that the CCR5_S08 targeting LHE was active against an off-target site in an uncharacterized gene, KIAA1257, two refinement libraries were constructed wherein we randomized the amino acids proximal to the base pairs that were different (−10, +10, +11) in the CCR5_S08 and KIAA1257, termed the '−10 NTD' and '+10+11 CTD' libraries. From each refinement library, subvariants were isolated, which were more selective for cleaving the CCR5_S08 target relative to the targets bearing the KIAA1257 substitutions. NTD and CTD specificity refined sub-variants was then refined and confirmed (using the reporter assay described in FIG. 7) The resulting LHE CCR5_S08 ('CCR5 −10+10+11, SEQ ID NO: 30) had several-fold reduced in vivo activity against the KIAA1257 site (FIG. 16).

Example 9

Figure 17:
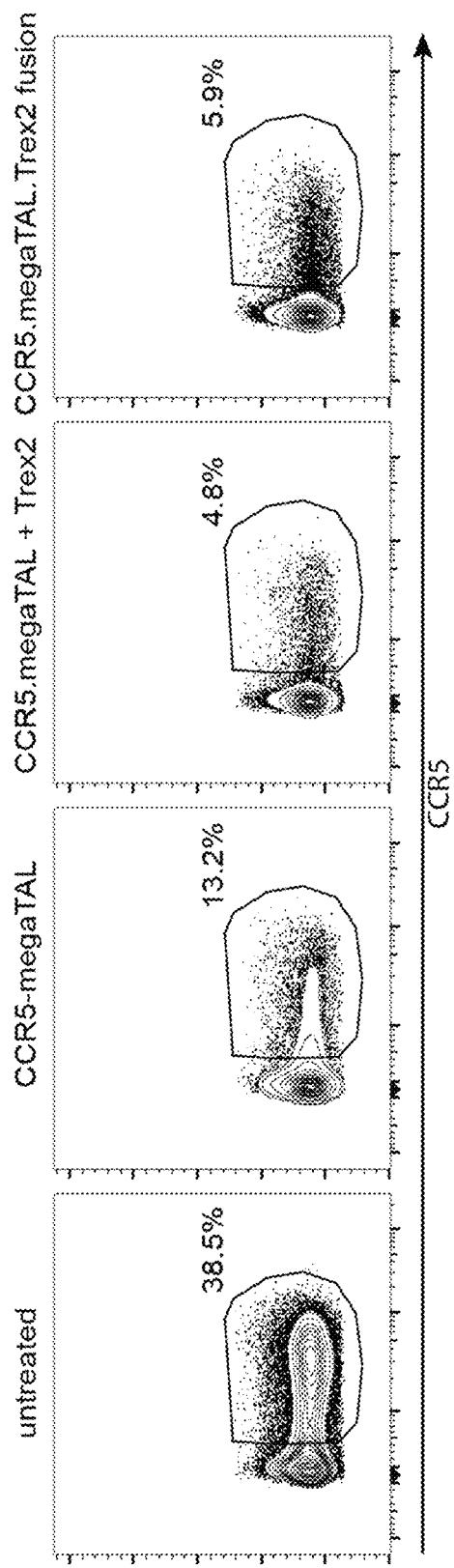
FIG. 17 shows efficient CCR5 gene inactivation in primary human T cells via electroporation with an mRNA species encoding a three component TAL-LHE-Trex2 fusion protein.

CCR5-targeting, TALE-LHE Fusions were Improved by Fusion with Trex2, Enabling Ultra-efficient CCR5 Gene Disruption with a Three-component Fusion Protein Expressed from a Single mRNA Species Next it was evaluated whether efficient CCR5 gene disruption could be achieved by delivering a single mRNA species expressing a fusion protein comprising a TAL array, the CCR5_S08 targeting LHE, and Trex2. This three-component fusion protein (SEQ ID NO:32) was placed in a vector containing a T7 promoter to facilitate in vitro transcription and subsequent polyadenylation and capping. The resulting mRNA was delivered to primary human T cells by electroporation and CCR5 protein expression was assessed 72 hours later by flow cytometry (FIG. 17). Control samples included untransfected primary human T cells, T cells transfected with the CCR5_S08 targeting MegaTAL, and a sample where the CCR5_S08 targeting MegaTAL was cotransfected with an independently synthesized Trex2 encoding mRNA species. The samples receiving Trex2 either independently or as a direct fusion with the CCR5_S08 targeting MegaTAL showed a smaller remaining population of CCR5-positive cells, indicating enhanced CCR5 gene disruption rates in these samples.

REFERENCES

Arimondo, P. B., C. J. Thomas, et al. (2006). "Exploring the cellular activity of camptothecin-triple-helix-forming oligonucleotide conjugates." Mol Cell Biol 26(1): 324-33.

Baxter, S., A. R. Lambert, et al. (2012). "Engineering domain fusion chimeras from I-Onul family LAGLIDADG homing endonucleases." Nucleic Acids Res.

Bitinaite, J., D. A. Wah, et al. (1998). "FokI dimerization is required for DNA cleavage." Proc Natl Acad Sci USA 95(18): 10570-5.

Boch, J., H. Scholze, et al. (2009). "Breaking the code of DNA binding specificity of TAL-type III effectors." Science 326(5959): 1509-12.

Choulika, A., A. Perrin, et al. (1995). "Induction of homologous recombination in mammalian chromosomes by using the I-Scel system of Saccharomyces cerevisiae." Mol Cell Biol 15(4): 1968-73.

Christian, M., T. Cermak, et al. (2010). "Targeting DNA double-strand breaks with TAL effector nucleases." Genetics 186(2): 757-61.

Cong, L., F. A. Ran, et al. (2013). "Multiplex genome engineering using CRISPR/Cas systems." Science 339 (6121): 819-23.

Critchlow, S. E. and S. P. Jackson (1998). "DNA end-joining: from yeast to man." Trends Biochem Sci 23(10): 394-8.

Eisenschmidt, K., T. Lanio, et al. (2005). "Developing a programmed restriction endonuclease for highly specific DNA cleavage." Nucleic Acids Res 33(22): 7039-47.

Jarjour, J., H. West-Foyle, et al. (2009). "High-resolution profiling of homing endonuclease binding and catalytic specificity using yeast surface display." Nucleic Acids Res 37(20): 6871-80.

Jinek, M., K. Chylinski, et al. (2012). "A programmable dual-RNA-guided DNA endonuclease in adaptive bacterial immunity." *Science* 337(6096): 816-21.

Kalish, J. M. and P. M. Glazer (2005). "Targeted genome modification via triple helix formation." *Ann N Y Acad Sci* 1058: 151-61.

Kim, Y. G., J. Cha, et al. (1996). "Hybrid restriction enzymes: zinc finger fusions to Fok I cleavage domain." *Proc Natl Acad Sci USA* 93(3): 1156-60.

Li, T., S. Huang, et al. (2011). "TAL nucleases (TALNs): hybrid proteins composed of TAL effectors and FokI DNA-cleavage domain." *Nucleic Acids Res* 39(1): 359-72.

Li, T., S. Huang, et al. (2011). "Modularly assembled designer TAL effector nucleases for targeted gene knock-out and gene replacement in eukaryotes." *Nucleic Acids Res* 39(14): 6315-25.

Ma, J. L., E. M. Kim, et al. (2003). "Yeast Mre11 and Rad1 proteins define a Ku-independent mechanism to repair double-strand breaks lacking overlapping end sequences." *Mol Cell Biol* 23(23): 8820-8.

Mali, P., L. Yang, et al. (2013). "RNA-guided human genome engineering via Cas9." *Science* 339(6121): 823-6.

Moore, I., M. Samalova, et al. (2006). "Transactivated and chemically inducible gene expression in plants." *Plant J* 45(4): 651-83.

Moscou, M. J. and A. J. Bogdanove (2009). "A simple cipher governs DNA recognition by TAL effectors." *Science* 326(5959): 1501.

Pabo, C. O., E. Peisach, et al. (2001). "Design and selection of novel Cys2His2 zinc finger proteins." *Annu Rev Biochem* 70: 313-40.

Padidam, M., M. Gore, et al. (2003). "Chemical-inducible, ecdysone receptor-based gene expression system for plants." *Transgenic Res* 12(1): 101-9.

Paques, F. and P. Duchateau (2007). "Meganucleases and DNA double-strand break-induced recombination: perspectives for gene therapy." *Curr Gene Ther* 7(1): 49-66.

Perrin, A., M. Buckle, et al. (1993). "Asymmetrical recognition and activity of the I-SceI endonuclease on its site and on intron-exon junctions." *Embo J* 12(7): 2939-47.

Pingoud, A. and G. H. Silva (2007). "Precision genome surgery." *Nat Biotechnol* 25(7): 743-4.

Porteus, M. H. and D. Carroll (2005). "Gene targeting using zinc finger nucleases." *Nat Biotechnol* 23(8): 967-73.

Rouet, P., F. Smih, et al. (1994). "Expression of a site-specific endonuclease stimulates homologous recombination in mammalian cells." *Proc Natl Acad Sci USA* 91(13): 6064-8.

Rouet, P., F. Smih, et al. (1994). "Introduction of double-strand breaks into the genome of mouse cells by expression of a rare-cutting endonuclease." *Mol Cell Biol* 14(12): 8096-106.

Sethuraman, J., A. Majer, et al. (2009). "Genes within genes: multiple LAGLIDADG homing endonucleases target the ribosomal protein S3 gene encoded within an rnl group I intron of *Ophiostoma* and related taxa." *Mol Biol Evol* 26(10): 2299-315.

Simon, P., F. Cannata, et al. (2008). "Sequence-specific DNA cleavage mediated by bipyridine polyamide conjugates." *Nucleic Acids Res* 36(11): 3531-8.

Smith, J., J. M. Berg, et al. (1999). "A detailed study of the substrate specificity of a chimeric restriction enzyme." *Nucleic Acids Res* 27(2): 674-81.

Smith, J., M. Bibikova, et al. (2000). "Requirements for double-strand cleavage by chimeric restriction enzymes with zinc finger DNA-recognition domains." *Nucleic Acids Res* 28(17): 3361-9.

Takeuchi, R., A. R. Lambert, et al. (2011). "Tapping natural reservoirs of homing endonucleases for targeted gene modification." *Proc Natl Acad Sci USA* 108(32): 13077-82.

Thierry, A. and B. Dujon (1992). "Nested chromosomal fragmentation in yeast using the meganuclease I-Sce I: a new method for physical mapping of eukaryotic genomes." *Nucleic Acids Res* 20(21): 5625-31.

Wang, R., X. Zhou, et al. (2003). "Chemically regulated expression systems and their applications in transgenic plants." *Transgenic Res* 12(5): 529-40.

Zuo, J. and N. H. Chua (2000). "Chemical-inducible systems for regulated expression of plant genes." *Curr Opin Biotechnol* 11(2): 146-51.

The invention claimed is:

1. A chimeric endonuclease comprising:
an endonuclease domain having at least 90% identity with the amino acid sequence of SEQ ID NO:19 that cleaves a target nucleic acid sequence within the C-C chemokine receptor type 5 gene (CCR5), wherein the target nucleic acid sequence is SEQ ID NO:5; and
at least an additional protein domain selected from the group consisting of: nucleic acid binding domain, catalytic domain, terminal epitope tags and fluorescent proteins.

2. A chimeric endonuclease comprising:
an endonuclease domain having at least 70% identity with the amino acid sequence of SEQ ID NO:19 and having at least 95% identity with the DNA recognition interface of SEQ ID NO:19 that cleaves a target nucleic acid sequence within the C-C chemokine receptor type 5 gene (CCR5),
wherein the target nucleic acid sequence is SEQ ID NO:5 and,
wherein the endonuclease domain comprises at least 10 amino acid substitutions at positions selected from the group consisting of: amino acid position 19, 24, 26, 28, 30, 32, 34, 35, 36, 37, 38, 40, 42, 44, 46, 48, 68, 70, 72, 75, 76 77, 78, 80, 82, 168, 180, 182, 184, 186, 188, 189, 190, 191, 192, 193, 195, 197, 199, 201, 203, 223, 225, 227, 229, 231, 232, 234, 236, 238, and 240 in reference to SEQ ID NO:2,
and at least an additional protein domain selected from the group consisting of: nucleic acid binding domain, catalytic domain, terminal epitope tags and fluorescent proteins.

3. The chimeric endonuclease of claim 2, comprising an endonuclease domain having at least 90% sequence identity with the amino acid sequence of SEQ ID NO:19.

4. The chimeric endonuclease of claim 1, wherein the chimeric endonuclease comprises an amino acid sequence selected from the group consisting of: SEQ ID NO:12, SEQ ID NO:15, SEQ ID NO17, SEQ ID NO:19 and SEQ ID NO:31.

5. The chimeric endonuclease of claim 2, wherein the chimeric endonuclease comprises an amino acid sequence at least 95% identical to an amino acid sequence selected from the group consisting of: SEQ ID NO:12, SEQ ID NO:15, SEQ ID NO:17, SEQ ID NO:19 and SEQ ID NO.31.

6. The chimeric endonuclease of claim 1, wherein the additional protein domain is a nucleic acid binding domain selected from the group consisting of TALE and Zinc Finger domain.

7. The chimeric endonuclease of claim 6, wherein the chimeric endonuclease is the MegaTAL CCR5_S08 protein sequence selected from the group consisting of SEQ ID NO:25 and SEQ ID NO:33.

8. The chimeric endonuclease of claim 1, wherein additional protein domain has catalytic activity selected from the group consisting of: nuclease activity, polymerase activity, kinase activity, phosphatase activity, methylase activity, topoisomerase activity, integrase activity, transposase activity, ligase activity, helicase activity, recombinase activity.

9. The chimeric endonuclease of claim 1, wherein the catalytic domain is a 5'-3' exonuclease, more preferably Trex2 and more preferably single chain Trex2.

10. The chimeric endonuclease of claim 1, wherein the additional protein domain is fused to the endonuclease domain by a peptide linker.

11. The chimeric endonuclease of claim 1, fused to a nucleic acid binding domain and a catalytic domain.

12. The chimeric endonuclease of claim 11, wherein the additional protein domain is a nucleic acid binding domain selected from the group consisting of TALE and Zinc Finger domain.

13. The chimeric endonuclease of claim 11, wherein the catalytic domain is a 5'-3' exonuclease, more preferably Trex2 and more preferably single chain Trex2.

14. The chimeric endonuclease of claim 11, wherein the chimeric endonuclease comprises the amino acid sequence set forth in SEQ ID NO:33.

* * * * *